US011938098B2

(12) United States Patent
Badley et al.

(10) Patent No.: US 11,938,098 B2
(45) Date of Patent: Mar. 26, 2024

(54) METHOD FOR KILLING HIV-INFECTED CELLS USING BCL-2 INHIBITORS

(71) Applicant: Mayo Foundation for Medical Education and Research, Rochester, MN (US)

(72) Inventors: Andrew D. Badley, Rochester, MN (US); Amy M. Nguyen, Salt Lake City, UT (US); Scott H. Kaufmann, Rochester, MN (US); Yuan-Ping Pang, Rochester, MN (US); Haiming Dai, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 34 days.

(21) Appl. No.: 17/203,594

(22) Filed: Mar. 16, 2021

(65) Prior Publication Data
US 2021/0379086 A1    Dec. 9, 2021

Related U.S. Application Data

(63) Continuation of application No. 15/567,855, filed as application No. PCT/US2016/028419 on Apr. 20, 2016, now abandoned.

(60) Provisional application No. 62/149,873, filed on Apr. 20, 2015.

(51) Int. Cl.
*A61K 31/00* (2006.01)
*A61K 31/635* (2006.01)
*A61P 31/18* (2006.01)
*A61K 31/21* (2006.01)
*A61K 38/20* (2006.01)
*A61K 45/06* (2006.01)

(52) U.S. Cl.
CPC ............ *A61K 31/00* (2013.01); *A61K 31/635* (2013.01); *A61P 31/18* (2018.01); *A61K 31/21* (2013.01); *A61K 38/2013* (2013.01); *A61K 45/06* (2013.01)

(58) Field of Classification Search
CPC .............................. A61K 31/00; A61P 31/18
See application file for complete search history.

(56) References Cited

U.S. PATENT DOCUMENTS

| | | | |
|---|---|---|---|
| 6,548,536 | B2 | 4/2003 | Hara et al. |
| 10,786,519 | B2 | 9/2020 | Badley |
| 11,376,268 | B2 | 7/2022 | Badley |
| 2002/0091073 | A1 | 7/2002 | Finkel et al. |
| 2003/0232738 | A1 | 12/2003 | Finkel et al. |
| 2009/0010941 | A1 | 1/2009 | Stevenson et al. |
| 2010/0168004 | A1 | 7/2010 | Williams et al. |
| 2014/0256705 | A1 | 9/2014 | Hasvold et al. |
| 2014/0309289 | A1 | 10/2014 | Anderson |
| 2018/0036322 | A1 | 2/2018 | Badley |
| 2018/0161347 | A1 | 6/2018 | Badley et al. |
| 2020/0390789 | A1 | 12/2020 | Badley |

FOREIGN PATENT DOCUMENTS

| | | |
|---|---|---|
| CN | 102690326 | 9/2012 |
| WO | WO 2000/033654 | 6/2000 |
| WO | WO 2006/017346 | 2/2006 |
| WO | WO 2006/023778 | 3/2006 |
| WO | WO 2009/036051 | 3/2009 |
| WO | WO 2011/089166 | 7/2011 |
| WO | WO 2011/089167 | 7/2011 |

OTHER PUBLICATIONS

Yanqin, R., et al., 2020, Bcl-2 antagonism sensitizes cytotoxic T cell-resistant HIV reservoirs to elimination ex vivo, J. Clin. Invest. 130(5):2542-2559.*
Alto, A., et al., Jun. 2021, The combination of venetoclax and ixazomib selectively and efficiently kills HIV-infected cell lines but has unacceptable toxicity in primary cell models, J. Virol. 95(12):e00138-21, pp. 1-11.*
Chun, T.-W., et al., Jun. 2015, HIV reservoirs as obstacles and opportunities for an HIV cure, Nat. Immunol. 16(6):584-589.*
Xing, S., and R. F. Siliciano, Jun. 2013, Targeting HIV latency: pharmacologic strategies toward eradication, Drug Discovery Today 18(11/12):541-552.*
Deeks, S. G., et al., Aug. 2016, International AIDS society global scientific strategy: towards an HIV cure 2016, Nat. Med. 22(8):839-850.*
Margolis, D. M., et al., Jul. 2016, Latency reversal adn viral clearnce to cure HIV-1, Science 353(6297), pp. 1-7.*
Adams et al., "Potent and selective inhibitors of the proteasome: dipeptidyl boronic acids," Bioorg Med Chem Lett., 8(4):333-338, Feb. 17, 1998.
Adams et al., "Proteasome inhibitors: a novel class of potent and effective antitumor agents," Cancer Res., 59(11):2615-2622, Jun. 1, 1999.
Adams, "Development of the proteasome inhibitor PS-341," Oncologist., 7(1):9-16, 2002.
Adams, "Proteasome inhibition in cancer: development of PS-341," Semin Oncol., 28(6):613-619, Dec. 2001.
An et al., "Protease inhibitor-induced apoptosis: accumulation of wt p53, p21WAFI/CIP1, and induction of apoptosis are independent markers of proteasome inhibition," Leukemia., 14(7):1276-1283, Jul. 2000.
Archin et al., "Administration of vorinostat disrupts HIV-1 latency in patients on antiretroviral therapy," Nature., 487(7408):482-485, Jul. 25, 2012.

(Continued)

*Primary Examiner* — Jeffrey S Parkin
(74) *Attorney, Agent, or Firm* — Fish & Richardson P.C.

(57) ABSTRACT

This document provides methods and materials involved in killing HIV infected cells (e.g., CD4 T cells). For example, methods and materials for using one or more Bcl-2 inhibitors (e.g., ABT-199) alone or in combination with one or more agents capable of reactivating HIV (e.g., latency reversing agent) to kill HIV infected cells (e.g., CD4 T cells) are provided.

16 Claims, 30 Drawing Sheets

Specification includes a Sequence Listing.

(56) References Cited

OTHER PUBLICATIONS

Archin et al., "Antiretroviral intensification and valproic acid lack sustained effect on residual HIV-1 viremia or resting CD4+ cell infection," Plos One., 5(2):e9390, Feb. 2010, 4 pages.
Archin et al., "Expression of latent HIV induced by the potent HDAC inhibitor suberoylanilide hydroxamic acid," AIDS Res Hum Retroviruses., 25(2):207-212, Feb. 2009.
Arkin et al., "Small-Molecule Inhibitors of Protein-Protein Interactions: Progressing toward the Reality," Chem Biol., 21(9):1102-1114, 2014.
Badley, "Altering cell death pathways as an approach to cure HIV infection," Cell Death and Dis., 4:e718, Jul. 2013.
Balazs et al., "Antibody-based protection against HIV infection by vectored immunoprophylaxis," Nature., 481(7379):81-84, Nov. 30, 2011.
Bruner et al., "A quantitative approach for measuring the reservoir of latent HIV-1 proviruses," Nature, 556(7742):120-125, Jan. 30, 2019.
Bullen et al., "New ex vivo approaches distinguish effective and ineffective single agents for reversing HIV-1 latency in vivo," Nat Med., 20(4):425-429, Apr. 2014.
Caselli et al., "Short Communication: Activating Transcription Factor 4 (ATF4) Promotes HIV Type 1 Activation," AIDS Res Hum Retroviruses., 28(8):907-912, Aug. 2012.
Chinese Office Action in Chinese Application No. 201680035954.3 dated Nov. 20, 2019, 22 pages.
Choudhary et al., "MCL-1 and BCL-xL-dependent resistance to the BCL-2 inhibitor ABT-199 can be overcome by preventing PI3K/AKT/mTOR activation in lymphoid malignancies," Cell death & disease, 6(1):e1593, Jan. 2015.
Chun, T.-W., et al., Jun. 2015, HIV reservoirs as obstacles and opportunities for an HIV cure, Nat. Innnnunol. 16(6):584-589.
Cooper et al., "HIV-1 causes CD4 cell death through DNA-dependent protein kinase during viral integration," Nature., 498:376-379, Jun. 20, 2013.
Coull et al., "The Human Factors YY1 and LSF Repress the Human Immunodeficiency Virus Type 1 Long Terminal Repeat via Recruitment of Histone Deacetylase 1," J Virol., 74(15):6790-6799, Aug. 2000.
Cummins et al., "Maintenance of the HIV reservoir is antagonized by selective BCL2 inhibition," J Virol., 91(11):e00012-17, Jun. 2017.
Cummins et al., "Prime, shock, and kill: priming CD4 T cells from HIV patients with a BCL-2 antagonist before HIV reactivation reduces HIV reservoir size," J Virol., 90(8):4032-4048, Apr. 2016.
Dai et al., "Proteasome inhibitors potentiate leukemic cell apoptosis induced by the cyclin-dependent kinase inhibitor flavopiridol through a SAPK/JNK- and NF-kappaB-dependent process," Oncogene., 22(46):7108-7122, Oct. 16, 2003.
Deeks and Walker., "Human immunodeficiency virus controllers: mechanisms of durable virus control in the absence of antiretroviral therapy," Immunity., 27:406-416, Sep. 2007.
Deeks et al., "The end of AIDS: HIV infection as a chronic disease," Lancet., 382(9903):1525-1533, Nov. 2, 2013.
Deeks., "Towards an HIV cure: a global scientific strategy," Nature Reviews Immunology., 12:607-614, Jul. 2012.
Doitsh et al., "Abortive HIV infection mediates CD4 T cell depletion and inflammation in human lymphoid tissue," Cell., 143(5):789-801, Nov. 24, 2010.
Dowlatshahi et al., "ALIX Is a Lys63-Specific Polyubiquitin Binding Protein that Functions in Retrovirus Budding," Dev Cell., 23(6):1247-1254, Dec. 11, 2012.
Extended European Search Report in European Application No. 16756096.0, dated Dec. 11, 2018, 245 pages.
Extended European Search Report in European Application No. 16783754.1 dated Oct. 17, 2018, 22 pages.
Fauci et al., "An HIV Cure: Feasibility, Discovery, and Implementation," JAMA., 312(4):335-336, Jul. 23-30, 2014.

Ferguson and Botchan, "Genetic analysis of the activation domain of bovine papillomavirus protein E2: its role in transcription and replication," Journal of Virology, 70(7):4193-9, Jul. 1996.
Fernandez et al., "Differential Regulation of Noxa in Normal Melanocytes and Melanoma Cells by Proteasome Inhibition: Therapeutic Implications," Cancer Res., 65(14):6294-6304, Jul. 15, 2005.
Finzi et al., "Latent infection of CD4+ T cells provides a mechanism for lifelong persistence of HIV-1, even in patients on effective combination therapy," Nat Med., 5(5):512-517, May 1999.
Henrich et al., "Long-term reduction in peripheral blood HIV type 1 reservoirs following reduced-intensity conditioning allogeneic stem cell transplantation," J Infect Dis., 207(11):1694-1702, Jun. 1, 2013.
Hideshima et al., "The proteasome inhibitor PS-341 inhibits growth, induces apoptosis, and overcomes drug resistance in human multiple myeloma cells," Cancer Res., 61(7):3071-3076, Apr. 1, 2001.
Ho et al., "Replication-Competent Noninduced Proviruses in the Latent Reservoir Increase Barrier to HIV-1 Cure," Cell, 155(3):540-551, Oct. 24, 2013.
Holt et al., "Human hematopoietic stem/progenitor cells modified by zinc-finger nucleases targeted to CCR5 control HIV-1 in vivo," Nature Biotech., 28(8):839-847, Aug. 2010.
Hutter et al., "Long-Term Control of HIV by CCR5 Delta32/Delta32 Stem-Cell Transplantation," N Engl. J Med., 360:692-698, Feb. 12, 2009.
International Preliminary Report on Patentability in International Application No. PCT/US2016/018776, dated Sep. 8, 2017, 7 pages.
International Preliminary Report on Patentability of International Application No. PCT/US2016/028419, dated Oct. 24, 2017.
International Search Report and Written Opinion in the International Application No. PCT/US2016/18776, dated Apr. 29, 2016, 9 pages.
International Search Report and Written Opinion of International Application No. PCT/US2016/28419, dated Aug. 15, 2016, 9 pages.
Jostins et al., "Host-microbe interactions have shaped the genetic architecture of inflammatory bowel disease," Nature., 491(7422):119-124, Nov. 1, 2012.
Keedy et al., "A limited group of class I histone deacetylases acts to repress human immunodeficiency virus type 1 expression," J Virol., 83(10):4749-4756, May 2009.
Kikuchi et al., "Histone deacetylases are critical targets of bortezomib-induced cytotoxicity in multiple myeloma," Blood., 116(3):406-417, 2010.
Kitchen et al., "In vivo suppression of HIV by antigen specific T cells derived from engineered hematopoietic stem cells," PLOS Pathog., 8(4):e1002649, Apr. 2012.
Kumar et al., "Safety and tolerability of ixazomib, an oral proteasome inhibitor, in combination with lenalidomide and dexamethasone in patients with previously untreated multiple myeloma: an open-label phase 1/2 study," Lancet., 14:1503-1512, Dec. 2014.
Lam et al., "Switching virally suppressed, treatment-experienced patients to a raltegravir-containing regimen does not alter levels of HIV-1 DNA," PLOS One., 7(3):e31990, 2012.
Ling et al., "PS-341, a novel proteasome inhibitor, induces Bcl-2 phosphorylation and cleavage in association with G2-M phase arrest and apoptosis," Mol Cancer Ther., 1(10):841-849, Aug. 2002.
Liu et al., "Influence of Primate Lentiviral Vif and Proteasome Inhibitors on Human Immunodeficiency Virus Type 1 Virion Packaging of APOBEC3G," J Virol., 78(4):2072-2081, Feb. 2004.
Marban et al., "Recruitment of chromatin-modifying enzymes by CTIP2 promotes HIV-1 transcriptional silencing," EMBO J., 26(2):412-423, 2007.
Margolis, D. M., et al., Jul. 2016, Latency reversal and viral clearance to cure HIV-1, Science 353(6297): aaf6517/1-7.
Martins et al., "Modeling HIV-1 latency in primary T cells using a replication-competent virus," AIDS research and human retroviruses, 32(2):187-93, Feb. 2016.
Mateos et al., "Maintenance therapy with bortezomib plus thalidomide or bortezomib plus prednisone in elderly multiple myeloma patients included in the GEM2005MAS65 trial," Blood., 120(13) 2581-2588, 2012.
Mbita et al., "Human Immunodeficiency Virus-1 (HIV-1 )-Mediated Apoptosis; New Therapeutic Targets," Viruses., 6(8):3181-3227, 2014.

(56) References Cited

OTHER PUBLICATIONS

Mitsiades et al., "Molecular sequelae of proteasome inhibition in human multiple myeloma cells," PNAS USA., 99(22):14374-14379, Oct. 29, 2002.
Mitsiades et al., "The proteasome inhibitor PS-341 potentiates sensitivity of multiple myeloma cells to conventional chemotherapeutic agents: therapeutic applications," Blood., 101(6):2377-2380, Mar. 15, 2003.
Moreau et al. "Oral therapy for multiple myeloma: ixazomib arriving soon" Blood., 2014; 124(7): 986-987.
Moreau et al., "Subcutaneous versus intravenous administration of bortezomib in patients with relapsed multiple myeloma: a randomised, phase 3, non-inferiority study," Lancet Oncol., 12(5):431-40, May 2011.
Natesampillai et al., "The proapoptotic, HIV protease generated Casp8p41 when bound and inactivated by Bcl1, is degraded by the proteasome," J Virol., Posted Online Apr. 11, 2018, Retrieved Aug. 15, 2018, Retrieved from Internet: URL <http://jvi.asm.org/>, 40 pages.
Nie et al., "Human immunodeficiency virus type 1 protease cleaves procaspase 8 in vivo," J Virol., 81(13):6947-6956, Jul. 2007.
Obeng et al., "Proteasome inhibitors induce a terminal unfolded protein response in multiple myeloma cells," Blood., 107(12):4907-4916, Jun. 15, 2006.
Offidani et al., "An evidence-based review of ixazomib citrate and its potential in the treatment of newly diagnosed multiple myeloma," OncoTargets Ther., 7:1793-1800, Sep. 29, 2014.
Petrovas et al., "HIV-specific CD8+ T cells exhibit markedly reduced levels of Bcl-2 and Bcl-xL," J Immunol., 172(7):4444-4453, 2004.
Pham et al., "Global burden of transmitted HIV drug resistance and HIV-exposure categories: a systematic review and meta-analysis," AIDS., 28(18):2751-2762, Nov. 28, 2014.
Qin et al., "Proteasome Inhibitors Trigger NOXA-Mediated Apoptosis in Melanoma and Myeloma Cells," Cancer Res., 65(14):6282-6293, Jul. 15, 2005.
Ren et al., "BCL-2 antagonism sensitizes cytotoxic T cell-resistant HIV reservoirs to elimination ex vivo," The Journal of Clinical Investigation, 130(5):2542-59, May 2020.
Rerks-Ngarm et al., "Vaccination with ALVAC and AIDSVAX to prevent HIV-1 Infection in Thailand," NEJM., 361(23):2209-2220, Dec. 3, 2009.
Richman et al., "The challenge of finding a cure for HIV infection," Science., 323(5919):1304-1307, Mar. 6, 2009.
Run-dong et al., "Research progress of approaches for reactivating HIV-1 latency," Chinese Pharmacological Bulletin, vol. 30(1):1-5, Jan. 2014, (English abstract).
Saleh et al., "CCR7 ligands CCL19 and CCL21 increase permissiveness of resting memory CD4+ T cells to HIV-1 infection: a novel model of HIV-1 latency," Blood., 110(13):4161-4164, Dec. 15, 2007.
Sandstrom et al., "bcl-2 Expression Facilitates Human Immunodeficiency Virus Type 1-Mediated Cytopathic Effects during Acute Spreading Infections," J Virol., 70(7):4617-4622, 1996.
Savarino et al., "Shock and kill effects of class I-selective histone deacetylase inhibitors in combination with the glutathione synthesis inhibitor buthionine sulfoximine in cell line models for HIV-1 quiescence," Retrovirology., 6:52, 2009.
Scholler et al., "Decade-long safety and function of retroviral-modified chimeric antigen receptor T cells," Sci Transl Med., 4(132):132ra53, May 2, 2012.
Shah et al., "26S proteasome inhibition induces apoptosis and limits growth of human pancreatic cancer," J Cell Biochem., 82(1):110-122, Apr. 2-27, 2001.
Shan et al., "Stimulation of HIV-1-specific cytolytic T lymphocytes facilitates elimination of latent viral reservoir after virus reactivation," Immunity., 36:491-501, Mar. 23, 2012.
Souers et al., "ABT-199, a potent and selective BCL-2 inhibitor, achieves antitumor activity while sparingplatelets," Nat Med., 19(2):202-208, 2013.

Strack et al., "Apoptosis mediated by HIV protease is preceded by cleavage of Bcl-2," Proc Natl Acad Sci U S A., 93(18):9571-9576, Sep. 3, 1996.
Sunwoo et al., "Novel proteasome inhibitor PS-341 inhibits activation of nuclear factor-kappa B, cell survival, tumor growth, and angiogenesis in squamous cell carcinoma," Clin Cancer Res., 7(5):1419-1428, May 2001.
Tebas et al., "Gene editing of CCR5 in autologous CD4 T cells of persons infected with HIV," NEJM., 370(10):901-910, Mar. 6, 2014.
Teicher et al., "The proteasome inhibitor PS-341 in cancer therapy," Clin Cancer Res., 5(9):2638-2645, Sep. 1999.
Tsai et al., "Retro-translocation of proteins from the endoplasmic reticulum into the cytosol," Nat Rev Mol Cell Biol., 3(4):246-255, Apr. 1, 2002.
Turan et al., "Changes in protein profiles of multiple myeloma cells in response to bortezomib," Leuk Lymphoma., 54(5):1061-1068, May 2013.
Van Lint et al., "Transcriptional activation and chromatin remodeling of the HIV-1 promoter in response to histone acetylation," EMBO J., 15(5):1112-1120, Mar. 1, 1996.
Wang et al., "Molecules from apoptotic pathways modulate HIV-1 replication in Jurkat cells," Biochem Biophys Res Commun., 414(1):20-24, Oct. 14, 2011.
Warriner et al., "HIV-related metabolic comorbidities in the current ART era," Infect Dis Clin North Am., 28(3):457-476, Sep. 2014.
Wei et al., "MLN2238 synergizes BH3 mimetic ABT-263 in castration-resistant prostate cancer cells by induction of NOXA," Tumour Biol., 35(10):10213-10221, Oct. 2014.
Williams et al., "NF-κB p50 promotes HIV latency through HDAC recruitment and repression of transcriptional initiation," EMBO J., 25(1):139-149, Jan. 11, 2006.
Xing et al., "Disulfiram reactivates latent HIV-1 in a Bcl-2-transduced primary CD4+ T cell model without inducing global T cell activation," J. of Virology, 85(12):6060-4, Jun. 2011.
Xing, S., and R. F. Siliciano, Jun. 2013, Targeting HIV latency: pharmacologic strategies toward eradication, Drug Discov. Today 18(11/12):541-551.
Yu et al., "Proteasome inhibitors block HIV-1 replication by affecting both cellular and viral targets," Biochemical and Biophysical Research Communications., 385(1):100-105, Jul. 17, 2009.
Zhang et al., "Bcl-2 upregulation by HIV-1 Tat during infection of primary human macrophages in culture," J Biomed Sci., 9(2):133-139, Mar.-Apr. 2002.
Chandrasekar et al., "The BCL-2 Inhibitor Venetoclax Augments Immune Effector Function Mediated by Fas Ligand, TRAIL, and Perforin/Granzyme B, Resulting in Reduced Plasma Viremia and Decreased HIV Reservoir Size during Acute HIV Infection in a Humanized Mouse Model," J. Virol., Nov. 30, 2022, 96(24):e0173022, 16 pages.
Natesampillai et al., "HIV Protease-Generated Casp8p41, When Bound and Inactivated by Bcl2, Is Degraded by the Proteasome," J. Virol., Jun. 13, 2018, 92(13):e00037-18, 14 pages.
Achenbach et al., "Effect of therapeutic intensification followed by HIV DNA prime and rAd5 boost vaccination on HIV-specific immunity and HIV reservoir (EraMune 02): a multicentre randomised clinical trial," Lancet HIV, Mar. 2015, 2(3):e82-e91.
Algeciras-Schimnich et al., "Analysis of HIV Protease Killing Through Caspase 8 Reveals a Novel Interaction Between Caspase 8 and Mitochondria," Open Virol. Journal, Dec. 27, 2007, 1:39-46.
Altmann et al., "Epstein-Barr virus provides a new paradigm: a requirement for the immediate inhibition of apoptosis," PLoS Biology, Dec. 2005, 3(12):e404, 10 pages.
Anders et al., "Differential expression analysis for sequence count data," Genome Biology, Oct. 27, 2010, 11:R106, 12 pages.
Archin et al., "HIV-1 expression within resting CD4+ T cells after multiple doses of vorinostat," J. Infect. Diseases, Sep. 2014, 210(5):728-735.
Ashburner et al., "Gene ontology: tool for the unification of biology. The Gene Ontology Consortium," Nat. Genetics, May 2000, 25(1):25-29.
Baccarani et al., "European LeukemiaNet recommendations for the management of chronic myeloid leukemia: 2013," Blood, Aug. 8, 2013, 122(6):872-874.

(56) References Cited

OTHER PUBLICATIONS

Berendsen et al., "Molecular dynamics with coupling to an external bath," J. Chem. Physics, 1984, 31(8):3684-3690.
Bhat et al., "Biophysical basis of the promiscuous binding of B-cell lymphoma protein 2 apoptotic repressor to BH3 ligands," J. Mol Recognition, Oct. 2013, 26(10):501-513.
Bren et al., "Infected Cell Killing by HIV-1 Protease Promotes NF-κB Dependent HIV-1 Replication," PLoS One, May 7, 2008, 3(5):e2112, 7 pages.
Brenchley et al., "CD4+ T cell depletion during all stages of HIV disease occurs predominantly in the gastrointestinal tract," J. Exp. Medicine, Sep. 20, 2004, 200(6):749-759.
Brenchley et al., "T-Cell Subsets That Harbor Human Immunodeficiency Virus (HIV) In Vivo: Implications for HIV Pathogenesis," J. Virology, Feb. 2004, 78(3):1160-1168.
Chen et al., "Differential targeting of prosurvival Bcl-2 proteins by their BH3-only ligands allows complementary apoptotic function," Mol. Cell, Feb. 4, 2005, 17(3):393-403.
Chinnaiyan et al., "The inhibition of pro-apoptotic ICE-like proteases enhances HIV replication," Nat. Medicine, Mar. 1997, 3(3):333-337.
Chomont et al., "HIV reservoir size and persistence are driven by T cell survival and homeostatic proliferation," Nat. Medicine, Jun. 21, 2009, 15(8):893-900.
Clem et al., "Control of programmed cell death by the baculovirus genes p35 and iap," Mol. Cell Biology, Aug. 1994, 14(8):5212-5222.
Clem et al., "Prevention of apoptosis by a baculovirus gene during infection of insect cells," Science, Nov. 19, 1991, 254(5036):1388-1390.
Correia et al., "BCL2 mutations are associated with increased risk of transformation and shortened survival in follicular lymphoma," Blood, Jan. 22, 2015, 125(4):658-667.
Correia et al., "Emerging understanding of Bcl-2 biology: Implications for neoplastic progression and treatment," Biochim. Biophys. Acta, Jul. 2015, 1853(7):1658-1671.
Cummins et al., "Anti-apoptotic mechanisms of HIV: lessons and novel approaches to curing HIV," Cell Mol. Life Sciences, Sep. 2013, 70(18):3355-3363.
Cummins et al., "Intracellular Casp8p41 content is inversely associated with CD4 T cell count," J. Infect. Diseases, Aug. 15, 2010, 202(3):386-391.
Cummins et al., "Mechanisms of HIV-associated lymphocyte apoptosis: 2010," Cell Death Disease, Nov. 11, 2010, 1(11):e99, 9 pages.
Cummins et al., "Prime, Shock, and Kill: Priming CD4 T Cells from HIV Patients with a BCL-2 Antagonist before HIV Reactivation Reduces HIV Reservoir Size," J. Virology, Apr. 15, 2016, 90(8):4032-4048.
Cummins et al., "Short communication: CD4 T cell declines occurring during suppressive antiretroviral therapy reflect continued production of Casp8p41," AIDS Res. Hum. Retroviruses, May 2014, 30(5):476-479.
Czabotar et al., "Control of apoptosis by the BCL-2 protein family: implications for physiology and therapy," Nat. Rev. Mol. Cell Biology, Jan. 2014, 15(1):49-63.
Dai et al., "Context-dependent Bcl-2/Bak interactions regulate lymphoid cell apoptosis," J. Biol. Chemistry, Jul. 3, 2009, 284(27):18311-18322.
Dai et al., "Evaluation of the BH3-only protein Puma as a direct Bak activator," J. Biol. Chemistry, Jan. 3, 2014, 289(1):89-99.
Dai et al., "Transient binding of an activator BH3 domain to the Bak BH3-binding groove initiates Bak oligomerization," J. Cell. Biology, Jul. 11, 2011, 194(1):39-48.
Darden et al., "Particle mesh Ewald: An N•log(N) method for Ewald sums in large systems," J. Chem. Physics, Mar. 5, 1993, 98:10089-10092.
Davids et al., "Phase I study of ABT-199 (GDC-0199) in patients with relapsed/refractory (R/R) non-Hodgkin lymphoma (NHL): responses observed in diffuse large B-cell (DLBCL) and follicular lymphoma (FL) at higher cohort doses," Abstract, J. Clin. Oncology, May 20, 2014, 32(15S):8522, 2 pages.
Deeks, "HIV: Shock and kill," Nature, Jul. 25, 2012, 487(7408):439-440.
Deng et al., "Broad CTL response is required to clear latent HIV-1 due to dominance of escape mutations," Nature, Jan. 7, 2015, 517(7534):381-385.
Dietz et al., "A novel source of viable peripheral blood mononuclear cells from leukoreduction system chambers," Transfusion, Dec. 2006, 46(12):2083-2089.
Diez et al., "DeathBase: a database on structure, evolution and function of proteins involved in apoptosis and other forms of cell death," Cell Death Differentiation, May 2010, 17(5):735-736.
Doitsh et al., "Cell death by pyroptosis drives CD4 T-cell depletion in HIV-1 infection," Nature, Jan. 23, 2014, 505(7484):509-514.
Elliott et al., "Activation of HIV transcription with short-course vorinostat in HIV-infected patients on suppressive antiretroviral therapy," PLoS Pathogens, Nov. 13, 2014, 10(10):e1004473, 19 pages.
Eriksson et al., "Comparative analysis of measures of viral reservoirs in HIV-1 eradication studies," PLoS Pathogens, Feb. 2013, 9(2):e1003174, 17 pages.
Finkel et al., "Apoptosis occurs predominantly in bystander cells and not in productively infected cells of HIV and SIV-infected lymph nodes," Nat. Medicine, Feb. 1995, 1(2):129-134.
Fraietta et al., "Type I interferon upregulates Bak and contributes to T cell loss during human immunodeficiency virus (HIV) infection," PLoS Pathogens, Oct. 10, 2013, 9(10):e1003658, 16 pages.
Grimm et al., "Bcl-2 down-regulates the activity of transcription factor NF-kappaB induced upon apoptosis," J. Cell. Biology, Jul. 1996, 134(1):13-23.
Harari et al., "Phenotypic heterogeneity of antigen-specific CD4 T cells under different conditions of antigen persistence and antigen load," Eur. J. Immunology, Dec. 2004, 34(12):3525-3533.
Henrich et al., "Antiretroviral-free HIV-1 remission and viral rebound after allogeneic stem cell transplantation: report of 2 cases," Ann. Intern. Medicine, Sep. 2, 2014, 161(5):319-327.
Henrich et al., "Impact of Systemic Cytotoxic Chemotherapy for Malignancies on HIV-1 Reservoir Persistence," Abstract, Presented at Proceedings of the Conference on Retroviruses and Opportunistic Infections, Mar. 13-16, 2014, Boston MA, USA, 1 page.
Houge et al., "Fine mapping of 28S rRNA sites specifically cleaved in cells undergoing apoptosis," Mol. Cell. Biology, Apr. 1995, 15(4):2051-2062.
Jaafoura et al., "Progressive contraction of the latent HIV reservoir around a core of less-differentiated CD4+ memory T Cells," Nat. Communications, Nov. 10, 2014, 5:5407, 8 pages.
Jiang et al., "Structural basis of RNA recognition and activation by innate immune receptor RIG-I," Nature, Sep. 25, 2011, 479(7373):423-427.
Josefsson et al., "The HIV-1 reservoir in eight patients on long-term suppressive antiretroviral therapy is stable with few genetic changes over time," Proc. Natl. Acad. Sci. USA, Nov. 25, 2013, 110(51):E4987-E4996.
Kanehisa et al., "KEGG: kyoto encyclopedia of genes and genomes," Nucelic Acids Research, Jan. 1, 200, 28(1):27-30.
Kaplan et al., "The activity of the protease of human immunodeficiency virus type 1 is initiated at the membrane of infected cells before the release of viral proteins and is required for release to occur with maximum efficiency," J. Virology, Oct. 1994, 68(10):6782-6786.
Kaplan et al., "The HIV-1 gag precursor is processed via two pathways: implications for cytotoxicity," Biomed. Biochim. Acta, 1991, 50(4-6):647-653.
Karpel et al., "BLT humanized mice as a small animal model of HIV infection," Curr. Opin. Virology, Aug. 2015, 13:75-80.
Kelve et al., "Rapid reduction of mRNA coding for 2=-5=-oligoadenylate synthetase in rat pheochromocytoma PC12 cells during apoptosis," Cell Mol. Biology, Mar. 1994, 40(2):165-173.
Kennedy et al., "Inactivation of the human papillomavirus E6 or E7 gene in cervical carcinoma cells by using a bacterial CRISPR/Cas RNA-guided endonuclease," J. Virology, Oct. 2014, 88(20):11965-11972.

(56) References Cited

OTHER PUBLICATIONS

Kim et al., "A primary CD4(+) T cell model of HIV-1 latency established after activation through the T cell receptor and subsequent return to quiescence," Nat. Protocols, Dec. 2014, 9(12):2755-2770.
Kumar et al., "Phase I interim safety and efficacy of venetoclax (ABT-199/GDC-0199) monotherapy for relapsed/refractory (R/R) multiple myeloma (MM)," Abstract, J. Clin. Oncology, May 20, 2015, 33(15S):8576, 2 pages.
Laforge et al., "DRAM triggers lysosomal membrane permeabilization and cell death in CD4(+) T cells infected with HIV," PLoS Pathogens, May 2, 2013, 9(5):e1003328, 14 pages.
Laird et al., "Ex vivo analysis identifies effective HIV-1 latency-reversing drug combinations," J. Clin. Investigation, May 2015, 125(5):1901-1912.
Liszewski et al., "Detecting HIV-1 integration by repetitive-sampling Alu-gag PCR," Methods, Apr. 2009, 47(4):254-260.
López-Huertas et al., "The presence of HIV-1 Tat protein second exon delays fas protein-mediated apoptosis in CD4+ T lymphocytes: a potential mechanism for persistent viral production," J. Biol. Chemistry, Mar. 15, 2013, 288(11):7626-7644.
Lum et al., "Resistance to apoptosis: mechanism for the development of HIV reservoirs," Curr. HIV Research, Jul. 2003, 1(3):261-274.
Lüthi et al., "The CASBAH: a searchable database of caspase substrates," Cell Death Differentiation, Apr. 2007, 14(4):641-650.
Macallan et al., "Rapid Turnover of Effector-Memory CD4+ T Cells in Healthy Humans," J. Exp. Medicine, Jul. 19, 2004, 200(2):255-260.
Mahlknecht et al., "Resistance to apoptosis in HIV-infected CD4+ T lymphocytes is mediated by macrophages: role for Nef and immune activation in viral persistence," J. Immunology, Dec. 1, 2000, 165(11):6437-6446.
Mangeat et al., "Broad antiretroviral defence by human APOBEC3G through lethal editing of nascent reverse transcripts," Nature, May 28, 2003, 424(6944):99-103.
Martinou et al., "Mitochondria in apoptosis: Bcl-2 family members and mitochondrial dynamics," Dev. Cell, Jul. 19, 2011, 21(1):92-101.
Monroe et al., "IFI16 DNA sensor is required for death of lymphoid CD4 T cells abortively infected with HIV," Science, Jan. 24, 2014, 343(6169):428-432.
Mortenson et al., "BCL-2 functions as an activator of the AKT signaling pathway in pancreatic cancer," J. Cell. Biochemistry, Dec. 1, 2007, 102(5):1171-1179.
Natesampillai et al., "Patients with discordant responses to antiretroviral therapy have impaired killing of HIV-infected T cells," PLoS Pathogens, Nov. 24, 2010, 6(11):e1001213, 15 pages.
Nie et al., "HIV Protease Cleavage of Procaspase 8 is Necessary for Death of HIV-Infected Cells," Open Virol. Journal, Jan. 22, 2008, 2:1-7.
Nie et al., "HIV-1 protease processes procaspase 8 to cause mitochondrial release of cytochrome c, caspase cleavage and nuclear fragmentation," Cell Death Differentiation, Nov. 2002, 9(11):1172-1184.
Olesen et al., "Innate Immune Activity Correlates with CD4 T Cell-Associated HIV-1 DNA Decline during Latency-Reversing Treatment with Panobinostat," J. Virology, Sep. 22, 2015, 89(20):10176-10189.
Pallikkuth et al., "Peripheral T follicular helper cells are the major HIV reservoir within central memory CD4 T cells in peripheral blood from chronic HIV-infected individuals on cART," J. Virology, Dec. 16, 2015, 90(6):2718-2728.
Pang, "At least 10% shorter C—H bonds in cryogenic protein crystal structures than in current AMBER forcefields," Biochem. Biophys. Res. Communications, Feb. 4, 2015, 458(2):352-355.
Pang, "Low-mass molecular dynamics simulation for configurational sampling enhancement: more evidence and theoretical explanation," Biochem. Biophys. Reports, Sep. 2, 2015, 4:126-133.
Pang, "Low-mass molecular dynamics simulation: a simple and generic technique to enhance configurational sampling," Biochem. Biophys. Res. Communications, Sep. 26, 2014, 452(3):588-592.
Pang, "Use of 1-4 interaction scaling factors to control the conformational equilibrium between α-helix and β-strand," Biochem. Biophys. Res. Communications, Dec. 25, 2014, 457(2):183-186.
Pegu et al., "Activation and lysis of human CD4 cells latently infected with HIV-1," Nat. Communications, Oct. 20, 2015, 6:8447, 9 pages.
Pilder et al., "Deletion of the gene encoding the adenovirus 5 early region 1b 21,000-molecular-weight polypeptide leads to degradation of viral and host cell DNA," J. Virology, Nov. 1984, 52(2):664-671.
Puertas et al., "Intensification of a raltegravir-based regimen with maraviroc in early HIV-1 infection," AIDS, Jan. 28, 2014, 28(3):325-334.
Rasmussen et al., "Panobinostat, a histone deacetylase inhibitor, for latent-virus reactivation in HIV-infected patients on suppressive antiretroviral therapy: a phase 1/2, single group, clinical trial," Lancet HIV, Oct. 2014, 1(1):e13-e21.
Roche.com [online], "US FDA grants breakthrough therapy designation for investigational Bcl-2 inhibitor venetoclax in 17p deletion relapsed-refractory chronic lymphocytic leukemia," May 6, 2015, retrieved on Oct. 4, 2022, retrieved from URL<https://www.roche.com/investors/updates/inv-update-2015-05-07>, 5 pages.
Rubenwolf et al., "Structural analysis of the adenovirus type 5 E1B 55-kilodalton-E4orf6 protein complex," J. Virology, Feb. 1997, 71(2):1115-1123.
Sainski et al., "Casp8p41 generated by HIV protease kills CD4 T cells through direct Bak activation," J. Cell. Biology, Sep. 22, 2014, 206(7):867-876.
Sainski et al., "Correction: Casp8p41 generated by HIV protease kills CD4 T cells through direct Bak activation," J. Cell. Biology, Sep. 29, 2014, 207(1):159.
Sainski et al., "The HIV-1-specific protein Casp8p41 induces death of infected cells through Bax/Bak," J. Virology, Aug. 2011, 85(16):7965-7975.
Samejima et al., "Trashing the genome: the role of nucleases during apoptosis," Nat. Rev. Mol. Cell. Biology, Sep. 2005, 6(9):677-688.
Seymour et al., Bcl-2 Inhibitor ABT-199 (GDC-0199) Monotherapy Shows Anti-Tumor Activity Including Complete Remissions in High-Risk Relapsed/Refractory (R/R) Chronic Lymphocytic Leukemia (CLL) and Small Lymphocytic Lymphoma (SLL), Abstract, Blood, Nov. 15, 2013, 122(21):872, 7 pages.
Shao et al., "Clustering Molecular Dynamics Trajectories: 1. Characterizing the Performance of Different Clustering Algorithms," J. Chem. Theory Computation, Nov. 2007, 3(6):2312-2334.
Smith et al., "Noxa/Bcl-2 protein interactions contribute to bortezomib resistance in human lymphoid cells," J. Biol. Chemistry, May 20, 2011, 286(20):17682-17692.
Søgaard et al., "The depsipeptide romidepsin reverses HIV-1 latency in vivo," PLoS Pathogens, Sep. 17, 2015, 11:e1005142, 22 pages.
Sok et al., "The effects of somatic hypermutation on neutralization and binding in the PGT121 family of broadly neutralizing HIV antibodies," PLoS Pathogens, Nov. 21, 2013, 9(11):e1003754.
Solis et al., "RIG-I-mediated antiviral signaling is inhibited in HIV-1 infection by a protease-mediated sequestration of RIG-I," J. Virology, Feb. 2011, 85(3):1224-1236.
Spina et al., "An in-depth comparison of latent HIV-1 reactivation in multiple cell model systems and resting CD4+ T cells from aviremic patients," PLoS Pathogens, Dec. 26, 2013, 9(12):e1003834, 15 pages.
Stürzl et al., "Expression of K13/v-FLIP gene of human herpesvirus 8 and apoptosis in Kaposi's sarcoma spindle cells," J. Natl. Cancer Institute, Oct. 20, 1999, 91(20):1725-1733.
Takeshita et al., "Polarization diversity of human CD4+ stem cell memory T cells," Clin. Immunology, Apr. 27, 2015, 159(1):107-117.
Taylor et al., "Apoptosis: controlled demolition at the cellular level," Nat. Rev. Mol. Cell. Biology, Mar. 2008, 9(3):231-241.
Tse et al., "ABT-263: a potent and orally bioavailable Bcl-2 family inhibitor," Cancer Research, May 1, 2008, 68(9):3421-3428.

(56) References Cited

OTHER PUBLICATIONS

Van Grevenynghe et al., "Transcription factor FOXO3a controls the persistence of memory CD4(+) T cells during HIV infection," Nat. Medicine, Mar. 2008, 14(3):266-274.
Vandergeeten et al., "Interleukin-7 promotes HIV persistence during antiretroviral therapy," Blood, May 23, 2013, 121(21):4321-4329.
Waterhouse et al., "Heteronuclear ribonucleoproteins C1 and C2, components of the spliceosome, are specific targets of interleukin 1beta-converting enzyme-like proteases in apoptosis," J. Biol. Chemistry, Nov. 15, 1996, 271(46):29335-29341.
Widlak et al., "Discovery, regulation, and action of the major apoptotic nucleases DFF40/CAD and endonuclease G," J. Cell. Biochemistry, Apr. 15, 2005, 94(6):1078-1087.
Wolf et al., "HIV-1 Nef associated PAK and PI3-kinases stimulate Akt-independent Bad-phosphorylation to induce anti-apoptotic signals," Nat. Medicine, Nov. 2001, 7(11):1217-1224.
Xu et al., "Apigenin, a dietary flavonoid, sensitizes human T cells for activation-induced cell death by inhibiting PKB/Akt and NF-kappaB activation pathway," Immunol. Letters, Nov. 16, 2008, 121(1):74-83.
Yip et al., "Bcl-2 family proteins and cancer," Oncogene, Oct. 27, 2008, 27(50):6398-6406.
Jiang et al., "c-Myc and Sp1 Contribute to Proviral Latency by Recruiting Histone Deacetylase 1 to the Human Immunodeficiency Virus Type 1 Promoter," J. Virol., Oct. 2007, 81(20):10914-10923.
Miller et al., "Proteasome inhibitors act as bifunctional antagonists of human immunodeficiency virus type 1 latency and replication," Retrovirology, Oct. 2013, 10:120.
Porter et al., "Chimeric Antigen Receptor—Modified T Cells in Chronic Lymphoid Leukemia," N. Engl. J. Med., Aug. 2011, 365:725-733.
Shan et al., "From reactivation of latent HIV-1 to elimination of the latent reservoir: the presence of multiple barriers to viral eradication," Bioessays, Jun. 2013, 35(6):544-552.

\* cited by examiner

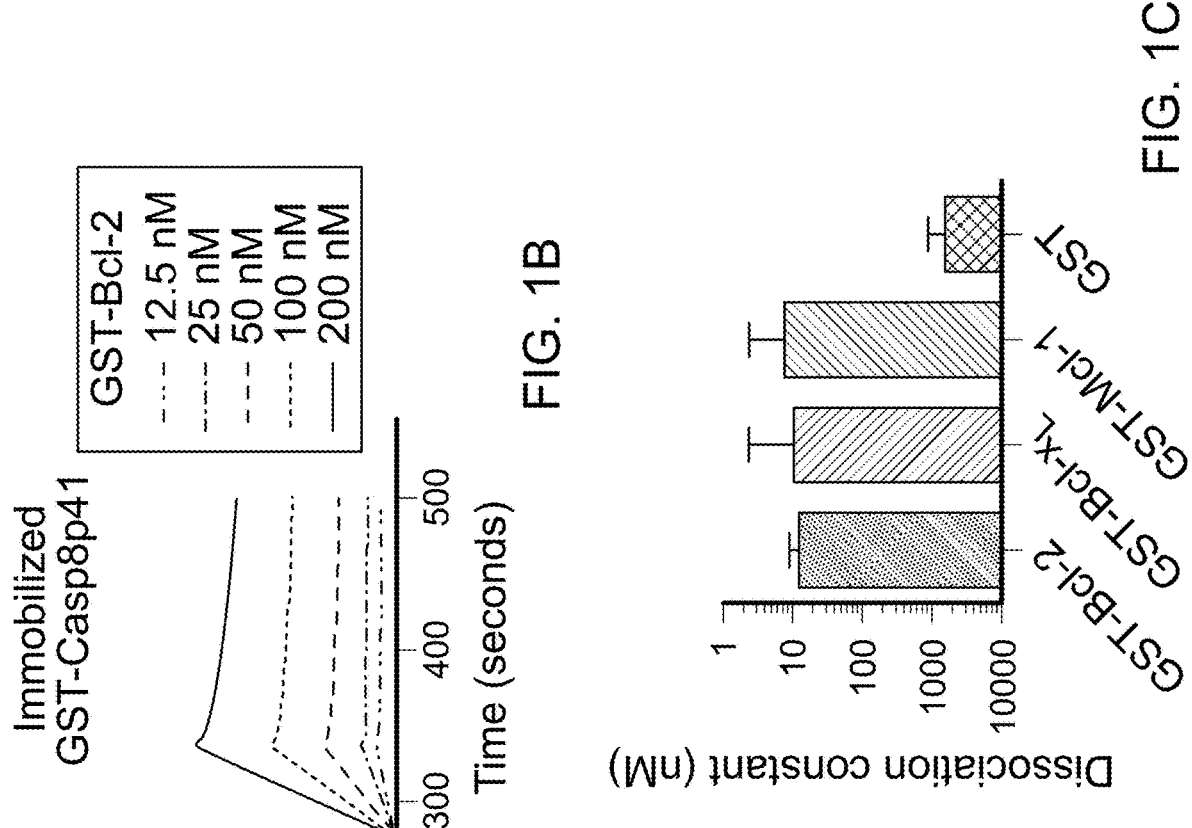
FIG. 1B
FIG. 1C
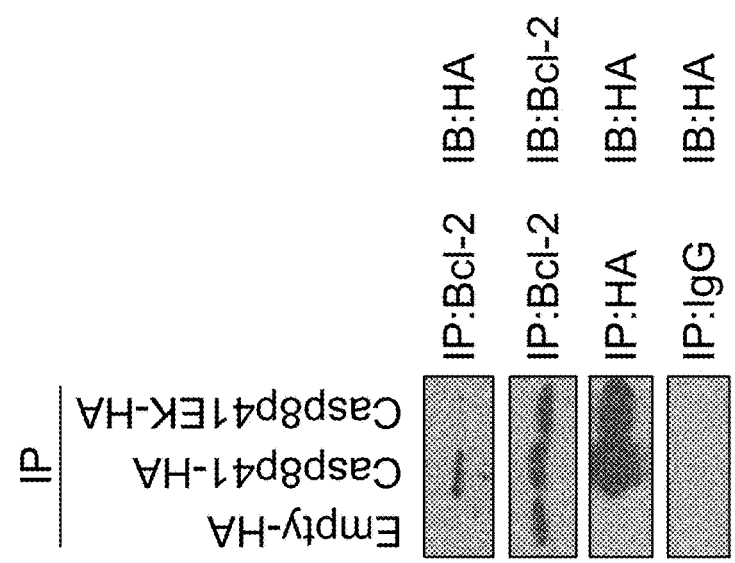
FIG. 1A

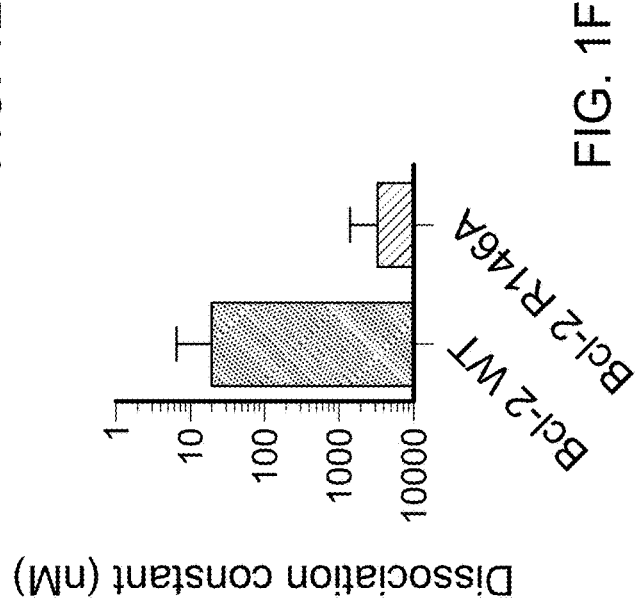
FIG. 1E
FIG. 1F
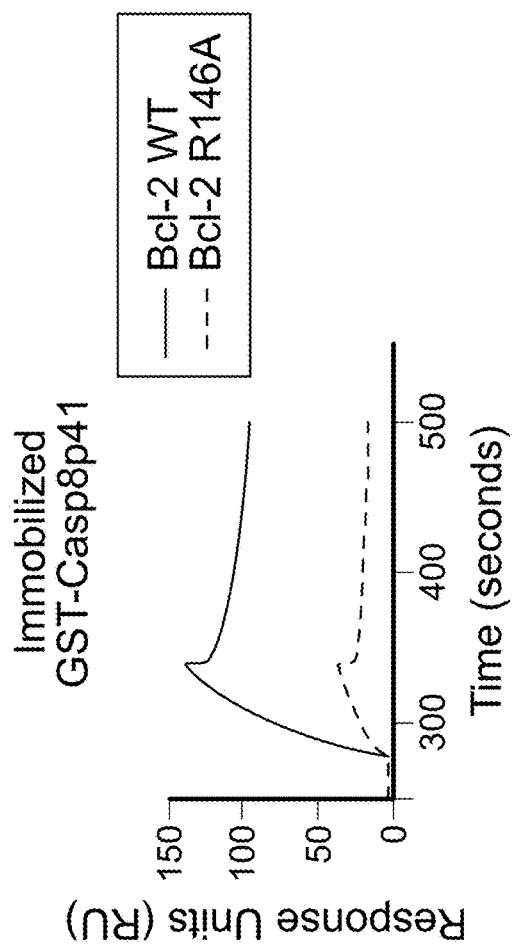
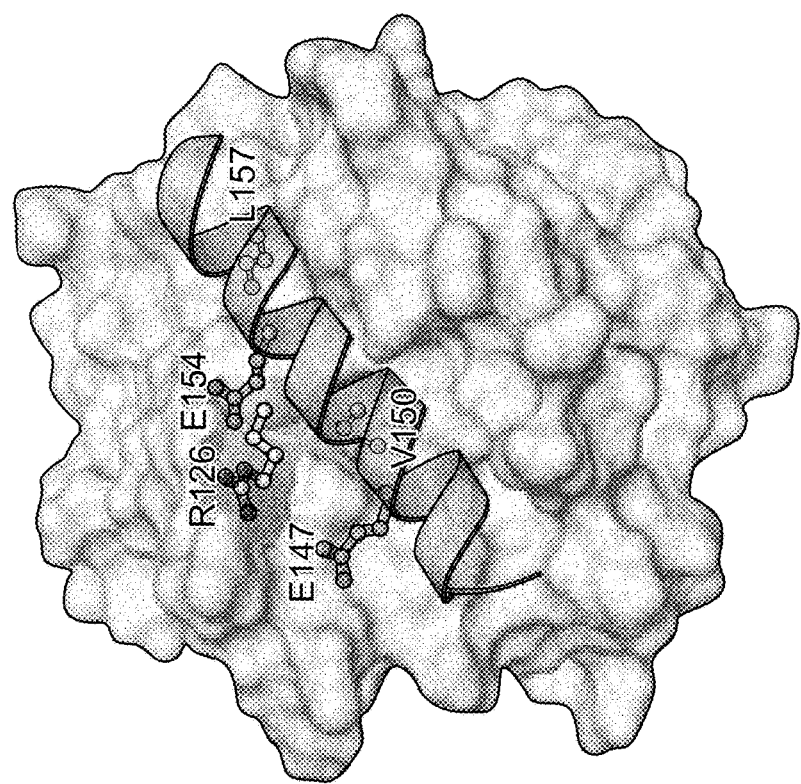
FIG. 1D

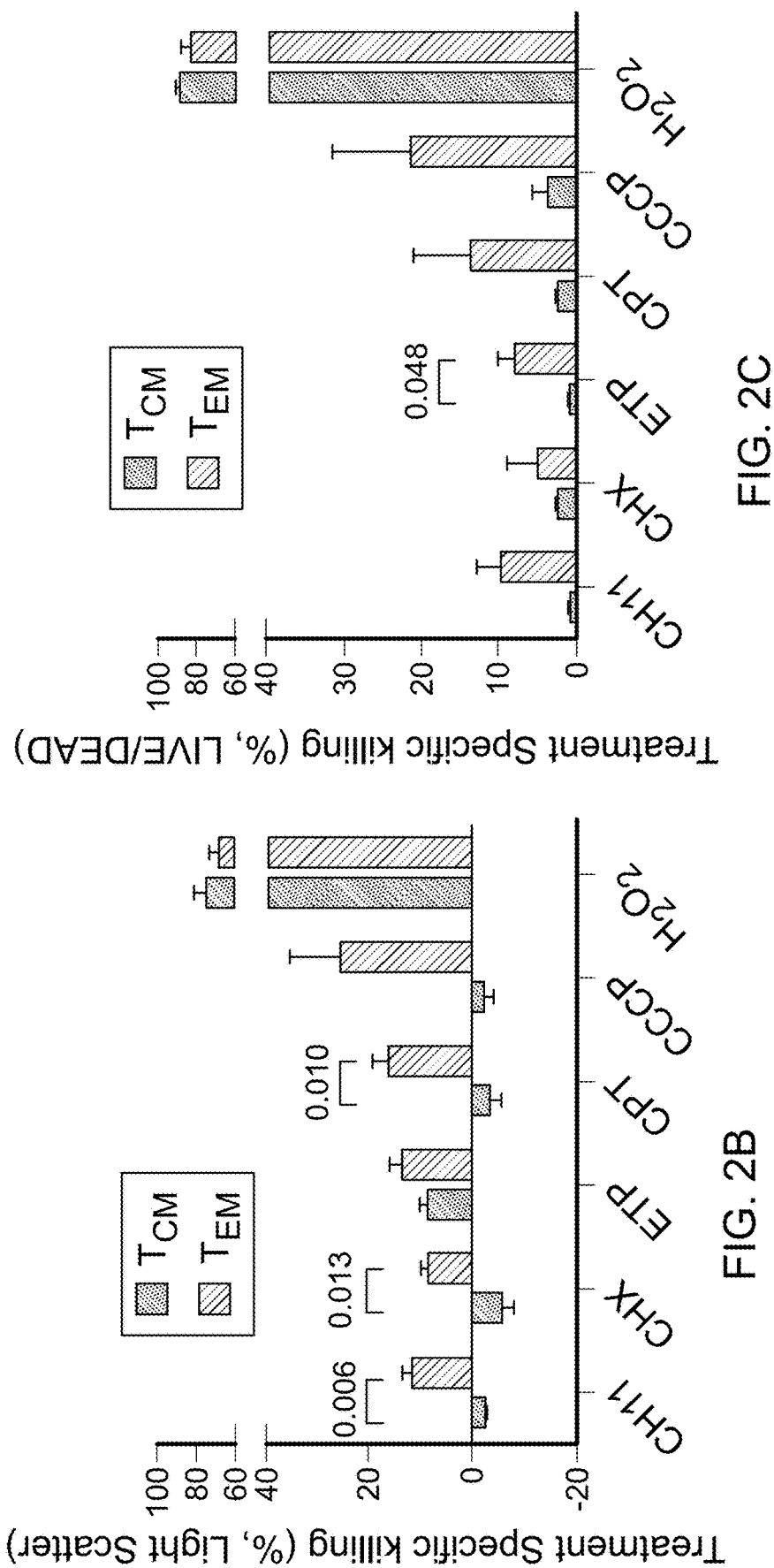

SEQUENCE LISTING

```
<160> NUMBER OF SEQ ID NOS: 5

<210> SEQ ID NO 1
<211> LENGTH: 31
<212> TYPE: PRT
<213> ORGANISM: artificial
<220> FEATURE:
<223> OTHER INFORMATION: Casp8p41 BH3-like peptide

<400> SEQUENCE: 1

Asp Met Asn Leu Leu Asp Ile Phe Ile Glu Met Glu Lys Arg Val Ile
1               5                   10                  15

Leu Gly Glu Gly Lys Leu Asp Ile Leu Lys Arg Val Cys Ala Gln
            20                  25                  30

<210> SEQ ID NO 2
<211> LENGTH: 23
<212> TYPE: PRT
<213> ORGANISM: artificial
<220> FEATURE:
<223> OTHER INFORMATION: N-terminal control peptide

<400> SEQUENCE: 2

Met Asp Phe Ser Arg Asn Leu Tyr Asp Ile Gly Glu Gln Leu Asp Ser
1               5                   10                  15

Glu Asp Leu Ala Ser Leu Lys
            20
```

```
<210> SEQ ID NO 3
<211> LENGTH: 22
<212> TYPE: DNA
<213> ORGANISM: artificial
<220> FEATURE:
<223> OTHER INFORMATION: Synthetic primer

<400> SEQUENCE: 3
ttaagcctca ataaagcttg cc                                              22

<210> SEQ ID NO 4
<211> LENGTH: 20
<212> TYPE: DNA
<213> ORGANISM: artificial
<220> FEATURE:
<223> OTHER INFORMATION: Synthetic primer

<400> SEQUENCE: 4
gttcgggcgc cactgctaga                                                 20

<210> SEQ ID NO 5
<211> LENGTH: 26
<212> TYPE: DNA
<213> ORGANISM: artificial
<220> FEATURE:
<223> OTHER INFORMATION: Synthetic probe

<400> SEQUENCE: 5
ccagagtcac acaacagacg ggcaca                                          26
```

METHOD FOR KILLING HIV-INFECTED CELLS USING BCL-2 INHIBITORS

CROSS-REFERENCE TO RELATED APPLICATIONS

This application is a continuation of U.S. application Ser. No. 15/567,855, filed Oct. 19, 2017, which is a National Stage application under 35 U.S.C. § 371 of International Application No. PCT/US2016/028419, having an International Filing Date of Apr. 20, 2016, which claims priority to U.S. Application Ser. No. 62/149,873, filed on Apr. 20, 2015. The disclosure of the prior applications are considered part of the disclosure of this application, and are incorporated in its entirety into this application.

BACKGROUND

1. Technical Field

This document relates to methods and materials involved in killing HIV infected cells (e.g., CD4 T cells). For example, this document provides methods and materials for using one or more Bcl-2 inhibitors (e.g., ABT-199) alone or in combination with one or more agents capable of reactivating HIV (e.g., latency reversing agent) to kill HIV infected cells (e.g., CD4 T cells).

2. Background Information

HIV is a retrovirus that causes the acquired immunodeficiency syndrome (AIDS), which is a medical condition where progressive failure of the immune system leads to life-threatening opportunistic infections. The HIV infection, while treatable for long periods of time, remains a largely incurable infection. On the other hand, an HIV infection was "cured" in one patient, which involved using myeloablative chemotherapy and maximally suppressive antiretroviral therapy (ART), followed by bone marrow transplantation (BMT; Hatter et al., *N. Engl. J. Med.*, 360:692-698 (2009)).

SUMMARY

This document provides methods and materials involved in killing HIV infected cells (e.g., CD4 T cells). For example, this document provides methods and materials for using one or more Bcl-2 inhibitors (e.g., ABT-199) alone or in combination with one or more agents capable of reactivating HIV (e.g., latency reversing agent) to kill HIV infected cells (e.g., CD4 T cells). As described herein, Bcl-2 inhibitors (e.g., ABT-199) alone or in combination with one or more agents capable of reactivating HIV (e.g., latency reversing agent) can be used to kill HIV infected cells (e.g., CD4 T cells such as latently HIV infected CD4 T cells or central memory CD4 T cells).

In general, one aspect of this document features a method for killing HIV infected cells within a human infected with HIV. The method comprises, or consist essentially of, (a) administering a Bcl-2 inhibitor to the human, and (b) administering a latency reversing agent to the human. The cells can be $CD4^+$ T cells. The Bcl-2 inhibitor can be ABT-199. The latency reversing agent can be selected from the group consisting of an HDAC inhibitor, a phorbol ester, IL-2, and a bromodomain inhibitor.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DESCRIPTION OF DRAWINGS

FIGS. 1A-1F. Casp8p41 binds the BH3 binding grooves of antiapoptotic Bcl-2 family members. FIG. 1A, 293T cells transfected with HA-empty vector, HA-Casp8p41, or HA-Casp8p41EK were immunoprecipitated with anti-HA-conjugated beads or agarose conjugated antibody (control IgG or Bcl-2) and immunoblotted as indicated. FIG. 1B, Binding of 12.5-200 nM GST-Bcl-2 to immobilized GST-Casp8p41 as assessed by SPR. FIG. 1C, KDs of GST-Bcl-2, GST-Bcl-xL and GST-Mcl-1 binding to GST-Casp8p41. FIG. 1D, Multiple low-mass molecular dynamics simulation-refined model of the Casp8p41 activator domain (green) binding the human Bcl-2 BH3-binding groove. FIG. 1E, Binding of 800 nM GST-Bcl-2 or GST-Bcl-2 R146A to immobilized Casp8p41. FIG. 1F, KDs determined as in panel E.

FIGS. 2A-2I. $T_{CM}$ are more resistant to cell death than $T_{EM}$. FIG. 2A, Representative flow data demonstrating immunophenotyping gating strategy for naïve, central memory, and effector memory CD4 T cell analysis (left panel); light scatter characterization of cell viability and LIVE/DEAD staining for cell viability and death (right panel). FIGS. 2B and 2C, PBMCs from 3 uninfected donors were treated overnight with agonistic anti-Fas antibody CH11, cycloheximide (CHX), etoposide (ETP), camptothecin (CPT), carbonyl cyanide 3-chlorophenylhydrazone (CCCP) or $H_2O_2$, cell death was assessed by flow cytometry using light scatter (FIG. 2B) and LIVE/DEAD stains (FIG. 2C). FIG. 2D, $T_{CM}$ and $T_{EM}$ were isolated from two HIV-infected donors by magnetic bead separation and gene expression measured by NGS. Depicted are differentially expressed genes associated with cell proliferation and cell death sorted by log 2 fold change. Cell proliferation genes are at the top of the figure and cell death genes below. FIG. 2E, Cytosolic extracts from $T_{CM}$ and $T_{EM}$ were assessed for expression of procaspase 8 (Casp8) and Bcl-2 by Western blot and densitometry. Representative of three experiments. FIG. 2F, PBMCs from 2 HIV-infected patients were assessed for intracellular Casp8p41 expression in T cell subsets, using CD3-negative cells as the negative gating control. PBMCs from five HIV-infected patients were assessed for intracellular Casp8p41 expression in $CD4^+$ T cell subsets and in CD3 negative cells (FIG. 2G). Depicted is representative flow cytometry data showing the gating strategy to determine intracellular Casp8p41 expression in $CD4^+$ T cell subsets: Naïve (TN), Central Memory (TCM), Effectory Memory (TEM), and total CD4 T cells (FIG. 2H). CD3- cells, which are not infected by HIV and thus do not express HIV protease, were used as negative gating controls. FIG.

2I, Gene expression differences in TCM versus TEM were validated in a separate publicly available dataset of 6 uninfected donors.

Figure 3B:
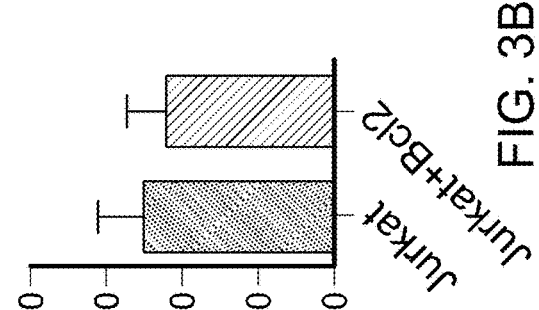
Figure 3B:
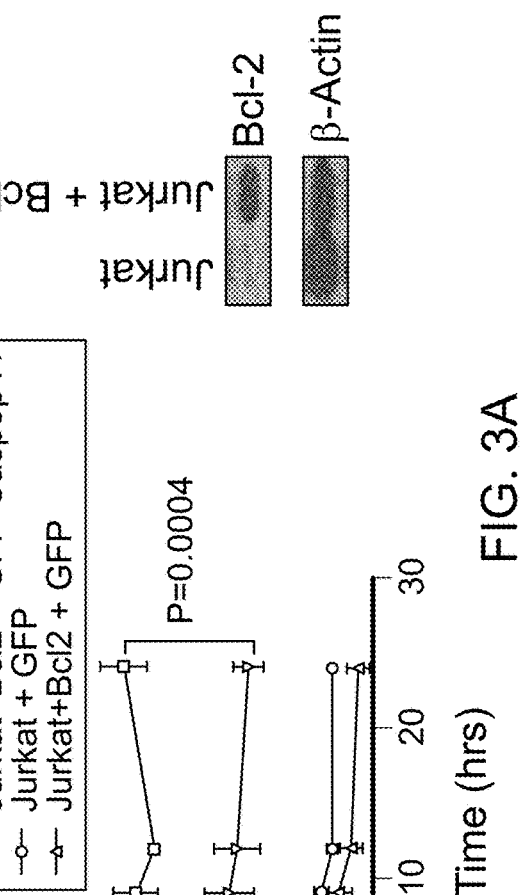
Figure 3A:
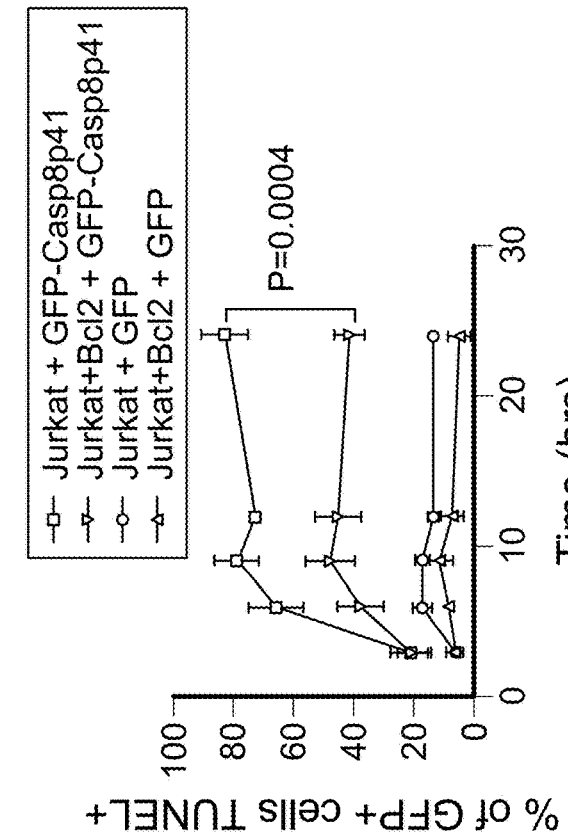
Figure 3D:
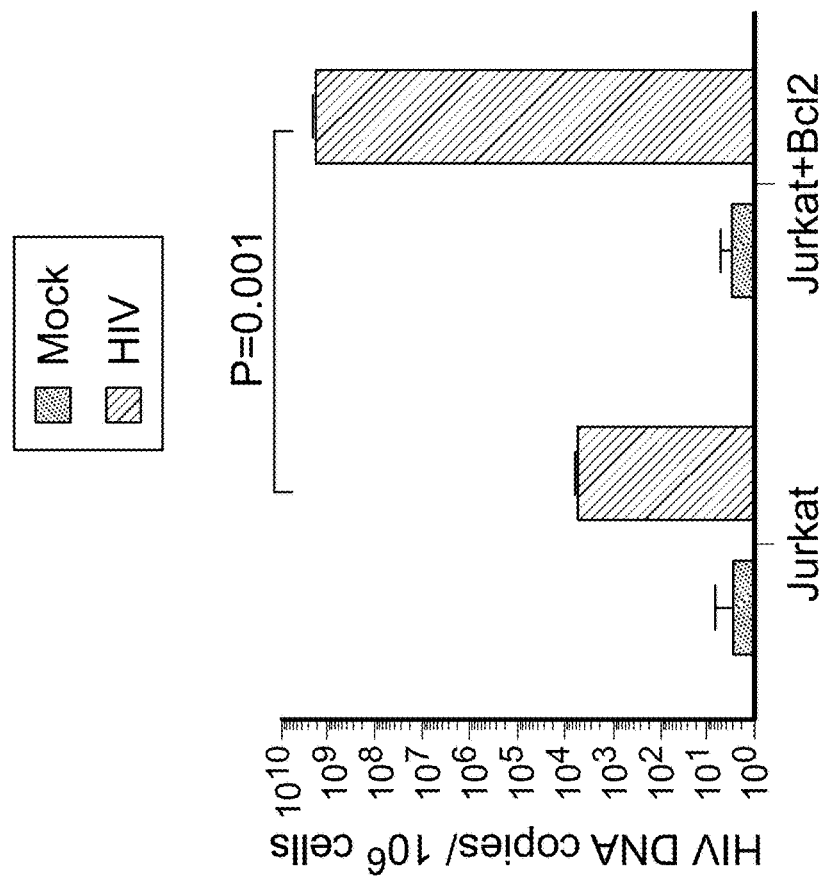
Figure 3C:
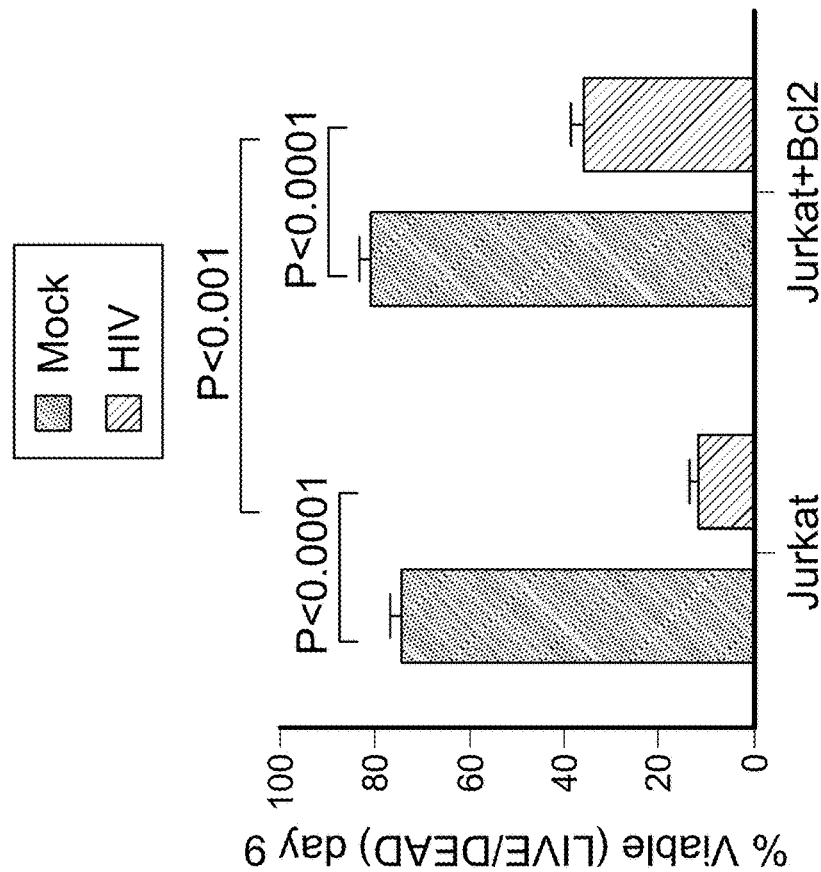
Figures 3E, 3F:
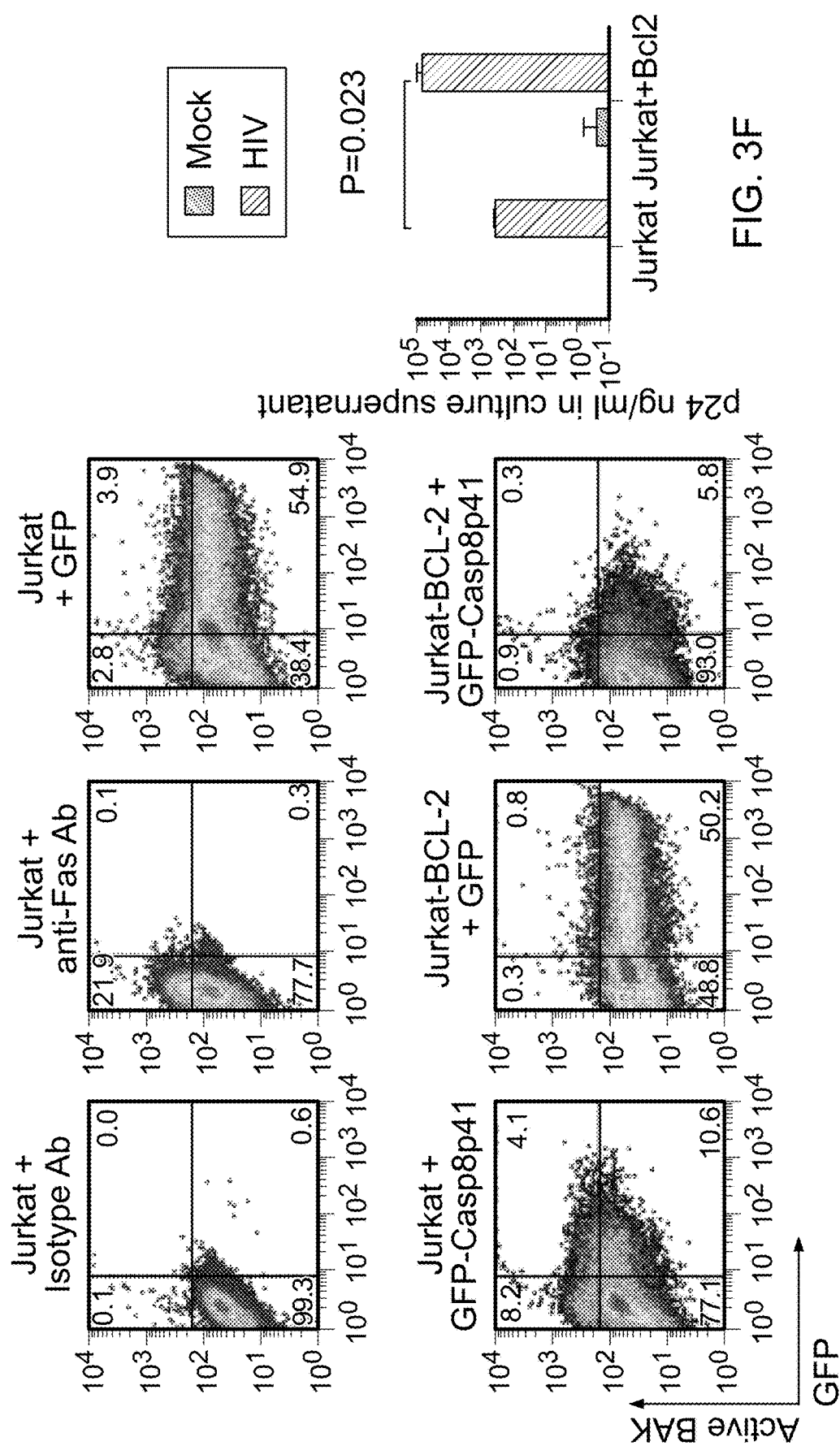
Figure 3G:
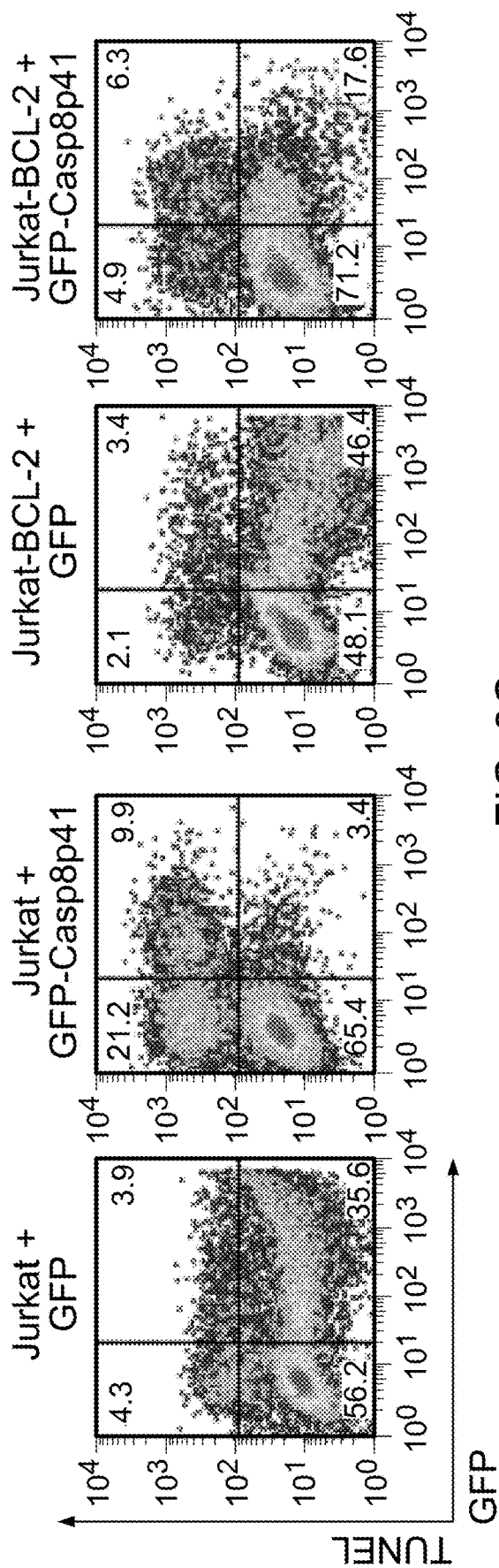
Figure 3H:
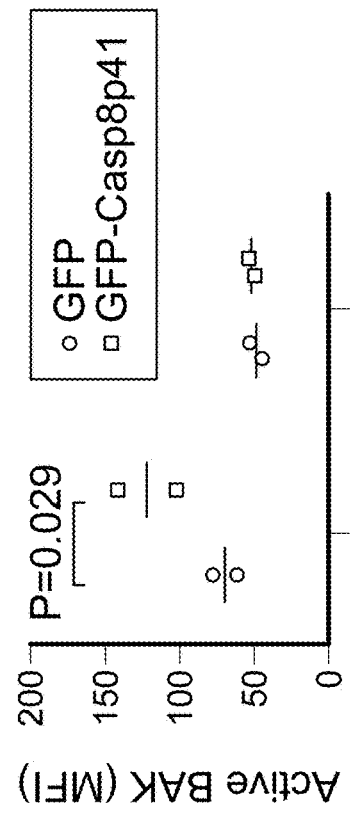

FIGS. 3A-3H. Bcl-2 overexpression decreases Casp8p41- or HIV-induced cell death while increasing viral replication. FIG. 3A, Parental Jurkat T cells or Jurkat cells stably overexpressing Bcl-2 were transfected with GFP-Casp8p41 or vector control and assessed for cell death via TUNEL. FIG. 3B, Relative GFP-Casp8p41 expression in EGFP$^+$ Jurkat and Jurkat/Bcl-2 cells. Cells infected with HIVIIIb or mock infected were assessed for viability by LIVE/DEAD stain (FIG. 3C), cell associated HIV DNA content (FIG. 3D), and HIV p24 production in culture supernatant (FIG. 3F), at day 9 post infection. Bars, mean±SD from 3 independent experiments. FIGS. 3H and 3E, Parental Jurkat cells or Jurkat-BCL-2 cells were transfected with GFP-Casp8p41 or GFP alone and assessed for active BAK expression in GFP positive cells, using a conformational specific antibody which detects only active BAK. Depicted are individual MFI of active BAK (FIG. 3H) and representative dot plots (FIG. 3E) from two independent experiments. FIG. 3F, Parental Jurkat cells or Jurkat-BCL-2 cells were infected with HIVIIIb or mock infected, and assessed for HIV p24 production in culture supernatant at day 9 post infection. Depicted are mean (SD) values of three independent experiments. FIG. 3G, Parental Jurkat T cells or Jurkat T cells stably overexpressing BCL-2 (Jurkat-BCL-2) were transfected with GFP-Casp8p41 or GFP alone and assessed for cell death via TUNEL.

Figure 4:
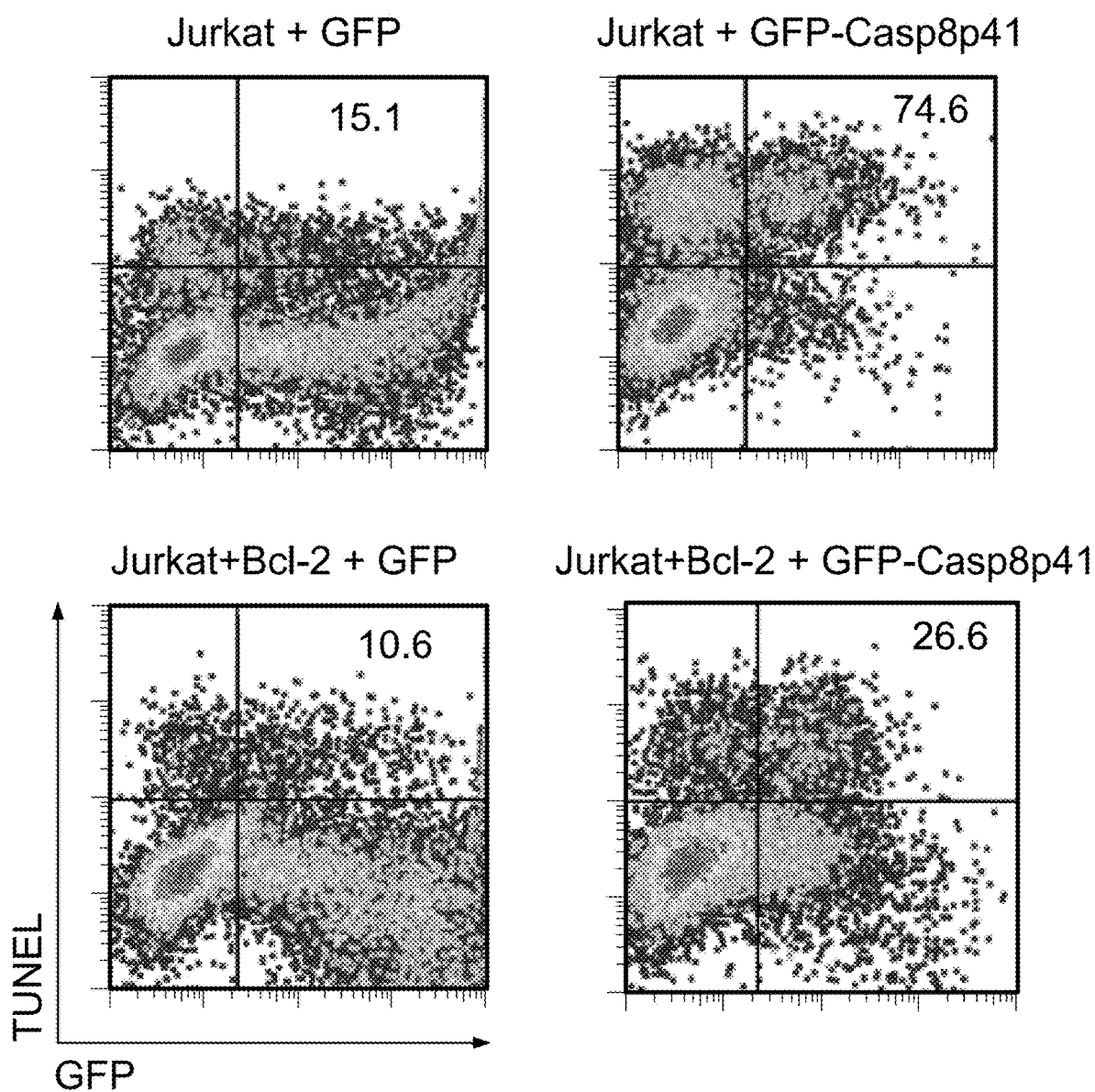

FIG. 4. Bcl-2 overexpression decreases TUNEL positivity induced by Casp8p41. Depicted is representative flow data from 6 hours post-transfection of parental Jurkat cells and Jurkat+Bcl-2 cells comparing TUNEL positivity in EGFP or EGFP-Casp8p41 expressing cells. Numbers depict the percent of GFP positive cells that are TUNEL positive.

Figure 5:
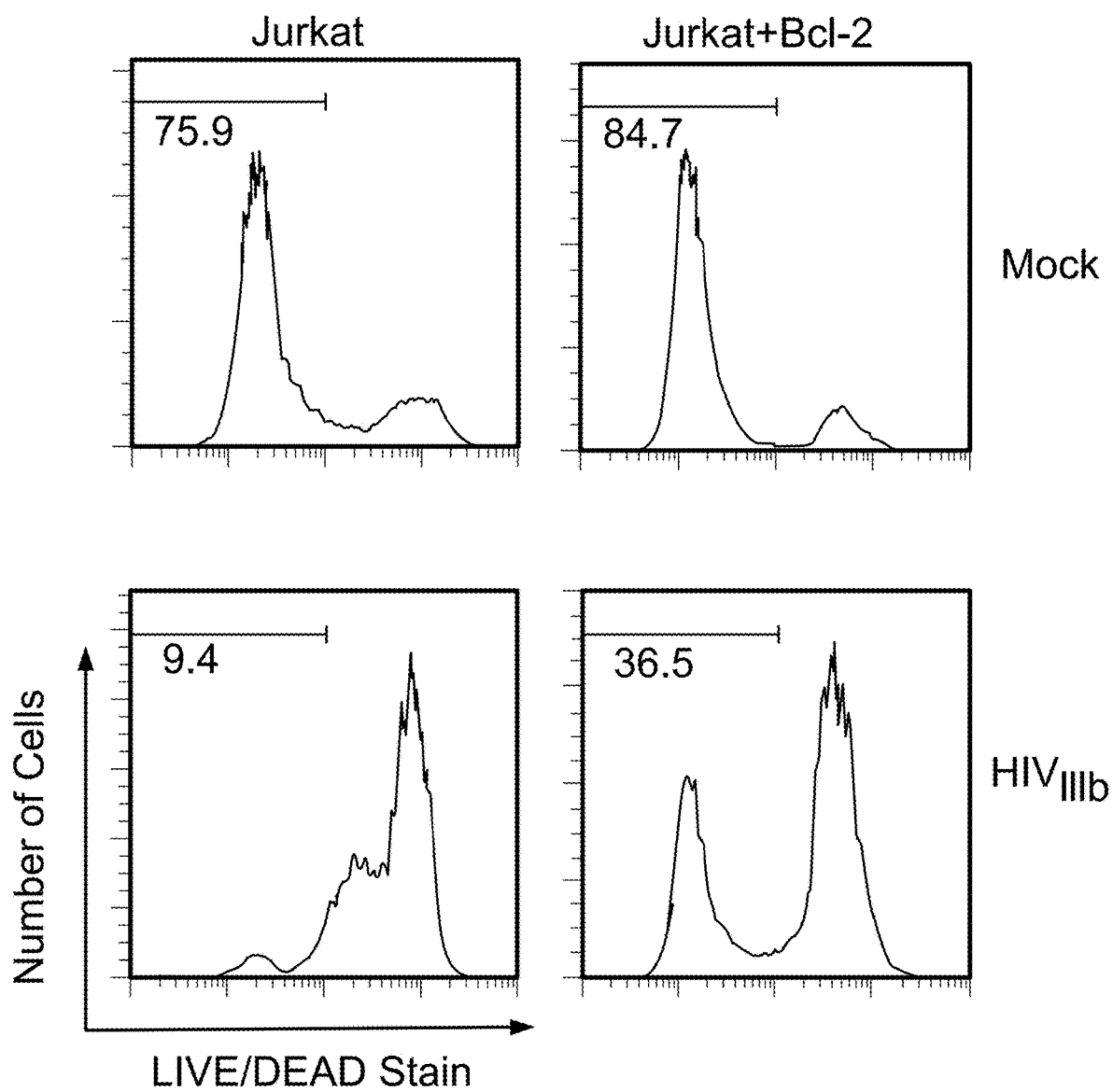

FIG. 5. Bcl-2 overexpression increases cell viability after in vitro HIV infection. Depicted is representative flow data assessing cell viability using LIVE/DEAD staining in parental Jurkat cells and Jurkat+Bcl-2 cells. Numbers depict percent of viable cells.

Figure 6A:
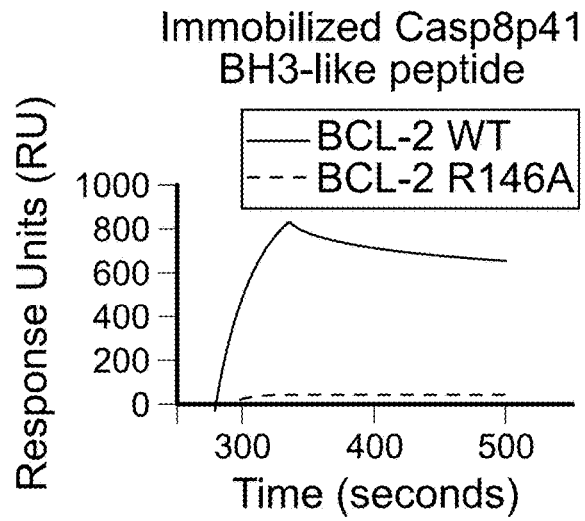
Figure 6B:
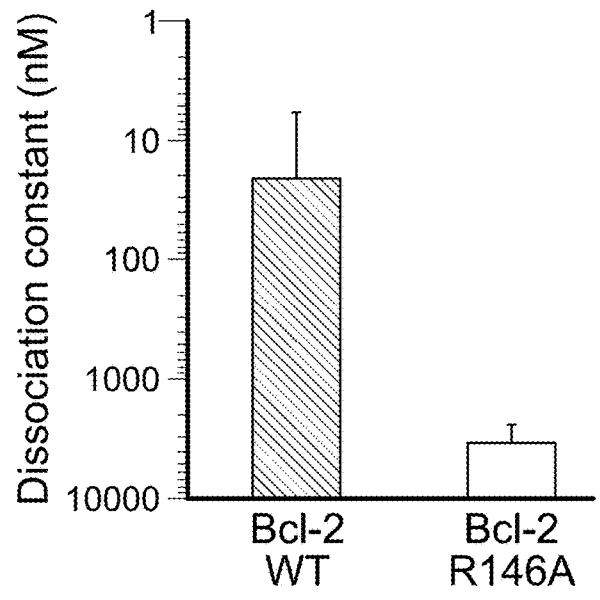

FIGS. 6A and 6B. Casp8p41 activator peptide binding to Bcl-2 is reduced by Arg146Ala substitution. FIG. 6A, Binding of 800 nM of GST-Bcl-2 or GST-Bcl-2 Arg146Ala to immobilized Casp8p41 activator peptide as assessed by SPR. FIG. 6B, Dissociation constants of GST-Bcl-2 and GST-Bcl-2 R146A to Casp8p41 activator peptide, from three independent experiments. ($P<0.05$).

Figure 7A:
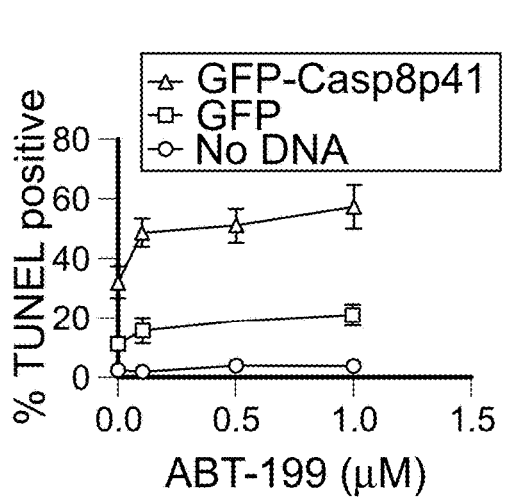
Figure 7B:
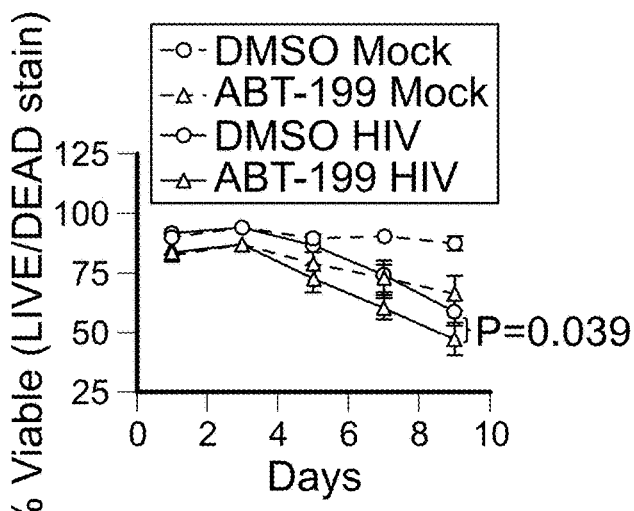
Figure 7C:
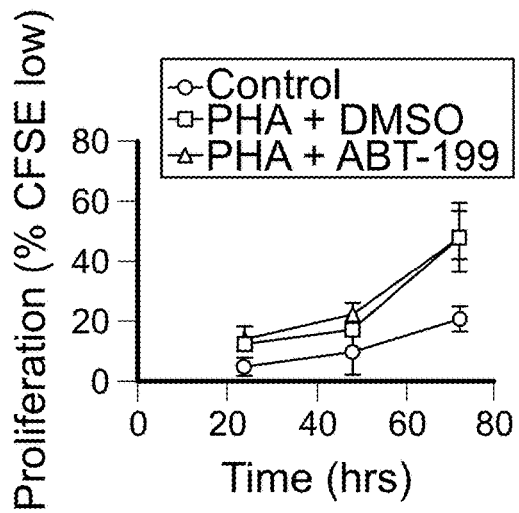
Figure 7D:
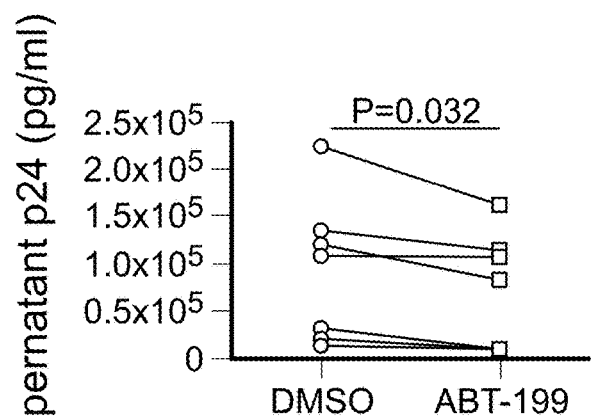
Figure 7E:
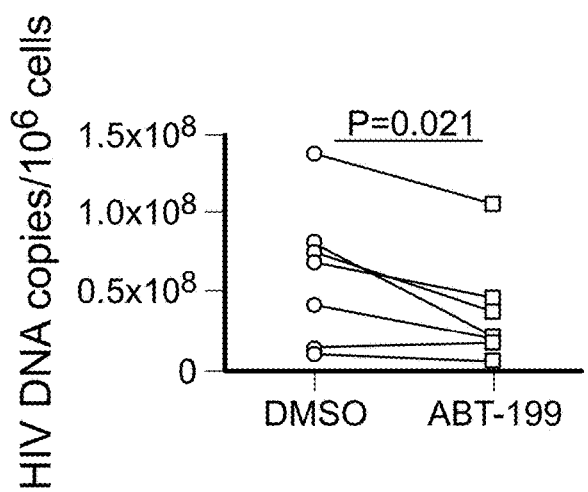
Figure 7F:
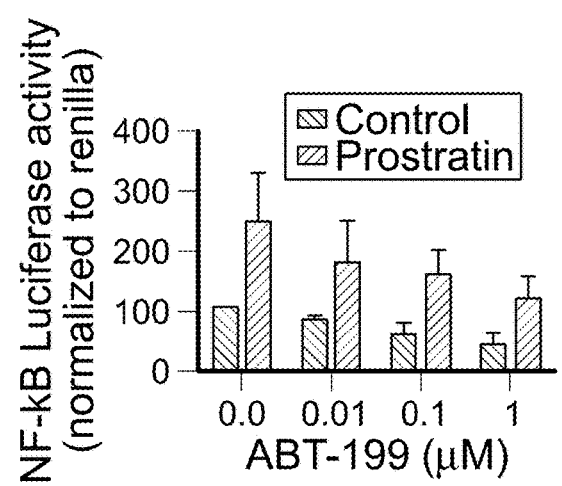
Figure 7G:
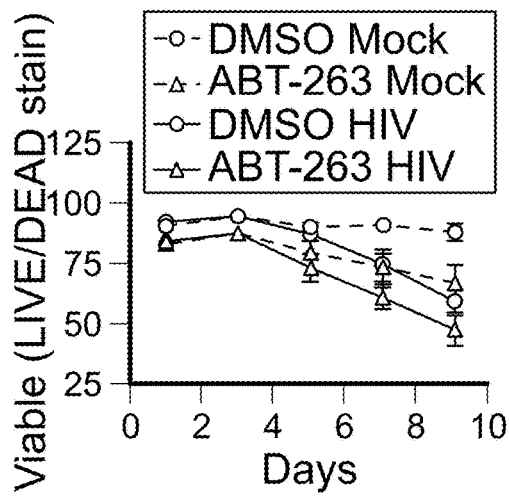
Figure 7H:
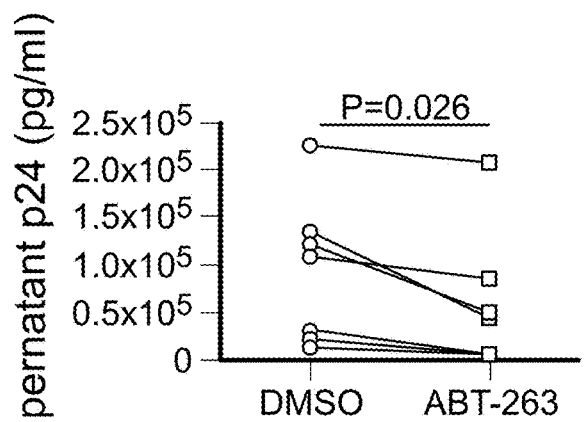
Figure 7I:
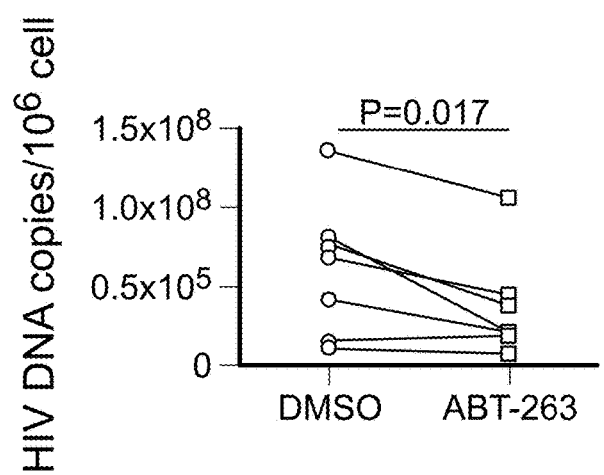

FIGS. 7A-7I. ABT-199 decreases infected cell survival, HIV replication, and cell associated HIV DNA during acute HIV infection in vitro. FIG. 7A, Jurkat T cells pretreated with DMSO or ABT-199 were transfected with EGFP-Casp8p41 or vector control and assayed for cell death by TUNEL. FIG. 7B, Primary CD4 T cells from 7 uninfected donors were infected with HIVIIIb or mock infected, treated with ABT-199 or diluent, and assayed for cell viability. FIG. 7C, Primary CD4 T cells were stimulated with phytohemagglutinin in the presence of ABT-199 or control and assayed for proliferation by CFSE staining. D, E, at day 9 post infection, HIV p24 concentrations in culture supernatant (FIG. 7D) and cell-associated HIV DNA (FIG. 7E), were measured. FIG. 7F, Primary CD4 T cells were transfected with an HIV LTR-luciferase reporter, treated with increasing concentrations of ABT-199, and stimulated with prostratin (1 µM). After overnight incubation, luciferase activities were measured. FIGS. 7G-7I, Primary CD4 T cells infected with HIV in the presence or absence of ABT-263 (1 µM) were assayed for viability (FIG. 7G), supernatant p24 production (FIG. 7H), and cell associated HIV-DNA (FIG. 7I). Bars: mean±SD of 4 (FIG. 7A) or 3 (other panels) independent experiments.

Figure 8:
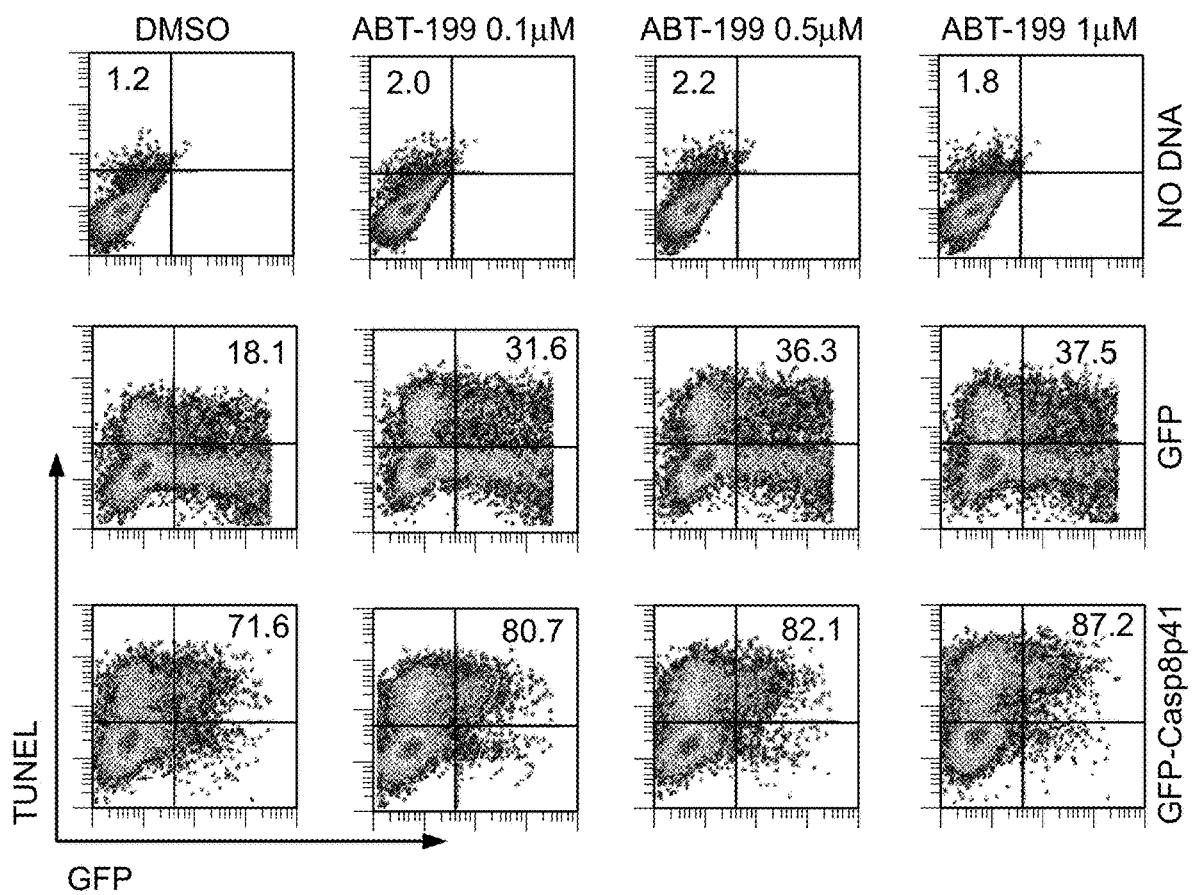

FIG. 8. ABT-199 increases Casp8p41-induced apoptosis. Depicted are representative dot plots assessing apoptosis as measured by TUNEL staining in Jurkat cells transfected with EGFP or EGFP-Casp8p41 and treated with diluent (DMSO) or increasing concentrations of ABT-199. Numbers depict the percent of EGFP positive (or total for No DNA) cells that are TUNEL positive.

Figure 9:
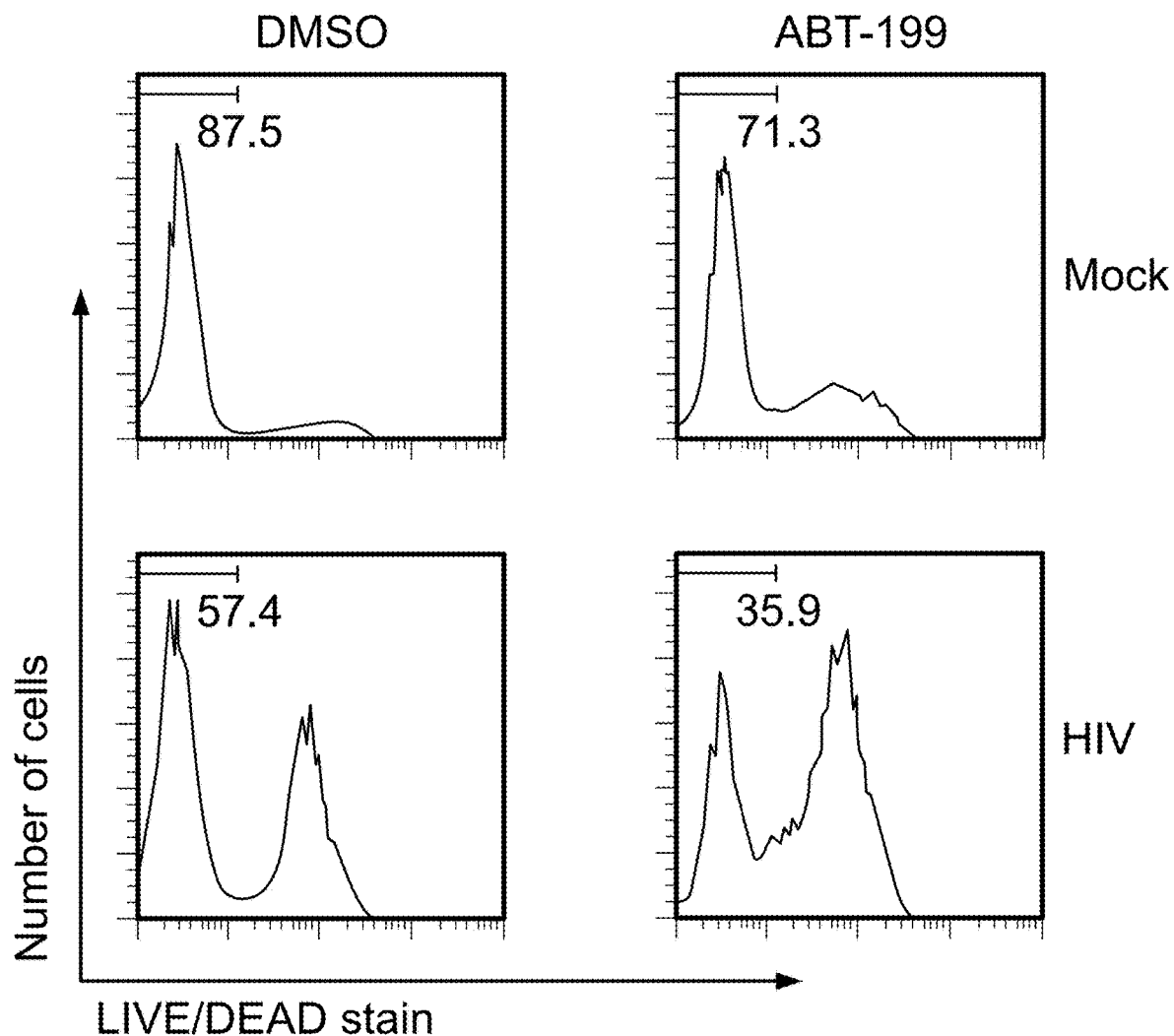

FIG. 9. ABT-199 decreases cell viability following acute HIV infection in vitro. Depicted is representative flow data assessing cell viability using LIVE/DEAD staining in primary CD4 T cells mock infected or HIV infected and treated with DMSO or ABT-199 at day 9 post-infection. Numbers depict the percent of cells that are viable.

Figure 10A:
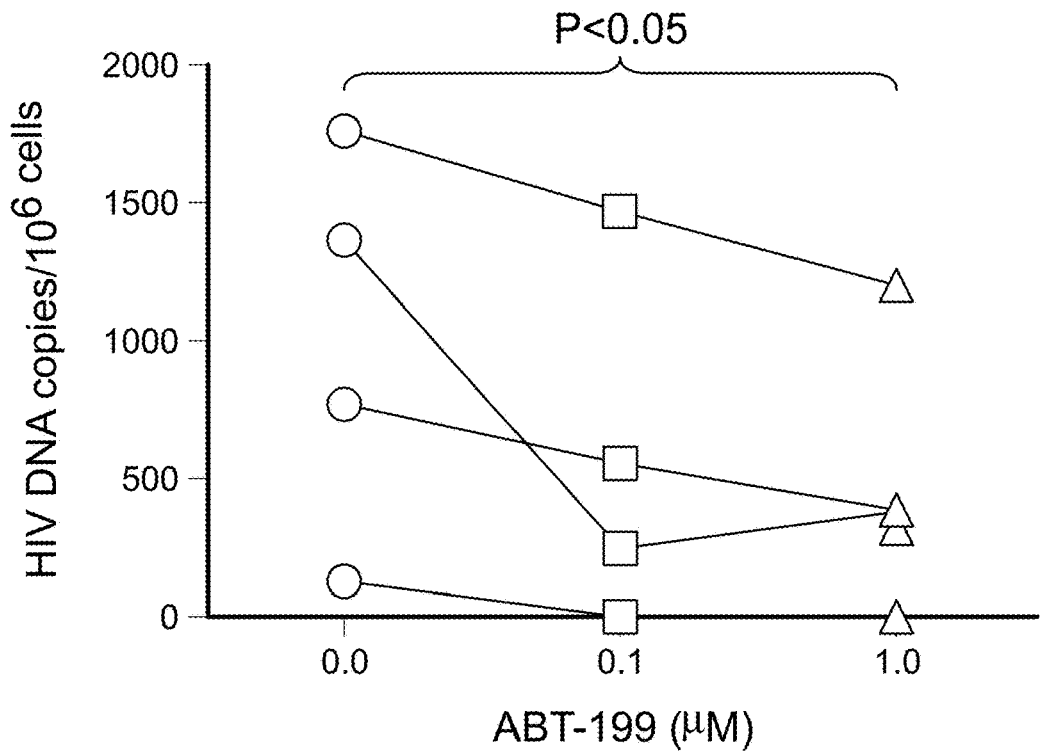
Figure 10B:
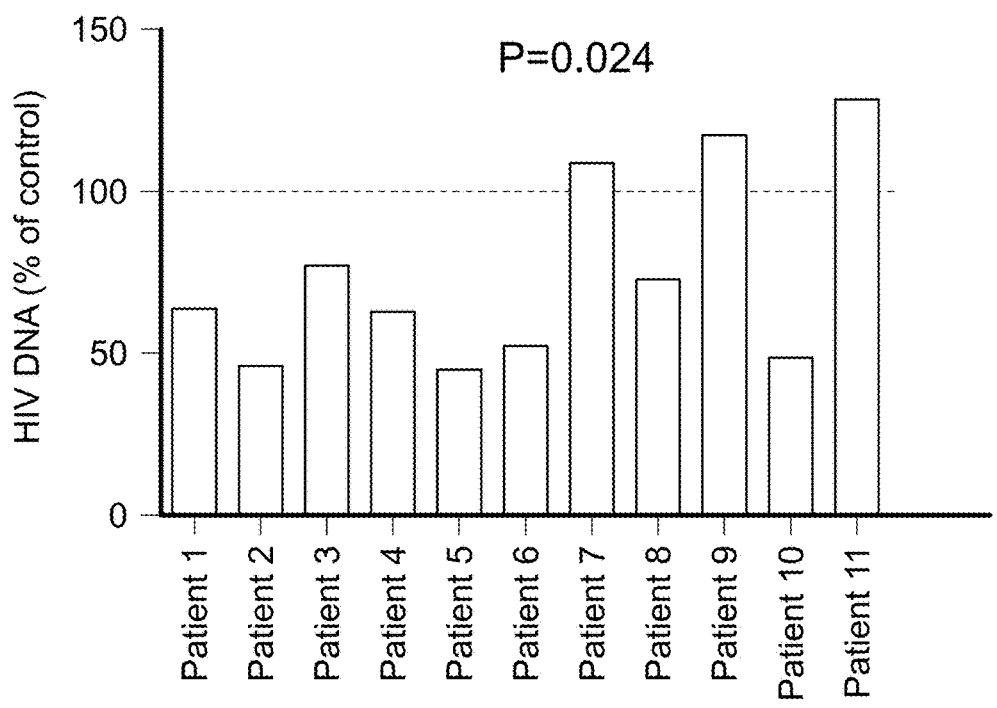
Figure 10C:
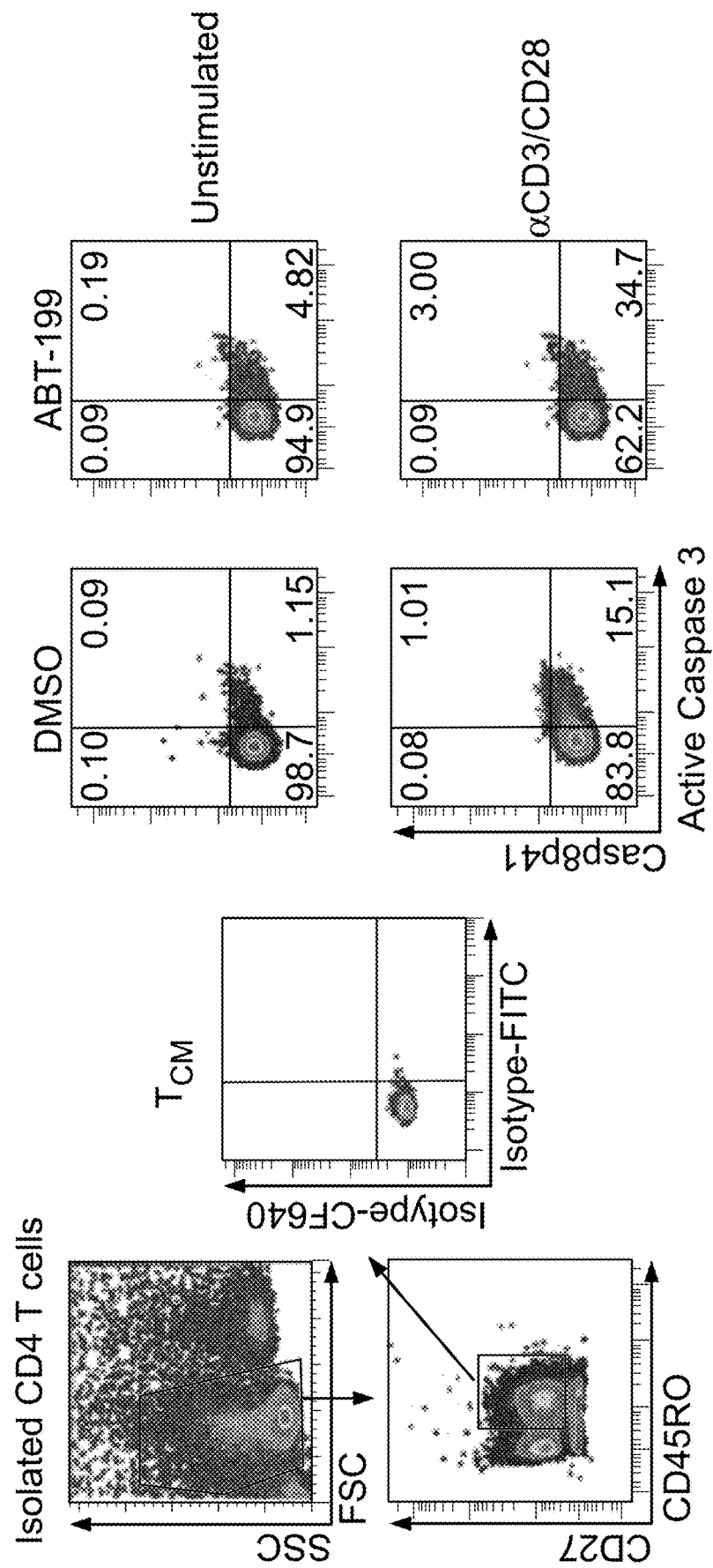
Figure 10D:
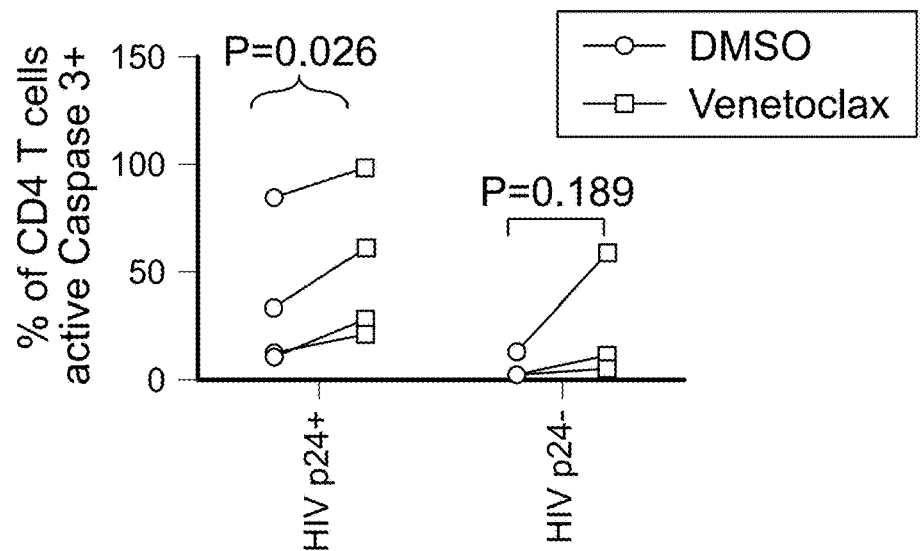
Figure 10D:
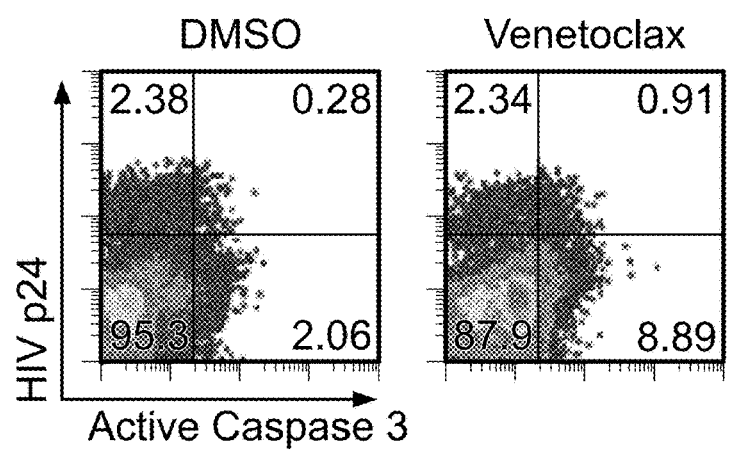
Figure 10E:
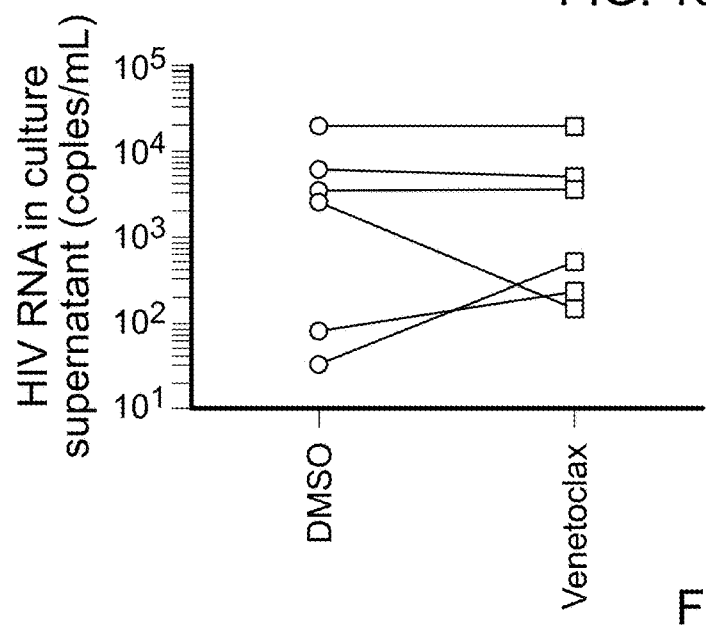

FIGS. 10A-10E. Selective Bcl-2 inhibition reduces HIV DNA associated with cells after viral reactivation ex vivo. FIG. 10A, Primary CD4 T cells isolated by negative selection from cryopreserved PBMCs of long-term virologically suppressed HIV-infected patients (N=4) were treated for 16 hours with ABT-199 or vehicle control in the presence of tenofovir and raltegravir, then exposed to plate bound αCD3 and soluble αCD28 antibody to induce HIV reactivation. After 72 hours, cell associated HIV DNA was measured. FIG. 10B, Freshly obtained peripheral CD4 T cells from an additional 16 suppressed HIV-infected patients were treated with ABT-199 or DMSO followed by αCD3/αCD28 for 72 hours before cell associated HIV DNA was measured. Depicted is the ratio of HIV DNA in ABT-199 treated vs. diluent treated samples for each patient with measurable HIV DNA in the diluent sample (n=11). FIG. 10C, Primary CD4 T cells from HIV-infected subjects were treated with ABT-199 or diluent and assayed for intracellular Casp8p41 and active caspase 3 in the $T_{CM}$ subset. Representative data of three independent subjects. FIG. 10D, Primary CD4 T cells from four HIV-infected subjects were treated with venetoclax or diluent and induced to reactivate HIV using CD3/CD28, and cell death measured in HIV P24 positive or negative cells using activated caspase 3 staining. FIG. 10E, HIV RNA was measured in cell culture supernatant from 6 of the 11 patient experiments from FIG. 10B.

Figure 11A:
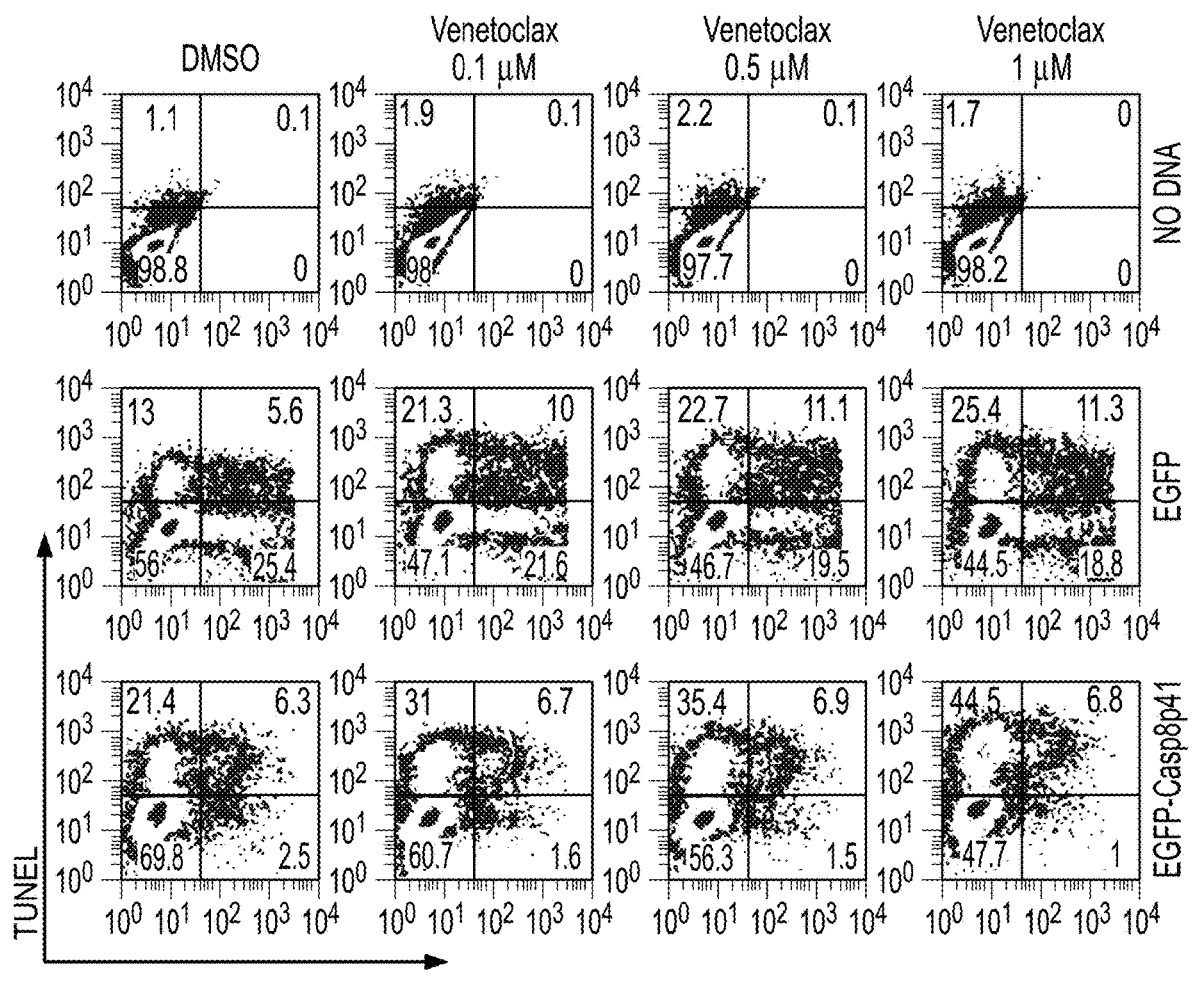
Figure 11B:
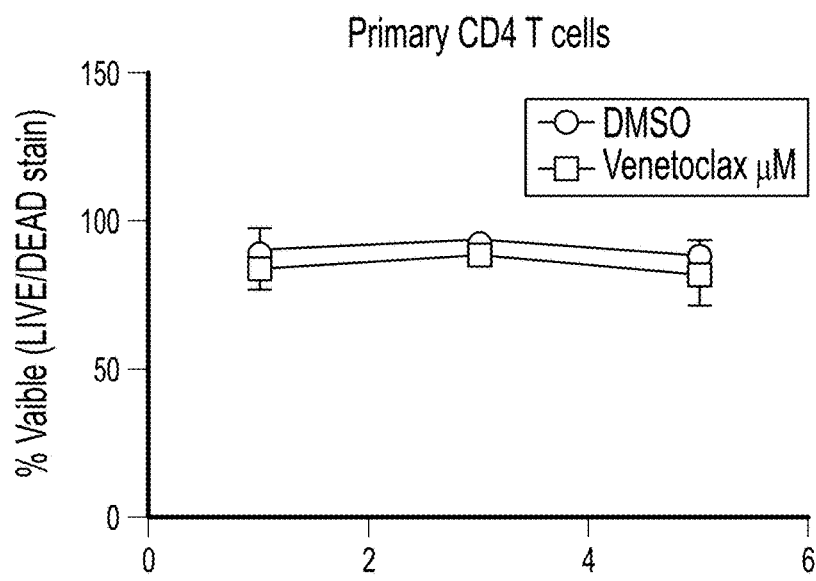
Figure 11C:
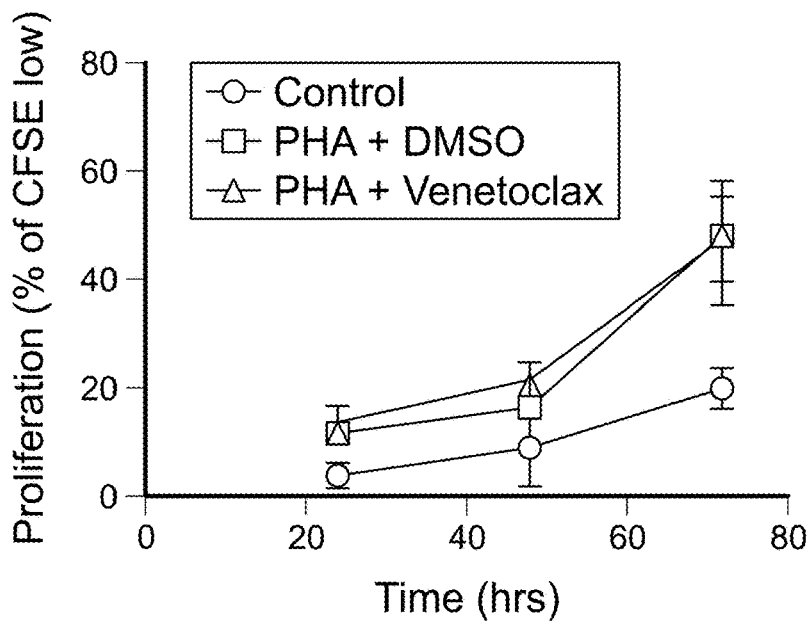
Figure 11D:
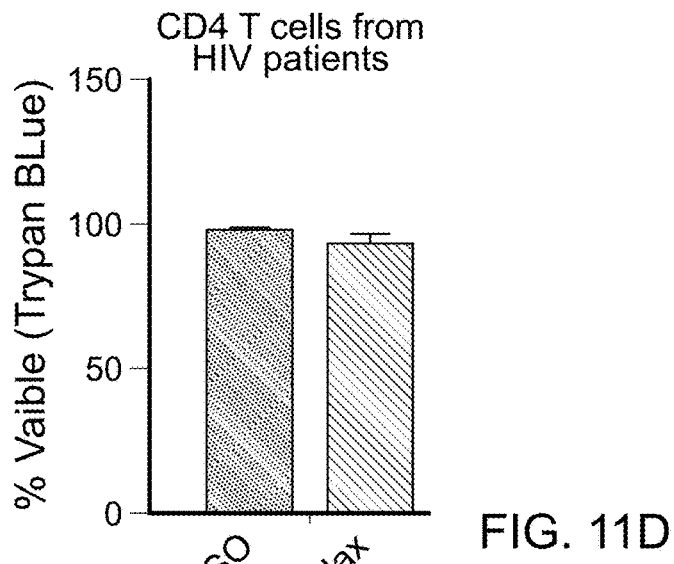

FIGS. 11A-11D. Venetoclax increases Casp8p41-induced apoptosis but spares cells that do not express Casp8p41. FIG. 11A, Jurkat T cells pretreated with increasing concentrations of venetoclax or diluent DMSO were transfected with EGFP-Casp8p41, vector control, or no DNA, and assayed for cell death by TUNEL. Data are representative of three independent experiments. FIG. 11B, Primary CD4 T cells from seven uninfected donors were treated with venetoclax (1 µM) or diluent, and assayed for cell viability by flow cytometry over 5 days. FIG. 11C, Primary CD4 T cells from four uninfected donors were stimulated with phytohemagglutinin (2 µg/mL) in the presence of venetoclax (1 µM) or diluent and assayed for proliferation by CFSE staining. FIG. 11D, Primary CD4 T cells from seven ART-suppressed HIV positive patients were treated with venetoclax (1 µM) or DMSO control for 24 hours and assessed for viability by trypan blue exclusion.

Figure 12A:
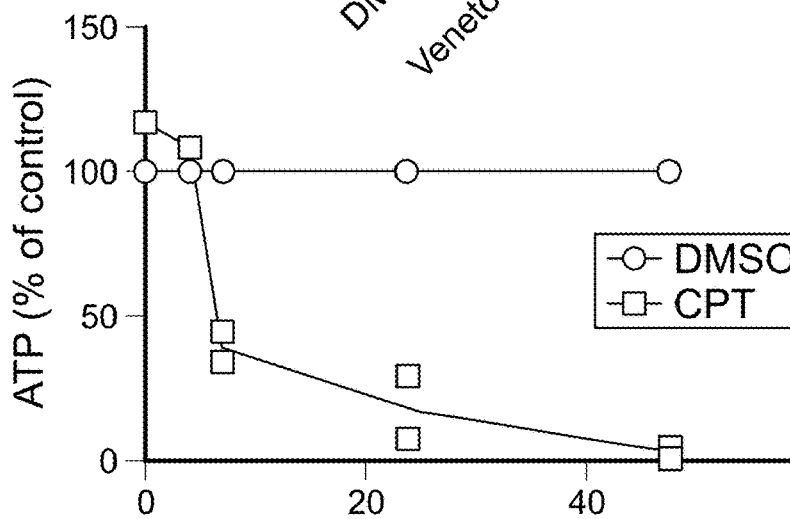
Figure 12B:
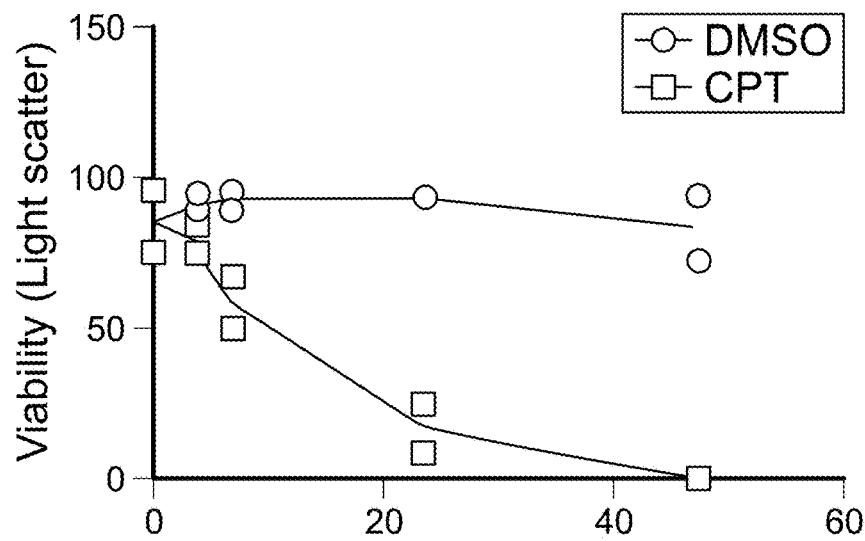
Figure 12C:
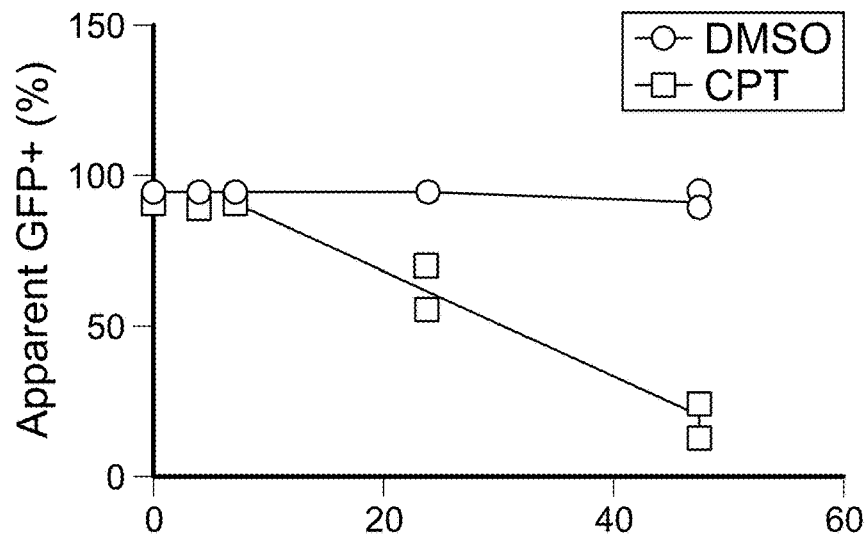
Figure 12D:
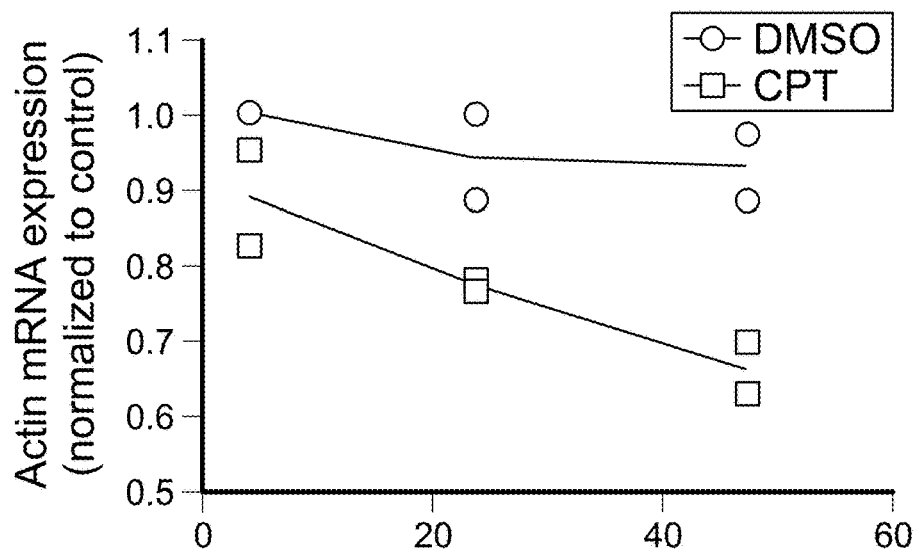

FIGS. 12A-12G. Apoptotic cell death is associated with loss of protein and mRNA markers. Jurkat T cells stably expressing eGFP were treated with DMSO or CPT and assessed for cell viability by ATP content (FIG. 12A) and light scatter (FIG. 12B) over time. FIG. 12C, Expression of eGFP was measured by flow cytometry. FIG. 12D, Actin mRNA expression was assessed by qRT-PCR and expressed as mean Ct values normalized to baseline DMSO control.

Figure 12E:
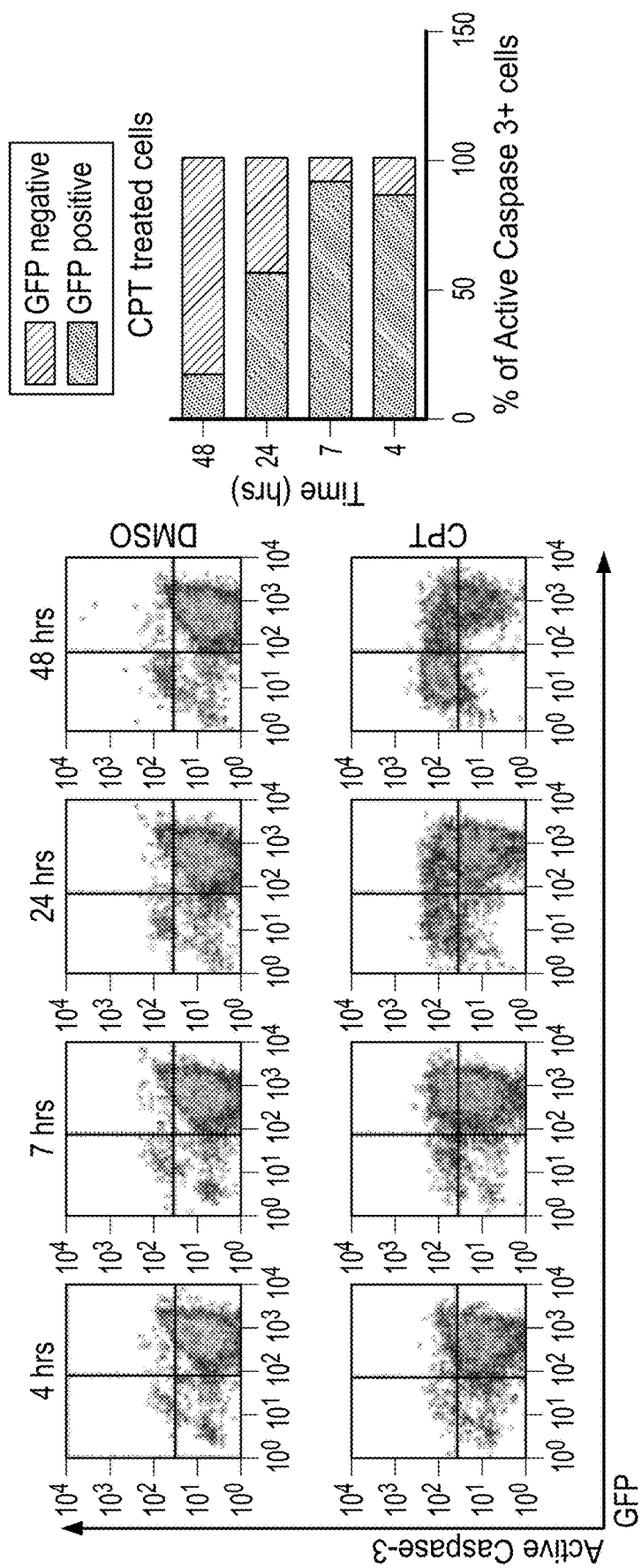
Figure 12F:
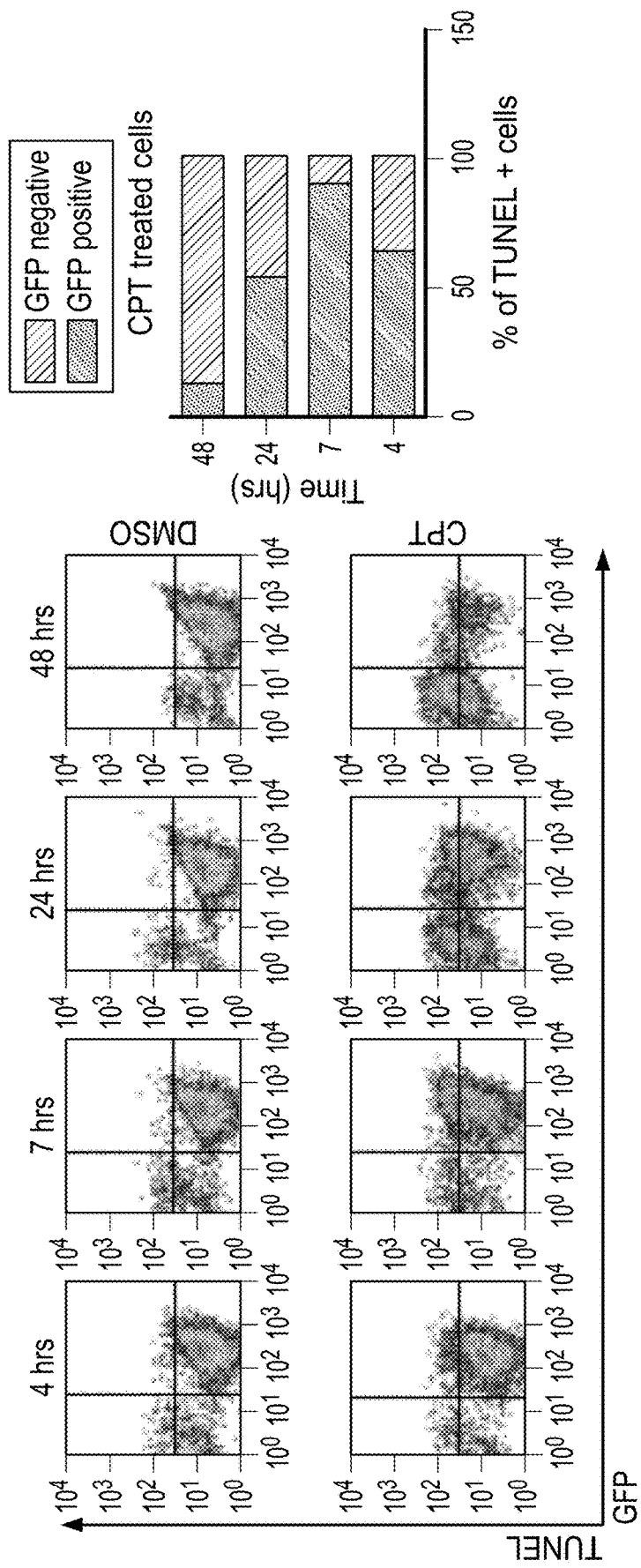
Figure 12G:
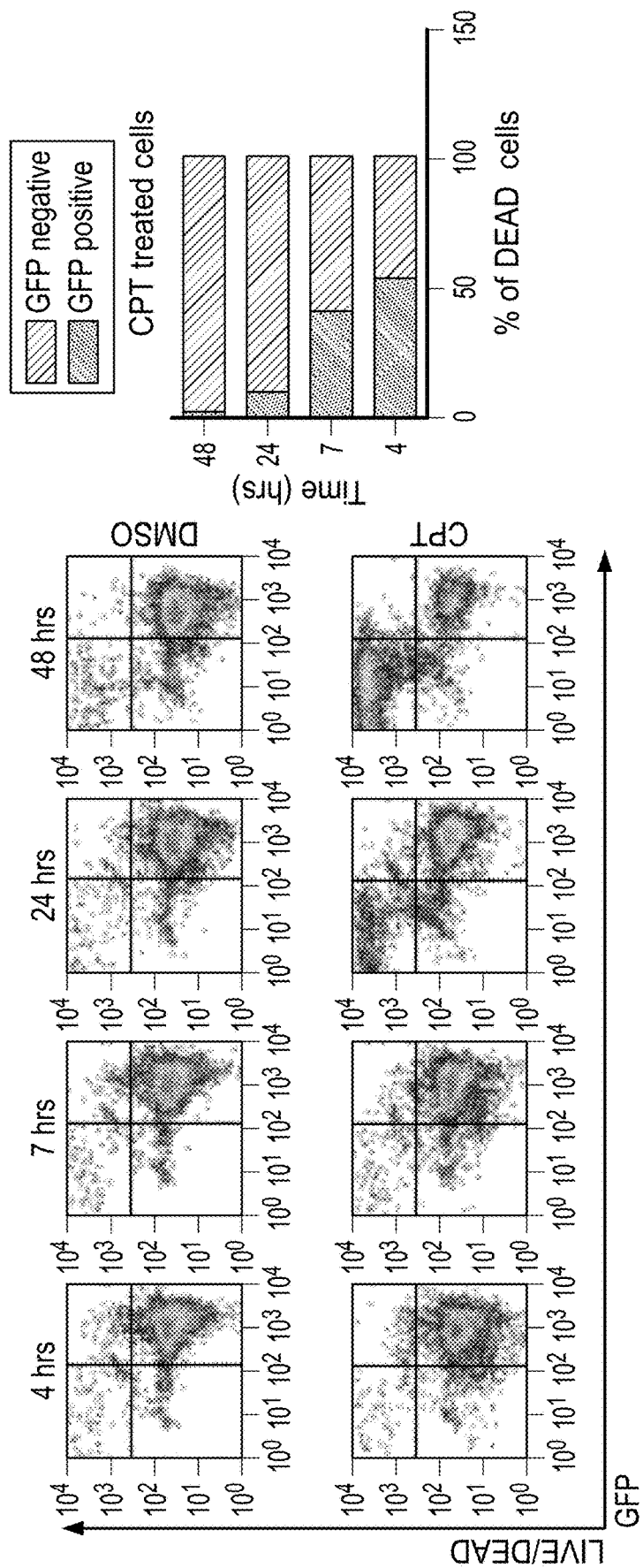

FIGS. 12E-12G, Cell death was assessed by active-caspase 3 expression (FIG. 12E), TUNEL (FIG. 12F), and LIVE/DEAD viability stain (FIG. 12G) and compared between eGFP positive and eGFP negative cells. FIG. 12A-12D values represent mean (range) of two independent experiments. FIGS. 12E-12G are representative of two independent experiments.

Figure 13A:
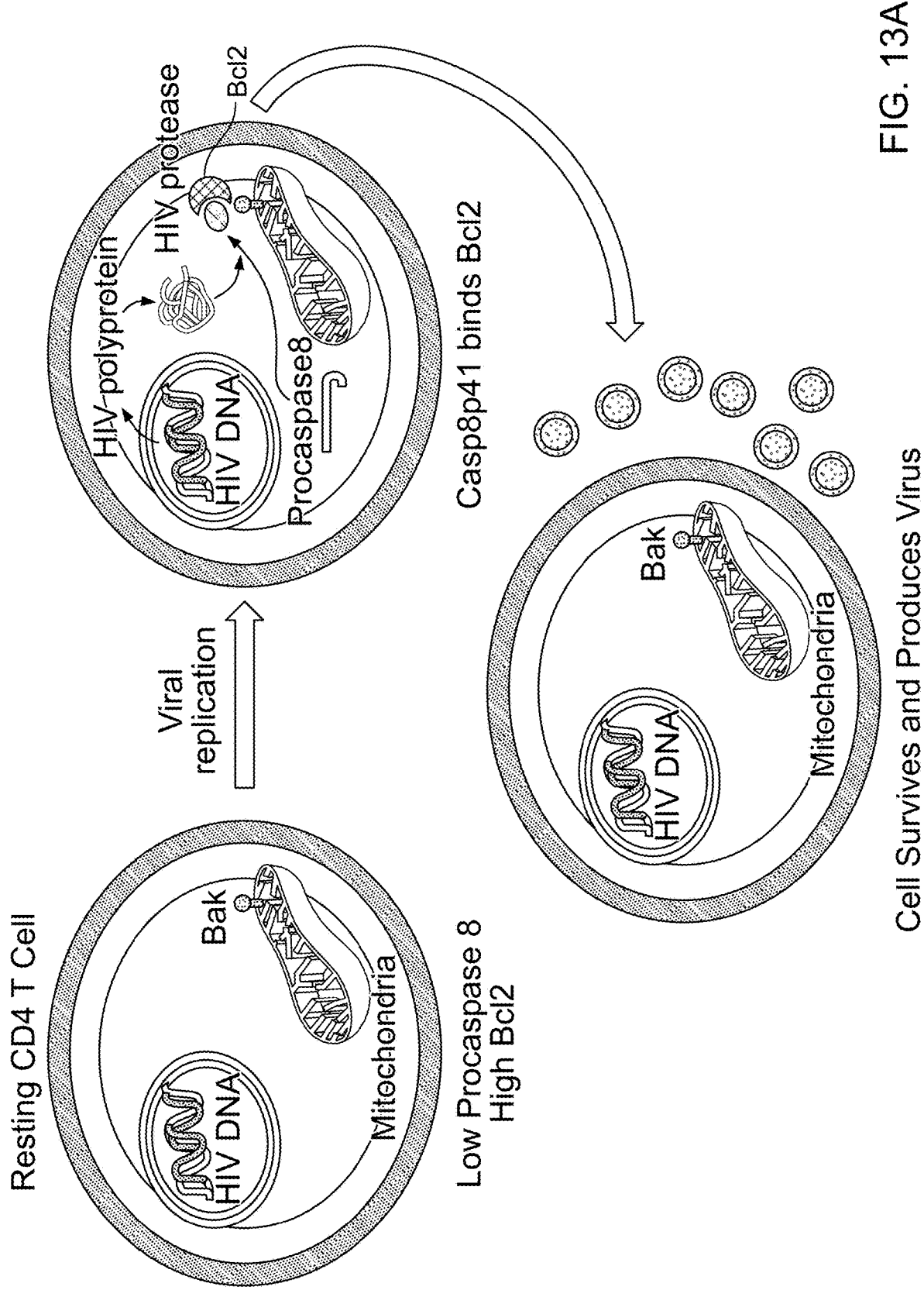
Figure 13B:
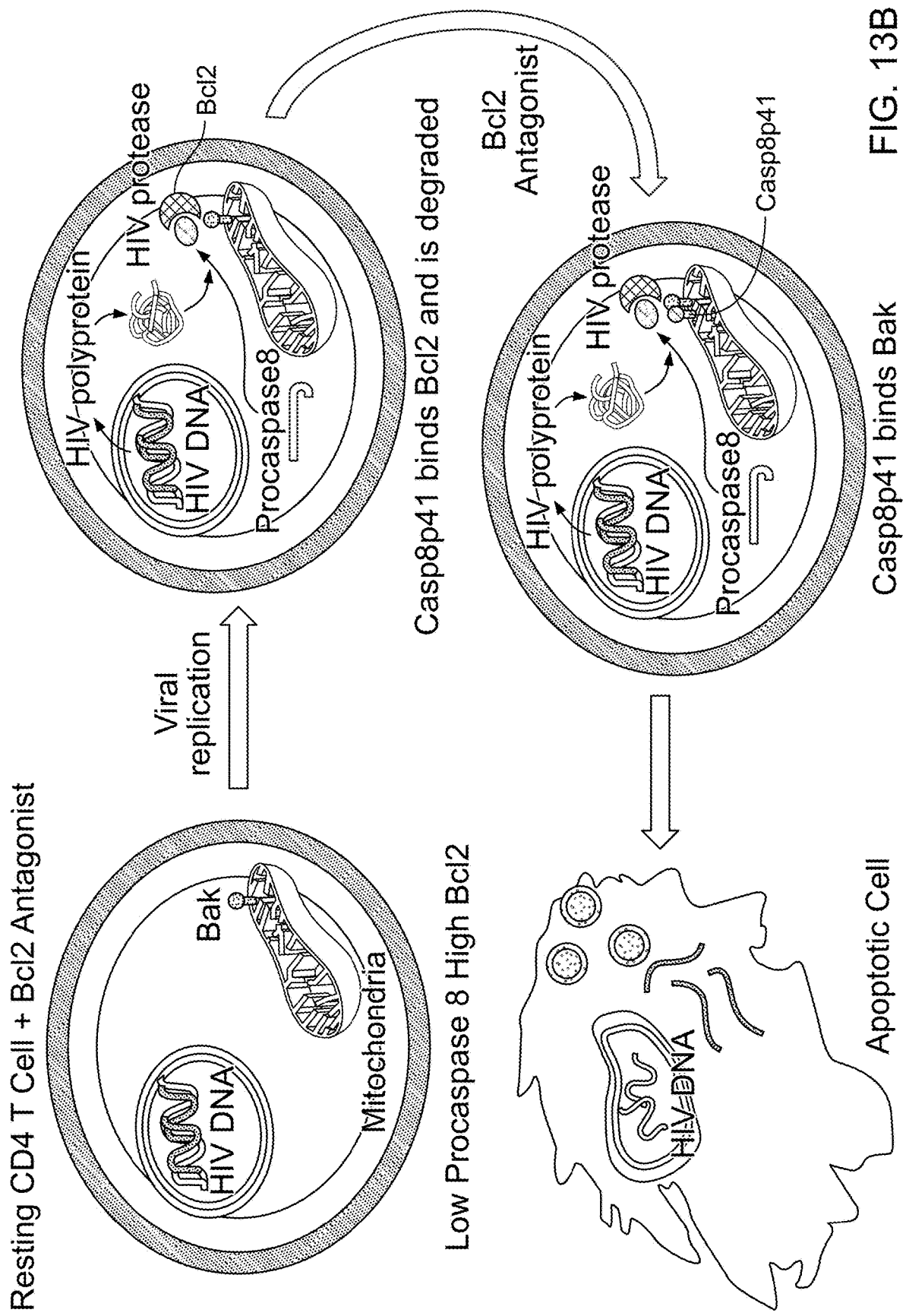

FIGS. 13A and 13B. BCL-2 antagonism as a model of "prime, shock and kill" for decreasing the HIV reservoir. FIG. 13A, Reactivation of latent HIV does not lead to death of the reactivated cell due to inhibition of Casp8p41 by direct binding to BCL-2. Therefore, the reactivated cell survives and produces progeny virus. FIG. 13B, Antagonism of BCL-2 activity (as with venetoclax treatment) allows Casp8p41 to bind pro-apoptotic BAK, leading to apoptotic death of the reactivated cell, and decreased total HIV DNA.

DETAILED DESCRIPTION

This document provides methods and materials for treating HIV infections. For example, this document provides methods and materials for using one or more Bcl-2 inhibitors alone or in combination with one or more other agents to treat HIV infections. In some cases, one or more Bcl-2 inhibitors can be used to cause latently HIV infected cells to die following HIV reactivation in those latently HIV infected cells.

Any appropriate method can be used to identify a human having an HIV infection. For example, HIV blood tests can be used to identify a human having an HIV infection.

Once identified as having an HIV infection, the human can be administered ART (e.g., maximally suppressive anti-retroviral therapy) to prevent or reduce the level of repopulation of the HIV reservoir and one or more Bcl-2 inhibitors to increase the susceptibility of latently HIV infected cells to cell death upon HIV reactivation and/or to kill HIV reactivating cells.

An ART can include any appropriate anti-retroviral agent or combination of anti-retroviral agents. Examples of anti-retroviral agents that can be used for ART include, without limitation, HIV integrase inhibitors, HIV protease inhibitors, and reverse transcriptase inhibitors. Examples of HIV integrase inhibitors include, without limitation, raltegravir (also known as Isentress or MK-0518), dolutegravir, and elvitegravir. Examples of HIV protease inhibitors include, without limitation, lopinavir and atazanavir. Examples of reverse transcriptase inhibitors include, without limitation, emtricitabine, rilpivirine, and tenofovir. In some cases, combinations of anti-retroviral agents can be formulated into a single dosage form (e.g., a single pill or capsule) such as Complera® (emtricitabine, rilpivirine, and tenofovir), Atripla® (efavirenz, emtricitabine, and tenofovir DF), Stribild® (cobicistat, elvitegravir, emtricitabine, and tenofovir), and Triumeq® (abacavir, dolutegravir, and lamivudine).

Any appropriate Bcl-2 inhibitor or combination of Bcl-2 inhibitors (e.g., a combination of two, three, four, five, or more different Bcl-2 inhibitors) can be used as described herein. Examples of Bcl-2 inhibitors that can be used as described herein include, without limitation, ABT-199, ABT263, and Sabutoclax.

In some cases, one or more agents that facilitate cell death by a Casp8p41 induced cell death pathway can be used in place of or in combination with one or more Bcl-2 inhibitors to treat HIV infections as described herein. For example, one or more agents that facilitate cell death by a Casp8p41 induced cell death pathway (e.g., SM164) can be used alone to treat HIV infections. Agents that facilitate cell death by a Casp8p41 induced cell death pathway include those that can increase caspase 8 polypeptide levels or can facilitate post mitochondrial death signaling. Examples of agents that can increase caspase 8 polypeptide levels include, without limitation, those agents that can increase caspase 8 polypeptide levels in CD4 T cells such as IL-2. Examples of agents that can facilitate post mitochondrial death signaling include, without limitation, SMAC mimetics such as LBW242, SM164, and Birinapant.

In some cases, one or more Bcl-2 inhibitors can be formulated into a pharmaceutically acceptable composition for administration to a human having an HIV infection. For example, a therapeutically effective amount of ABT-199 can be formulated together with one or more pharmaceutically acceptable carriers (additives) and/or diluents. A pharmaceutical composition can be formulated for administration in solid or liquid form including, without limitation, sterile solutions, suspensions, sustained-release formulations, tablets, capsules, pills, powders, and granules. A pharmaceutical composition containing one or more Bcl-2 inhibitors can be designed for oral or parenteral (including subcutaneous, intramuscular, intravenous, and intradermal) administration. When being administered orally, a pharmaceutical composition containing one or more Bcl-2 inhibitors can be in the form of a pill, tablet, or capsule. Compositions suitable for parenteral administration include aqueous and non-aqueous sterile injection solutions that can contain anti-oxidants, buffers, bacteriostats, and solutes which render the formulation isotonic with the blood of the intended recipient; and aqueous and non-aqueous sterile suspensions which may include suspending agents and thickening agents. The formulations can be presented in unit-dose or multi-dose containers, for example, sealed ampules and vials, and may be stored in a freeze dried (lyophilized) condition requiring only the addition of the sterile liquid carrier, for example water for injections, immediately prior to use. Extemporaneous injection solutions and suspensions may be prepared from sterile powders, granules, and tablets.

In some cases, a pharmaceutically acceptable composition including one or more Bcl-2 inhibitors can be administered systemically. For example, a composition containing a Bcl-2 inhibitor can be administered systemically orally or by injection to a human.

Effective doses can vary depending the route of administration, the age and general health condition of the human, excipient usage, the possibility of co-usage with other therapeutic treatments such as use of anti-retroviral agents and/or latency reversing agents, and the judgment of the treating physician.

An effective amount of a composition containing one or more Bcl-2 inhibitors can be any amount that increases the susceptibility of latently HIV infected cells to cell death upon HIV reactivation, thereby causing the latently HIV infected cells to die, without producing significant toxicity to the human. If a particular human fails to respond to a particular amount, then the amount of Bcl-2 inhibitor can be increased by, for example, two fold. After receiving this higher amount, the human can be monitored for both responsiveness to the treatment and toxicity symptoms, and adjustments made accordingly. The effective amount can remain constant or can be adjusted as a sliding scale or variable dose depending on the human's response to treatment. Various factors can influence the actual effective amount used for a particular application. For example, the frequency of administration, duration of treatment, use of multiple treatment agents, route of administration, and severity of the HIV infection may require an increase or decrease in the actual effective amount administered.

The frequency of administration of a composition containing one or more Bch 2 inhibitors can be any frequency that increases the susceptibility of latently HIV infected cells to cell death upon HIV reactivation, thereby causing the latently HIV infected cells to die, without producing significant toxicity to the human. For example, the frequency of administration can be from about daily to about once a week. The frequency of administration can remain constant or can be variable during the duration of treatment. As with the effective amount, various factors can influence the actual frequency of administration used for a particular application. For example, the effective amount, duration of treatment, use of multiple treatment agents, route of administration, and severity of the HIV infection may require an increase or decrease in administration frequency.

An effective duration for administering a composition containing one or more Bcl-2 inhibitors can be any duration that increases the susceptibility of latently HIV infected cells to cell death upon HIV reactivation, thereby causing the latently HIV infected cells to die, without producing significant toxicity to the human. Thus, the effective duration can vary from several months to several years. In general, the effective duration for the treatment of an HIV infection as described herein can range in duration from about two months to about five years. Multiple factors can influence the actual effective duration used for a particular treatment. For example, an effective duration can vary with the frequency of administration, effective amount, use of multiple treatment agents, route of administration, and severity of the HIV infection being treated.

In some cases, a human having an HIV infection can be treated with one or more Bcl-2 inhibitors as described herein in combination with (a) one or more anti-retroviral agents, (b) one or more latency reversing agents, (c) one or more immunotherapeutic agents, (d) one or more vaccines (e.g., a vaccine formulated for assisting in the treatment of an HIV infection), (e) one or more nucleic acid-based therapies, (f) one or more polypeptides designed to restrict HIV expression such as TRIMS alpha chimeric polypeptides, and (g) one or more advanced (e.g., third or later generation) chimeric antigen receptors expressed on CD8 T cells or NK cells designed to generate anti-HIV immunity. Examples of latency reversing agents that can be used in combination with one or more Bcl-2 inhibitors as described herein include, without limitation, HDAC inhibitors, phorbol esters, IL-2, bromodomain inhibitors, and those described elsewhere (Bullen et al., *Nature Medicine*, 20:425-429 (2014)). Examples of HDAC inhibitors that can be used as latency reversing agents include, without limitation, vorinostat, panabinostat, and valproic acid. Examples of phorbol esters that can be used as latency reversing agents include, without limitation, prostratin and PMA. An example of a bromodomain inhibitor that can be used as a latency reversing agent includes, without limitation, JQ1 ((S)-tert-butyl 2-(4-(4-chlorophenyl)-2,3,9-trimethyl-6H-thieno[3,2-f][1,2,4]triazolo[4,3-a][1,4]diazepin-6-yl)acetate).

Examples of immunotherapeutic agents that can be used in combination with one or more Bcl-2 inhibitors as described herein include, without limitation, IL-15, CD4 immunotoxin, and neutralizing anti-HIV antibodies. For example, a human having an HIV infection can be administered one or more Bcl-2 inhibitors as described herein and IL-15.

Examples of vaccines that can be used in combination with one or more Bcl-2 inhibitors as described herein include, without limitation, HIV tat or env antigens delivered by any number of platforms including genetic immunization, viral or virus like particle delivery, or delivery as recombinant proteins. The HIV antigens can be delivered with adjuvants such as CPG or GM-CSF. In some cases, a human having an HIV infection can be administered one or more Bcl-2 inhibitors as described herein and a HIV tat or env vaccine.

Examples of nucleic acid-based therapies that can be used in combination with one or more Bcl-2 inhibitors as described herein include, without limitation, nucleic acid molecules having the ability to reduce CCR5 polypeptide expression (e.g., siRNA molecules designed to reduce CCR5 polypeptide expression) and TALEN or CRISPR/Cas constructs designed to excise HIV DNA. For example, a human having an HIV infection can be administered one or more Bcl-2 inhibitors as described herein and an siRNA molecule designed to reduce CCr5 polypeptide expression.

In some cases, a human having an HIV infection can be treated with one or more Bcl-2 inhibitors as described herein in combination with one or more anti-retroviral agents plus any one or more of (a) one or more latency reversing agents, (b) one or more immunotherapeutic agents, (c) one or more vaccines (e.g., a vaccine formulated for assisting in the treatment of an HIV infection), and (d) one or more nucleic acid-based therapies.

In some cases, the level of HIV infected cells within a human being treated can be monitored during the course of treatment. Any appropriate method can be used to determine the level of HIV infected cells within a human. For example, the level of HIV infected cells within a human can be assessed using PCR based detection methods (nested or un-nested) for detecting HIV DNA, quantitative viral outgrowth assays (QVOA) for measuring replication competent HIV levels, or TILDA (Tat/rev; Induced Limiting Dilution Assay) that can measure the frequency of cells with multiply spliced HIV RNA as a surrogate for replication competent HIV.

The invention will be further described in the following examples, which do not limit the scope of the invention described in the claims.

EXAMPLES

Example 1—Bcl-2 Inhibition Facilitates Killing of HIV Infected Cells and Reduces Cell Associated HIV DNA Cell Culture Jurkat cells and HEK 293T cells were obtained from American Type Culture Collection (Manassas, Va.). Jurkat/Bcl-2 cells were created by transfecting Jurkat with a pcDNA-3 encoding Bcl-2 (obtained from Dr. Stan Korsmeyer), selecting for 30 days, and assessing Bcl-2 expression by immunoblotting. HIV-uninfected PBMCs were harvested by ficoll gradient centrifugation from Leukocyte Reduction System apheresis chambers provided by healthy volunteer blood donors. Primary bulk CD4 T cells were isolated using RosetteSep™ Human CD4$^+$ T Cell Enrichment Cocktail (StemCell Technologies), activated for 24 hours with 1 µg/mL phytohemagglutinin, washed in medium, and incubated for 48 hours with 50 units/mL IL-2 prior to HIV infection. TCM and TEM were treated with CH-11 anti-Fas antibody (1 µg/mL), cycloheximide (CHX, 30 µM), etoposide (20 µM), camptothecin (20 µM), carbonyl cyanide 3-chlorophenyl-hydrazone (CCCP, 1 μM), or $H_2O_2$ (0.35 mM) overnight to induce cell death.

Plasmid and Peptide Preparation

Casp8p41 in pEGFP, pcDNA3, and pGEX-4T were described elsewhere (Nie et al., Open Virol. J., 2:1-7 (2008); and Bren et al., PLoS One, 3:e2112 (2008)). Plasmids encoding Bcl-2, Bcl-xL, and Mcl-1 were described elsewhere (Smith et al., J. Biol. Chem., 286:17682-17692 (2011)). The indicated Casp8p41 and BCL-2 mutations were introduced using site-directed mutagenesis (Agilent Technologies, Santa Clara, Calif.) and confirmed by sequencing. The Casp8p41 BH3-like peptide (DMNLLDIFIEMEKR-VILGEGKLDILKRVCAQ; SEQ ID NO:1), N-terminal control peptide (MDFSRNLYDIGEQLDSEDLASLK; SEQ ID NO:2) and Bim BH3 peptide (Dai et al., J. Cell. Biol., 194:39-48 (2011)) were synthesized by solid phase synthesis.

Transfection

HEK 293T cells were transfected using Lipofectamine (Invitrogen, Carlsbad, Calif.) according to manufacturer's protocol. Jurkat cells were transfected using a square wave electroporator (BXT, San Diego, Calif.) at 320 V.

Immunoprecipitation and Immunoblotting 293T cells transfected with empty vector, HA-Casp8p41, or HA-Casp8p41EK were collected after 24 hours, washed with PBS, and lysed (20 mM Tris/HCl pH 7.5, 150 mM NaCl, 1% CHAPS, 2 μg/mL aprotinin, 10 μg/mL leupeptin, 2 μg/mL pepstatin, and 1 mM PMSF) for 10 minutes on ice and centrifuged at 15000 g for 5 minutes at 4° C. Aliquots containing 500 μg protein were precleared with 25 μL Protein A/G-agarose (Santa Cruz Biotechnology, Santa Cruz, Calif.), incubated with 5 μg anti-Bcl-2 clone C22 (Santa Cruz Biotechnology, Santa Cruz, Calif.) overnight at 4° C., supplemented with 10 μL Protein-A/G agarose. Beads were washed with lysis buffer 3 times in 10 fold the volume of the beads. Bound protein was eluted and subjected to SDS-PAGE followed by immunoblotting as described elsewhere (Sainski et al., J. Virol., 85:7965-7975 (2011)). Primary antibodies used were: anti-HA peroxidase high affinity 3F10 (Roche, St. Louis, Mo.) or anti-Bcl-2 clone C22, Mcl-1 clone 22, or Bcl-xL clone s18 (Santa Cruz Biotechnology, Santa Cruz, Calif.).

Protein Expression and Purification

After plasmids encoding GST tagged proteins were transformed into E. coli BL21 or DH5α by heat shock, bacteria were grown to an optical density of 0.8 and induced with 1 mM IPTG for 3 hours at 37° C. Bacteria were disrupted by freezing and thawing in calcium- and magnesium-free Dulbecco's phosphate buffered saline (PBS) containing 0.1% Triton X-100, 2 μg/mL aprotinin, 10 μg/mL leupeptin, 2 μg/mL pepstatin, and 1 mM PMSF, then sonicated three times for 15 sec/min on ice. GST-tagged proteins were purified with glutathione-agarose (Thermo Fisher Scientific, Rockford, Ill.).

Surface Plasmon Resonance (SPR)

Proteins for SPR were further purified by FPLC on Superdex 5200, concentrated in a centrifugal concentrator (Centricon, Millipore), dialyzed against Biacore buffer (10 mM HEPES (pH 7.4), 150 mM NaCl, 0.05 mM EDTA, and 0.005% (w/v) Polysorbate 20) and stored at 4° C. for <48 hours before use. Binding assays were performed at 25° C. on a Biacore 3000 biosensor after proteins were immobilized on a CMS chip (GE Healthcare). Ligands were injected at 30 μL/minute for 1 minute in Biacore buffer. Bound protein was allowed to dissociate in Biacore buffer at 30 μL/minute for 10 minutes and then desorbed with 2 M $MgCl_2$. Binding kinetics were derived using BIA evaluation software (Biacore, Uppsala, Sweden).

Flow Cytometry

Immunophenotyping of T cell subsets was performed using multicolor flow cytometry with monoclonal antibodies to human CD3 (Alexa700, BD Pharmingen), CD4 (FITC, BD Pharmingen), CD8 (Pacific Blue, BD Pharmingen), CD27 (PE, BD Pharmingen), and CD45RO (ECD, Beckman Coulter). Central memory T cells ($T_{CM}$) were defined as $CD3^+CD4^+CD27^+CD45RO^+$, and effector memory T cells ($T_{EM}$) were defined as $CD3^+CD4^+CD27^-CD45RO^{+/-}$ (Brenchley et al., J. Exp. Med., 200:749-759 (2004)). Intracellular expression of Casp8p41 was assessed as described elsewhere (Cummins et al., AIDS Res. Hum. Retroviruses, 30:476-479 (2014)). Cell death was measured using LIVE/DEAD® Fixable Aqua dead cell stain (Invitrogen) or TUNEL (Roche) according to manufacturers' protocols. Cell proliferation was measured using a CellTrace™ CFSE Cell Proliferation Kit (Life Technologies) according to manufacturer's protocol. FACS analysis was performed on either a FACScan or LSRII flow cytometer (BD Biosciences) based on multiparameter needs. FACS data were analyzed using FlowJo software (Tree Star Inc).

HIV Infections

Jurkat and Jurkat/Bcl-2 cells were infected overnight, while primary PHA-activated CD4 T cells were infected for 6 hours with HIV-1IIIb (NIH AIDS Reagent Program). Aliquots of the same infectious supernatant were used for all experiments. Cells were then washed three times and incubated in fresh medium. At the indicated time points, HIV-1 p24 in the cell culture supernatant was measured by RET-ROTEK™ ELISA kits (Zeptometrix Corporation) according to manufacturer's protocol. Cell associated HIV-1 DNA was assayed using a modification of the protocol described elsewhere (Liszewski et al., Methods, 47:254-260 (2009)). Briefly, total DNA was extracted using the Qiagen DNeasy Blood and Tissue kit (Hilden, Germany) and analyzed by a real-time polymerase chain reaction (PCR) assay specific for HIV-LTR and β-globin. A standard curve of pNL4-3 plasmid from $10^6$ through to 10 copies was used as an internal control. 300 nM of the sense primer RU5-F 5'-TTAAGCCT-CAATAAAGCTTGCC-3' (SEQ ID NO:3) and antisense primer RU5-R 5'-GTTCGGGCGCCACTGCTAGA-3' (SEQ ID NO:4) were used in conjunction with 300 nM dual-labeled fluorogenic TaqMan probe 5'-FAM-CCAGAGT-CACACAACAGACGG GCACA-TAMRA-3' (SEQ ID NO:5). For a 20 μL reaction, 10 μL of gene expression master mix (Applied Biosystems, Carlsbad, Calif.) was used with 5 μL of genomic DNA. PCR conditions involved one cycle of 95° C. for 3 minutes followed by 45 cycles of 95° C. for 15 seconds and 60° C. for 1 minute. Total HIV-1 DNA was compared and normalized with genomic DNA, determined by β-globin. HIV-1 proviral DNA levels were expressed as HIV-1 copies/β-globin genomic equivalent of $10^6$ cells.

Next Generation Sequencing

Primary $T_{CM}$ and $T_{EM}$ were isolated using $CD4^+$ Central Memory T Cell Isolation and $CD4^+$ Effector Memory T Cell Isolation Kits (MACS Miltenyi Biotec). After RNA was extracted (Qiagen RNA easy kit), the quality of total RNA samples was assessed by Agilent Bioanalyzer (Santa Clara, Calif.). RNA libraries were prepared according to the manufacturer's instructions for the TruSeq RNA Sample Prep Kit v2 (Illumina, San Diego, Calif.). Poly-A mRNA was purified from total RNA using oligo dT magnetic beads. The purified mRNA was fragmented at 95° C. for 8 minutes, eluted from the beads, and primed for first strand cDNA synthesis. The RNA fragments were then copied into first strand cDNA using SuperScript III reverse transcriptase and random primers (Invitrogen, Carlsbad, Calif.). Second strand cDNA synthesis was performed using DNA polymerase I and RNase H. The double-stranded cDNA was purified using a single AMPure XP bead (Agencourt, Danvers, Mass.) cleanup step. cDNA ends were repaired and phosphorylated using Klenow, T4 polymerase, and T4 polynucleotide kinase followed by a single AMPure XP bead clean-up. The blunt-ended cDNAs were modified to include a single 3' adenylate (A) residue using Klenow exo- (3' to 5' exo minus). Paired-end DNA adaptors (Illumina) with a single "T" base overhang at the 3' end were ligated to the 'A tailed' cDNA population. Unique indexes, included in the standard TruSeq Kits (12-Set A and 12-Set B) were incorporated at the adaptor ligation step for multiplex sample loading on the flow cells. The resulting constructs were purified by two consecutive AMPure XP bead clean-up steps. The adapter-modified DNA fragments were then enriched by 12 cycles of PCR using primers included in the Illumina Sample Prep Kit. Libraries were loaded onto paired end flow cells at concentrations of 8-10 pM to generate cluster densities of 700,000/mm$^2$ following Illumina's standard protocol using the Illumina cBot and cBot Paired end cluster kit version 3. The flow cells were sequenced as 51×2 paired end reads on an Illumina HiSeq 2000 using TruSeq SBS sequencing kit version 3 and HCS v2.0.12 data collection software. Basecalling was performed using Illumina's RTA version 1.17.21.3. Data were analyzed according to a Mayo Clinic developed protocol for analyzing RNA-Sequencing data (see, e.g., the World Wide Web at "biomedcentral.com/content/pdf/1471-2105-15-224.pdf").

Once the gene counts were provided by MAP-RSeq, a differential expression and gene set enrichment analysis was performed. DESeq33, an r package, was used to normalize and quantify log fold change, p-values, and the false discovery rate between the groups. A hypergeometric test was then performed on all targets with an absolute log 2 fold change of greater than 1 to investigate enrichment of genes associated with cell death and cell proliferation. Cell death and cell proliferation genes were gathered from DeathBase (Diez et al., Cell Death Differ., 17:735-736 (2010), Gene Ontology (Ashburner et al., Nat. Genet., 25:25-29 (2000), and KEGG pathways (Kanehisa and Goto, Nucleic Acids Res., 28:27-30 (2000)).

Statistical Analysis

Mean values of experimental results were compared by t-tests (non-paired for transformed cell line experiments, and paired for primary cell experiments) or ANOVA or Friedman tests as appropriate. Results of time course experiments were compared by area under the curve analyses, with mean AUC values compared by t-tests. P<0.05 considered statistically significant.

Molecular Modeling

The initial structure of the Casp8p41•Bcl-2 complex was generated by manually docking the activator domain of Casp8p41 (residues 142-162) in the α-helical conformation into the vacated BH3-binding groove of Bcl-2 (residues 50-203) that was taken from the crystal structure of human Bcl-2 (Protein Data Bank ID: 4AQ3; residue 9 of the 4AQ3 structure corresponds to residue 50 of the human Bcl-2 sequence of NCBI Accession ID of P10415). This manual docking placed V150$^{Casp8p41}$ in the proximity of L137$^{Bcl-2}$ and L157$^{Casp8p41}$ close to V148$^{Bcl-2}$. All Glu, Asp, Arg, and Lys residues were treated as GLU, ASP, ARG, and LYS, respectively. His94$^{Bcl-2}$ was treated as HIE, and all other His residues were treated as HIP. The topology and coordinate files of the complex were generated by using LEAP of AmberTools 1.5 (University of California, San Francisco). The complex was refined by energy minimization using SANDER of AMBER 11 (University of California, San Francisco) with a dielectric constant of 1.0 and 200 cycles of steepest-descent minimization followed by 300 cycles of conjugate-gradient minimization using AMBER forcefield FF12MC. Developed by Yuan-Ping Pang, FF12MC is based on AMBER forcefield FF99 with changes of (i) reducing all atomic masses by tenfold to improve configurational sampling (Pang, Biochem. Biophys. Res. Commun., 452: 588-592 (2014)), (ii) shortening C—H bonds by 10-14% (1.09 Å to 0.98 Å for the aliphatic; 1.08 Å to 0.93 Å for the aromatic) (Pang, Biochem. Biophys. Res. Commun., 458:352-355 (2015)), and (iii) zeroing torsion potentials involving a nonperipheral sp3 atom with reduction of the 1-4 interaction scaling factors of protein backbone torsions φ and ψ (from 2.00 to 1.00 for the van der Waals interaction; from 1.20 to 1.18 for the electrostatic interaction) (Pang, Biochem. Biophys. Res. Commun., 457: 183-186 (2015)). The energy minimized complex was then solvated by using the LEAP module with 5946 TIP3P water molecules with the distance parameter of 8.2 Å for the solvatebox command. The solvated complex system was energy-minimized for 100 cycles of steepest-descent minimization followed by 900 cycles of conjugate-gradient minimization to remove close van der Waals contacts in the system, then heated from 0 to 300 K at a rate of 10 K/ps under constant temperature and constant volume, and finally simulated in ten unique, independent 10-ns molecular dynamics simulations using PMEMD of AMBER 11 with FF12MC. The ten unique seed numbers for initial velocities of Simulations 1-10 are 1804289383, 846930886, 1681692777, 1714636915, 1957747793, 424238335, 719885386, 1649760492, 596516649, and 1189641421, respectively. These all-atom, isothermal-isobaric MD simulations used (i) a dielectric constant of 1.0, (ii) the Berendsen coupling algorithm (Berendsen et al., J. Chem. Phys., 81:3684-3690 (1984)), (iii) the Particle Mesh Ewald method to calculate long-range electrostatic interactions (Darden et al., J. Chem. Phys., 98:10089-10092 (1993), (iv) a time step of 1.0 fs, (v) SHAKE-bond-length constraints applied to all the bonds involving the H atom, (vi) a protocol to save the image closest to the middle of the "primary box" to the restart and trajectory files, (vii) a formatted restart file, (viii) a non-bonded cutoff of 8.0 Å, and (ix) default values of all other inputs of PMEMD. All simulations were performed on ten 12-core Apple Mac Pro microcomputers with Intel Westmere (2.40 GHz) processors. A cluster analysis of all conformations saved at 100-ps intervals from the ten 10-ns MD simulations was performed using PTRAJ of AmberTools 1.5 with the average-linkage algorithm (Shao et al., J. Chem. Theory Comput., 3:2312-2334 (2007)) (epsilon of 2.0 Å and root mean square coordinate deviation on all Ca atoms of the BH3-like domain). The occurrences of the three most populated clusters are 67%, 6%, and 5%, respectively. The structure displayed in FIG. 1D is the representative conformation of the most populated cluster identified by PTRAJ.

Results

During acute HIV infection, CD4 T cell death is initiated when viral RNA is detected by RIG-I (Solis et al., J. Virol., 85:1224-1236 (2011); and Jiang et al., Nature 479, 423-427 (2011), reverse transcribed viral DNA is detected by IFI-16 (Doitsh et al., Nature, 505:509-514 (2014)); and Monroe et al., Science, 343:428-432 (2014)), or HIV integrase-induced nicking of the host DNA is detected by DNA-PK (Cooper et al., Nature, 498:376-379 (2013)). When these death mechanisms fail, HIV integrates into the host genome and may enter a latent state in which the virus is transcriptionally silent, replication competent, and resistant to current therapies or immune attack. Upon viral reactivation from latency, which occurs during T cell activation, these innate immune sensing mechanisms are not activated, but HIV protease-mediated cleavage of the host protein procaspase 8 (Nie et al., *Cell Death Differ.*, 9:1172-1184 (2002); and Nie et al., *Open Virol. J.*, 2:1-7 (2008)) generates a fragment (Casp8p41) with an α-helical domain that directly activates the pro-apoptotic mitochondrial protein Bak to facilitate HIV-induced killing (Sainski et al., *J. Cell. Biol.*, 207:159 (2014)).

As described herein, central memory CD4 T cells, the principal reservoir of HIV, are intrinsically resistant to cell death due, in part, to elevated expression of Bcl 2. Further, it was demonstrate that Bcl-2 binds Casp8p41, inhibits Casp8p41-mediated killing, and diminishes T cell death following acute HIV infection in vitro, resulting in increased HIV production. Conversely, antagonizing Bcl-2 selectively promoted death of Casp8p41-containing cells and diminished HIV DNA following either acute HIV infection or HIV reactivation from latency ex vivo. These results demonstrate that apoptosis sensitization followed by HIV reactivation can reduce HIV burden.

Figure 2A:
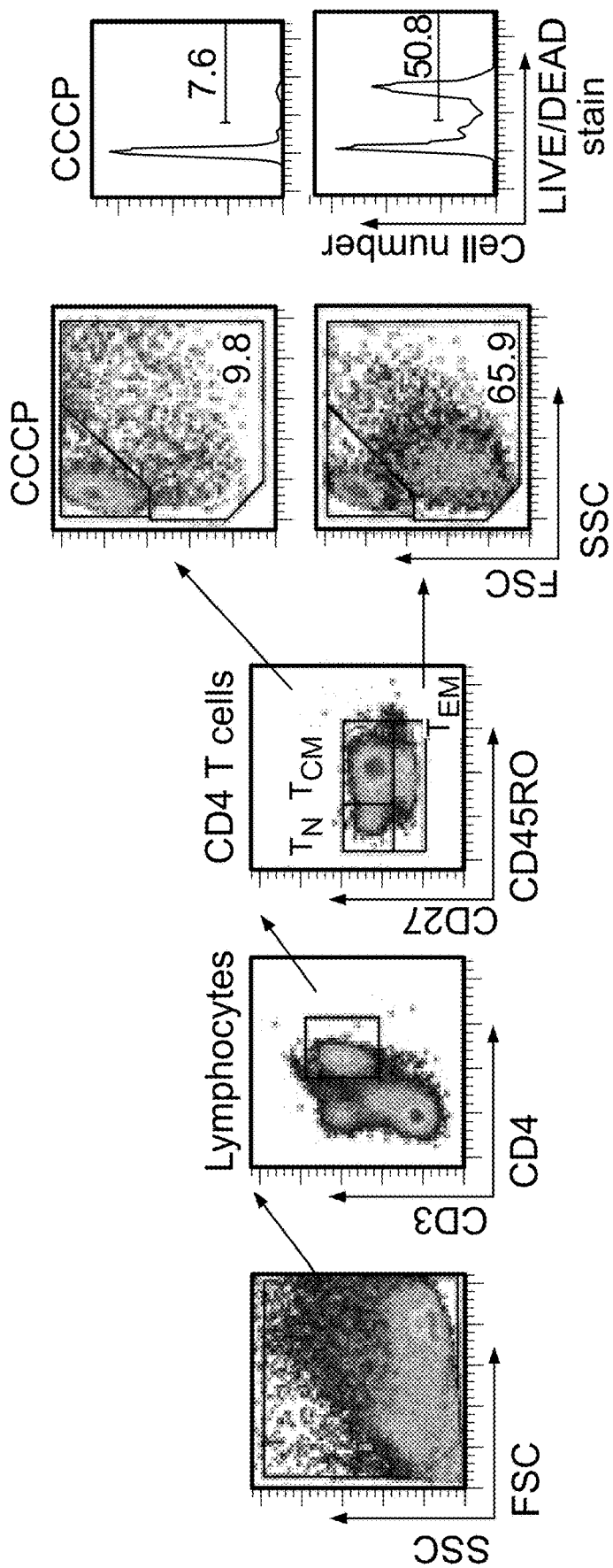
Figure 2D:
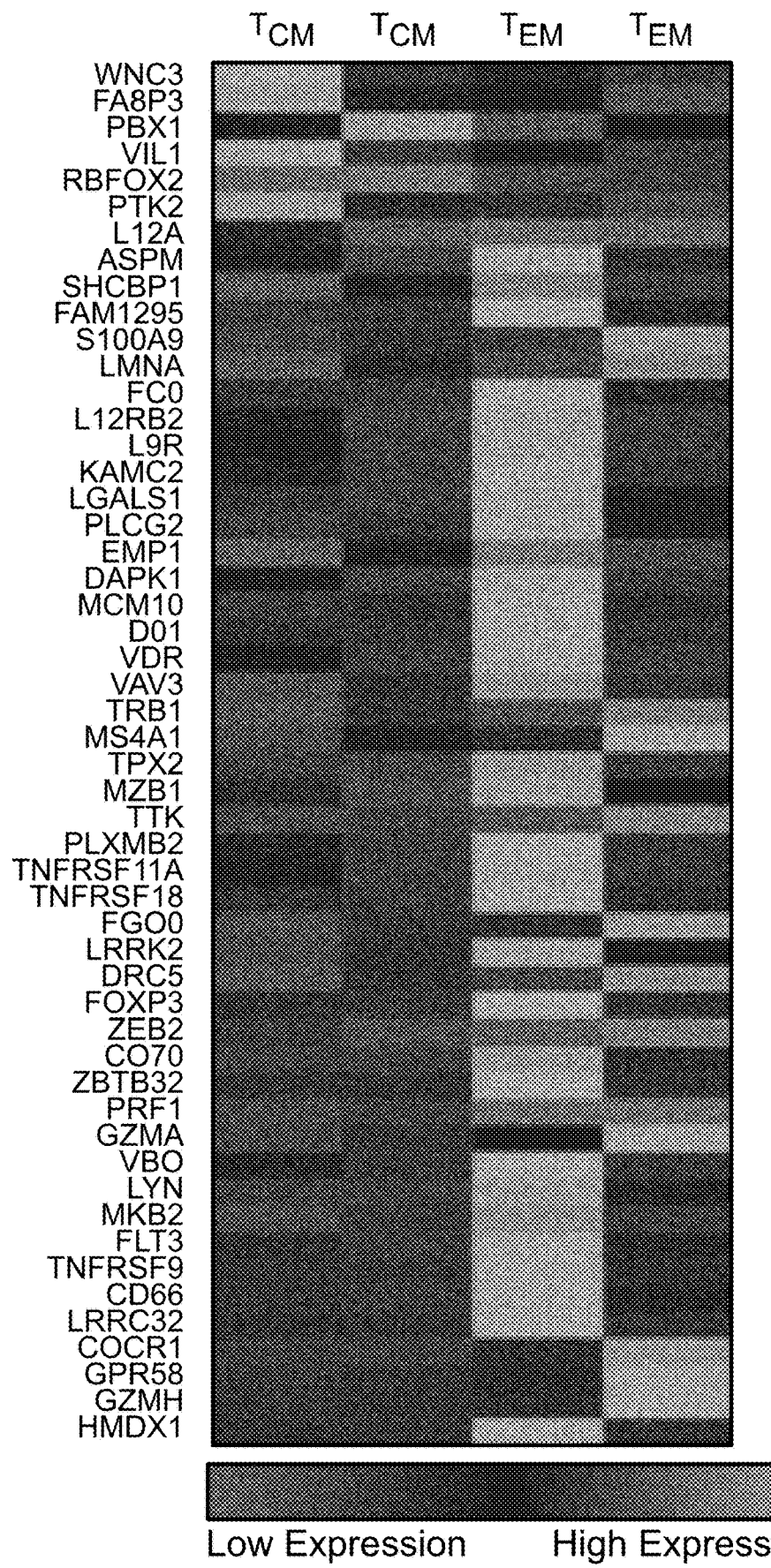

Once integrated into host DNA, HIV can remain in a latent state for years. In patients on suppressive ART, $T_{CM}$, which are long lived and proliferate in response to antigenic re-stimulation, constitute the principal HIV reservoir (Jaafoura et al., *Nat. Commun.*, 5:5407 (2014)). By contrast, $T_{EM}$ are a lesser reservoir (Chomont et al., *Nat. Med.*, 15:893-900 (2009)) and have a shorter half-life (Macallan et al., *J. Exp. Med.*, 200:255-260 (2004)). To assess whether the longer life span of $T_{CM}$ reflects intrinsic resistance to death stimuli, PBMCs from uninfected donors were treated with proapoptotic stimuli. $T_{CM}$ were less susceptible than $T_{EM}$ to Fas ligation and triggers of the mitochondrial apoptotic pathway (FIGS. 2A-2C). RNAseq performed on $T_{CM}$ and $T_{EM}$ revealed increased expression of six proliferation genes and decreased expression of 46 cell death genes by at least 2-fold in $T_{CM}$ ($p=6.5\times10^{-6}$ for enrichment of the death and proliferation gene sets, FIG. 2D), providing a potential explanation for the apoptosis resistance of $T_{CM}$. Importantly, eradication of HIV required elimination of these apoptosis resistant cells if they harbor the virus.

Figures 2E, 2F:
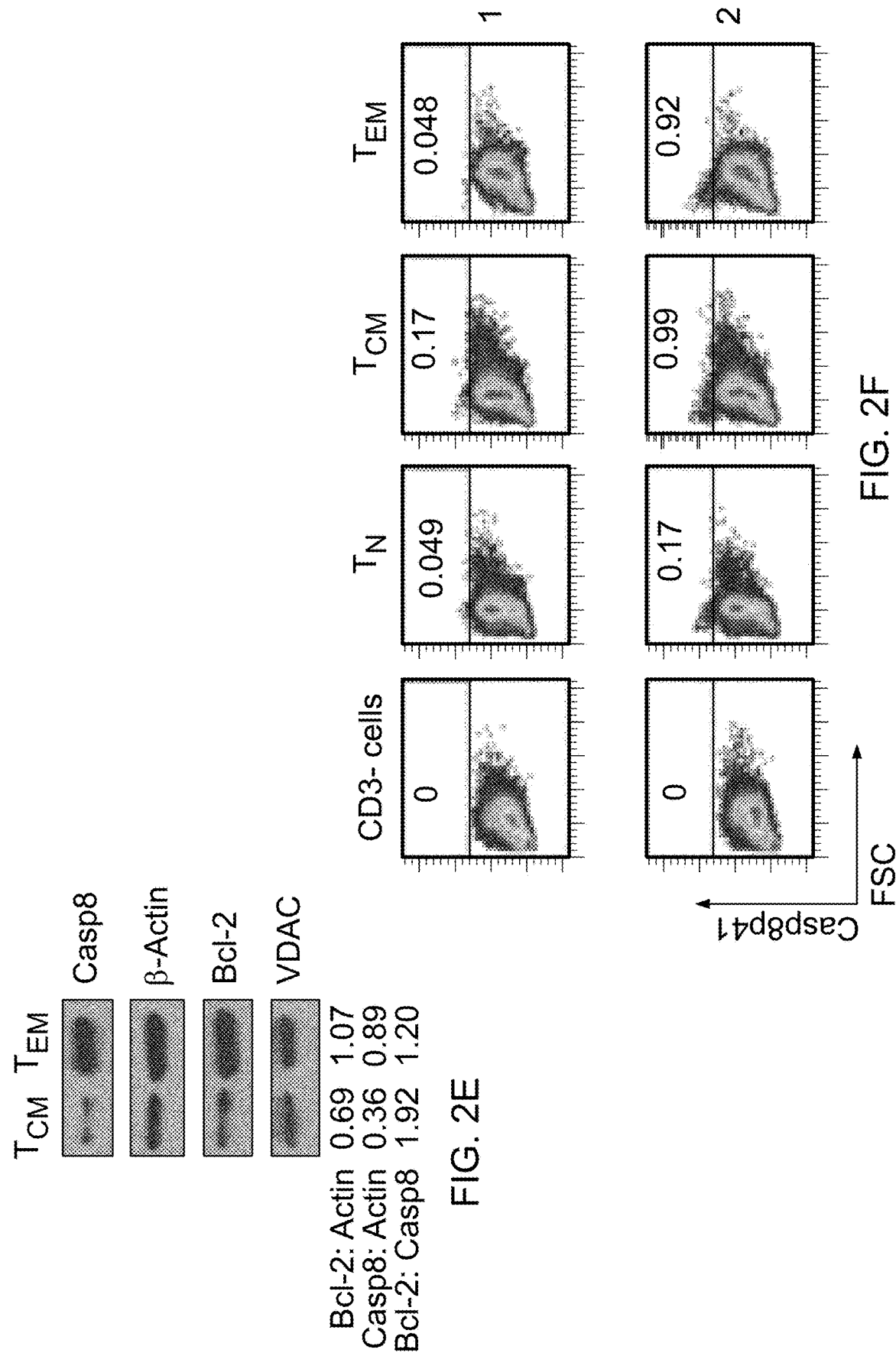
Figures 2G, 2H:
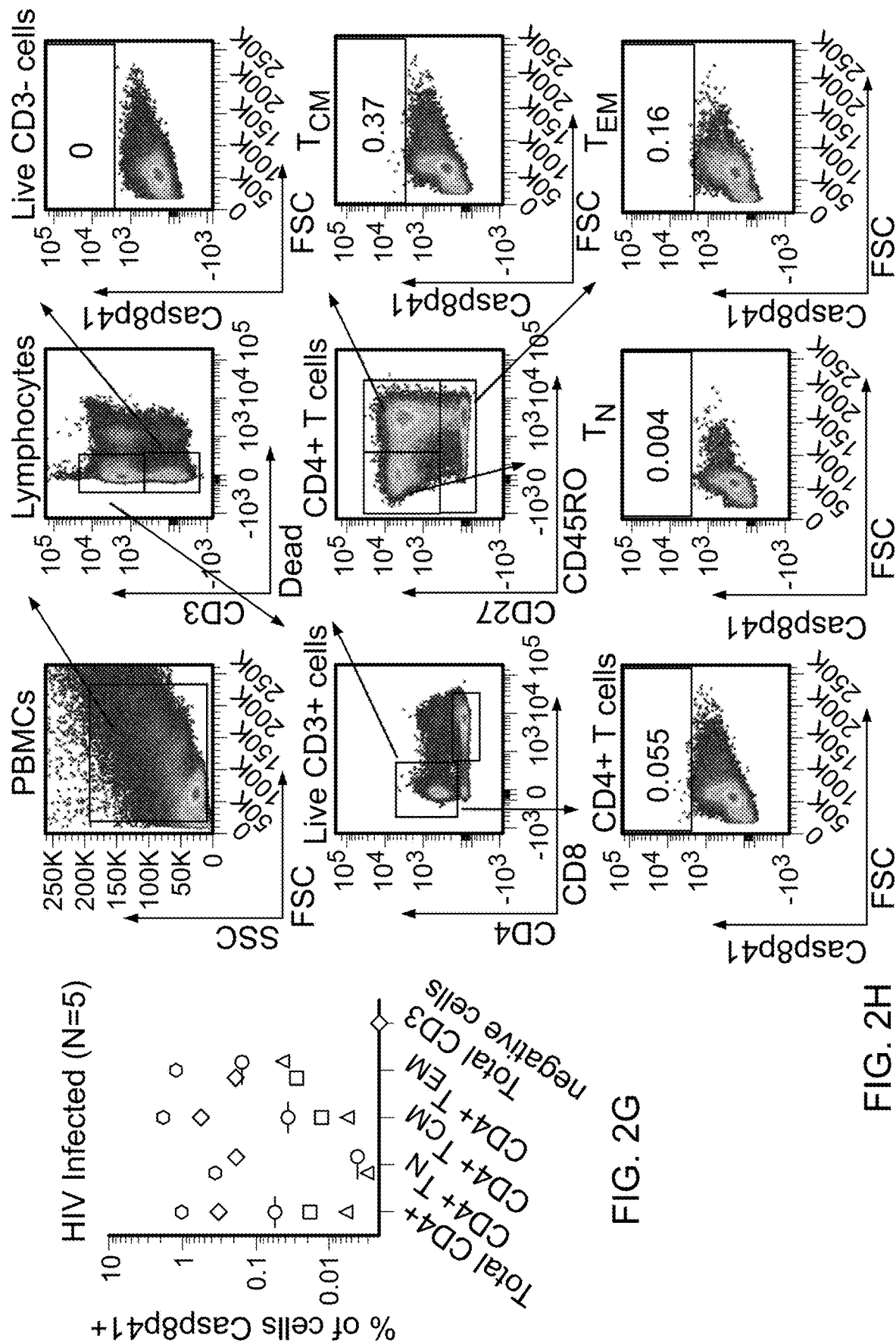
Figure 2I:
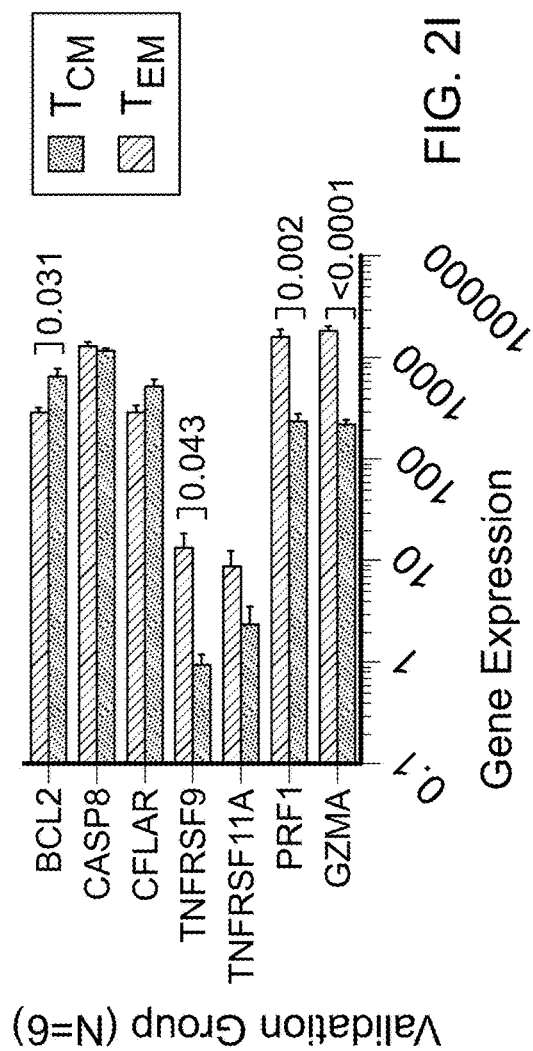

The results were consistent with other gene expression data (GSE61697, Gene Expression Omnibus) showing higher expression of BCL-2 and lower expression of four other genes that impact T cell survival (TNFRSF9, TNFRSF11A, PRF1 and GZMA) in $T_{CM}$ compared to $T_{EM}$ (FIG. 2I; Takeshita et al., *Clin. Immunol.*, 159:107-117 (2015)).

In light of results showing that Casp8p41 can act like a BH3-only protein, there are two possible reasons why $T_{CM}$ that reactivate HIV might not die: Either Casp8p41 is not generated, or the proapoptotic effects of Casp8p41 are antagonized by intrinsic resistance mechanisms. Since $T_{CM}$ express Caspase 8 (FIG. 2E) and flow cytometry readily detected Casp8p41 in $T_{CM}$ from HIV-infected patients (FIG. 2F), whether there is a block to Casp8p41-mediated apoptosis was assessed. Because the Bcl-2:Caspase8 ratio is higher in $T_{CM}$ than $T_{EM}$ (FIG. 2E), the impact of Bcl-2 on Casp8p41-mediated killing was assessed in Jurkat T cells. After transfection with EGFP-Casp8p41, successfully transfected cells were identified by their EGFP fluorescence and assayed for cell killing using terminal deoxynucleotidyl-transferase dUTP nick end labeling (TUNEL). Bcl-2 overexpression diminished the number of EGFP-Casp8p41$^+$ cells that were TUNEL$^+$ (FIG. 3A, p=0.004) despite similar Casp8p41 expression (FIGS. 3B and 4). If Bcl-2 overexpressing cells die less following HIV infection, then more cells should survive to produce more progeny HIV virions. Consistent with this prediction, Bcl-2 overexpression increased cell survival following HIV infection, cell associated HIV DNA, and HIV p24 production (FIGS. 3C-3E and 5), demonstrating that altering Bcl-2 fundamentally impacts the magnitude of viral replication and number of HIV-infected cells.

In addition, since $T_{CM}$ express detectable levels of Caspase 8 (FIG. 2E), $T_{CM}$ from five chronically HIV-infected people were analyzed to determine whether they generate Casp8p41 in vivo (FIGS. 2G and 2H). Flow cytometry readily detected Casp8p41 in 0.006 to 1.86% of $T_{CM}$, as well as 0 to 0.36% of TN and 0.006 to 1.22% of $T_{EM}$; but was not detected in CD3 negative cells. This frequency of Casp8p41 positivity in resting memory CD4 T cells was similar to the frequency of Gag sequences in memory CD4 T cells found in another study that detected 100 to 10,000 Gag copies per $10^5$ highly purified sorted memory CD4 T cells from HIV infected patients (Brenchley et al., *J. Virol.*, 78:1160-1168 (2004)).

BCL-2 Inhibits Casp8p41-Induced Cell Death

To assess whether BCL-2 alters the ability of Casp8p41 to kill cells, the responses of parental Jurkat T cells versus Jurkat cells stably overexpressing BCL-2 (Jurkat-BCL-2) were compared to transient GFP-Casp8p41 expression. After transfection, Casp8p41-induced apoptosis, as measured by TUNEL positivity (FIGS. 3G and 3A), was greater in parental Jurkat cells than Jurkat-BCL-2 cells (FIG. 3F, Mean AUC 1500 vs 870 [95% CI of difference −790, −480; P=0.004]) despite similar Casp8p41 expression (FIG. 3B). Thus, cells overexpressing BCL-2 die less in response to Casp8p41, indicating that BCL-2 antagonizes Casp8p41 induced killing.

To determine whether BCL-2 overexpression impacts Casp8p41-mediated BAK activation, Jurkat or Jurkat-BCL-2 cells were transfected with GFP or GFP-Casp8p41 and stained with conformational specific antibodies that recognize activated BAK, but not inactive BAK. As expected, GFP-Casp8p41$^+$ expressing parental Jurkat cells (identified as GFP$^+$ by flow cytometry) contained more activated BAK than parental cells expressing GFP alone (MFI difference 52±16, P=0.029; FIGS. 3H and 3E). In contrast, GFP-Casp8p41$^+$ Jurkat-BCL-2 cells did not exhibit increased BAK activation compared to GFP alone (MFI difference 3.5±16, P=0.834), indicating that BCL-2 prevents BAK activation in response to Casp8p41 expression. Accordingly, the overall number of activated BAK$^+$ cells after GFP-Casp8p41 transfection was lower in Jurkat-BCL-2 cells compared to Jurkat cells (P=0.045). Thus, BCL-2 inhibited Casp8p41-induced BAK activation.

Figure 1H:
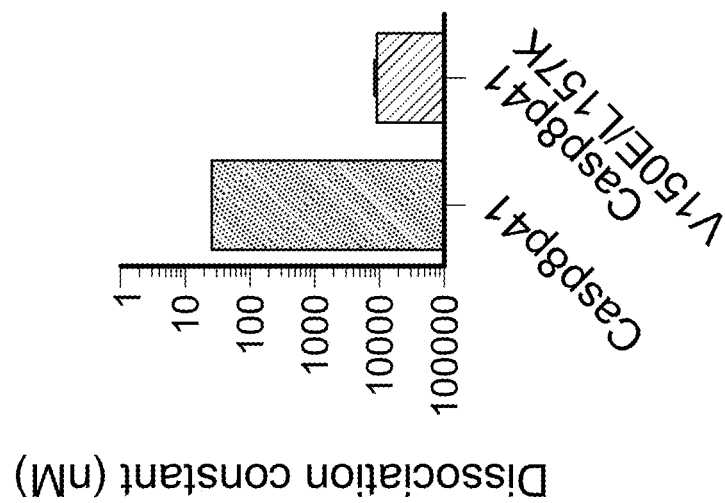
FIG. 1H, KDs determined as in panel G. Bars in C, F, and H: mean±SD from 3 independent experiments.
Figure 1G:
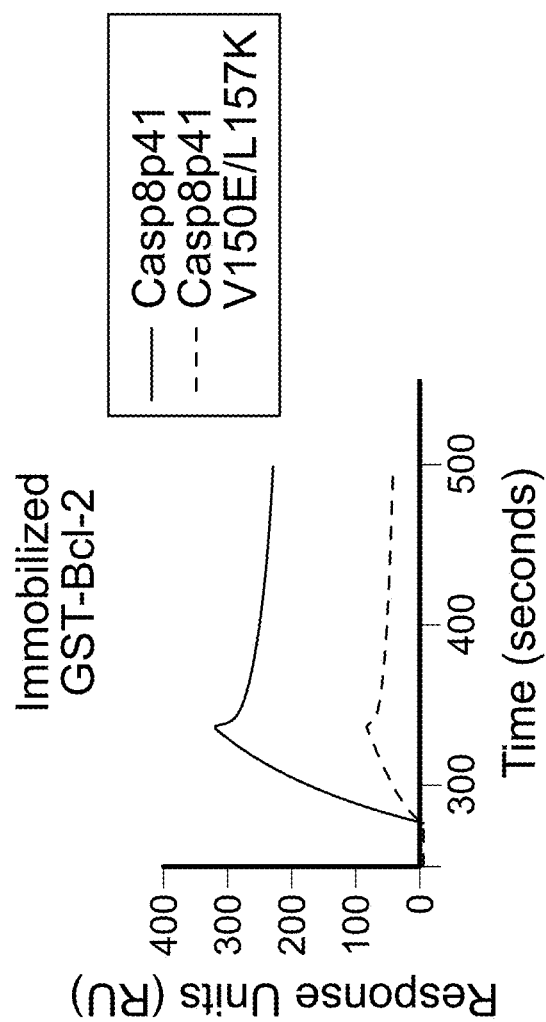
FIG. 1G, Binding of 200 nM GST-Casp8p41 or GST-Casp8p41 Val150Glu/Leu157Lys to immobilized GST-Bcl-2.

Because Casp8p41 contains an alpha helical activator domain that can bind the BH3 binding groove of Bak (Sainski et al., *J. Cell. Biol.*, 207:159 (2014)), whether the same domain can bind antiapoptotic Bcl-2 family members as well was evaluated. In initial experiments, Bcl-2 was immunoprecipitated from lysates of 293T cells transfected with empty vector, HA-Casp8p41, or HA-Casp8p41 Val150Glu/Leu157KLys (a variant with decreased affinity for Bak (Sainski et al., *J. Cell. Biol.*, 207:159 (2014))). An interaction of Bcl-2 with HA Casp8p41 that was reduced by the Val150Glu/Leu157KLys modification was observed (FIG. 1A). In further experiments, SPR demonstrated equilibrium mean dissociation constants (Kds) of 13 nM for Casp8p41 binding to purified recombinant Bcl-2, 11 nM for Bcl xL, and 8 nM for Mcl-1 (FIGS. 1B-1C). Purified activator domain peptide also bound Bcl-2, providing evidence that the same Casp8p41 domain is responsible for binding both Bak and Bcl-2 (FIG. 6A). Using multiple low-mass molecular dynamic simulations (Pang, *Biochem. Biophys. Res. Commun.*, 452:588-592 (2014)), a three-dimensional model of that peptide bound in the BH3 binding groove of Bcl-2 (FIG. 1D) that predicts a critical interaction of Bcl-2 Arg146 with Casp8p41 Glu147 and Glu154 was determined. Substitution of Ala for Bcl-2 Arg146, which inhibits Bcl-2•Bim interaction (Smith et al., *J. Biol. Chem.*, 286:17682-17692 (2011)), decreased the affinity of Bcl-2 for the Casp8p41 activator peptide (FIG. 6B) or full length Casp8p41 250-fold (FIGS. 1E-1F), confirming that Casp8p41 binds the Bcl-2 BH3 binding groove. The model also predicted that Casp8p41 Val150 and Leu157 bind in the two hydrophobic regions in the Bcl-2 BH3 binding groove. Consistent with this prediction, the affinity of Casp8p41 for Bcl-2 was reduced over 300-fold by the Val150Glu/Leu157Lys Casp8p41 modification (FIGS. 1G-1H). These results indicate that the Casp8p41 activator domain can interact with the BH3 binding groove of anti-apoptotic Bcl-2 family members as well as Bak.

Venetoclax is a Clinically Relevant BCL-2 Antagonist that Impacts Casp8p41-Mediated Killing Venetoclax (formerly known as ABT-199), potently and selectively inhibits BCL-2 binding to BH3 domains (Souers et al., *Nat. Med.*, 19:202-208 (2013)), is well tolerated in early phase clinical trials (Correia et al., *Biochim Biophys Acta*, 1853:1658-1671 (2015)), and achieves peak plasma levels of up to 5 µM (Matthew et al., *Blood*, 122:872 (2013)). The impact of venetoclax on T cells expressing Casp8p41 or reactivating HIV was assessed. In initial experiments, treatment with increasing doses of venetoclax (up to 1 µM) did not result in increased apoptosis of either parental Jurkat cells transfected with no DNA or Jurkat cells expressing eGFP compared to diluent control (FIG. 11A). In contrast, venetoclax (1 µM) significantly increased cell death in Jurkat cells expressing eGFP-Casp8p41 (mean difference 25.7±10.3%, P=0.016, FIG. 11A). This selective enhancement of killing induced by Casp8p41 but not generalized toxicity was further evaluated by treating primary uninfected CD4 T cells with venetoclax. Importantly, uninfected CD4 T cells (N=7 patients) treated with venetoclax (1 µM) for up to five days did not exhibit reduced viability compared to control treated cells (mean difference −7.2±4.8% at Day 5, P=0.16, FIG. 11B). Furthermore, uninfected CD4 T cells treated with venetoclax did not exhibit altered mitogen-induced proliferation as measured by CFSE dilution (mean difference in percent CFSE low cells at Day 3-1.1±7.9%, P=0.90, FIG. 11C). The lack of toxicity of venetoclax towards CD4 T cells from HIV uninfected donors was also seen using cells from HIV infected, but ART suppressed, patients; venetoclax (1 µM) for 24 hours did not adversely affect viability of bulk primary CD4 T cells (mean difference −4.7±1.6% viable, FIG. 11D). These favorable safety findings in vitro have also been seen in vivo: in 40 NHL patients receiving venetoclax monotherapy, only 2 cases of dose limiting neutropenia were observed (Matthew et al., *J. Clin. Oncol.*, 32:53 (2014)). These results demonstrate the possibility that venetoclax can be used safely in HIV infected patients.

Simultaneous Detection of Markers of HIV Infection and Apoptosis

If BCL-2 neutralizes Casp8p41, then antagonizing BCL-2 should augment Casp8p41-induced killing, including when Casp8p41 is generated by latently HIV infected cells that reactivate the virus. Before testing this possibility, whether select markers (protein or nucleic acid based) remain detectable was first assessed when the cell of interest is undergoing death. Jurkat T cells stably expressing eGFP were treated with vehicle control or the cytotoxic quinolone alkaloid CPT to induce apoptosis, then examined for expression of eGFP (as a prototypic cytoplasmic protein) and actin mRNA (as a prototypic mRNA) over time. Treatment of GFP+Jurkat cells with CPT decreased cell viability as measured by cellular ATP content (FIG. 12A) and light scatter (FIG. 12B) compared to diluent-treated cells.

Coincident with the loss in viability was a decrease in detectable eGFP (17% eGFP+ with CPT vs. 91% eGFP+ with diluent, FIG. 12C) and detectable actin message (34% reduction compared to diluent control) as assessed by qRT-PCR (FIG. 12D). As the proportion of active caspase-3$^+$ cells (FIG. 12E), TUNEL+ cells (FIG. 12F) or membrane permeable cells (FIG. 12G) increased over time, there was a reciprocal decrease in detectable eGFP (FIG. 12C) despite the fact that virtually all cells were eGFP positive at baseline. For example, by 48 hours, 97% of CPT treated cells were eGFP negative, despite having been uniformly eGFP positive. Accordingly, estimating the proportion of dead or dying cells that express a degradable marker of interest (e.g., HIV p24 or HIV RNA/DNA) will substantially underestimate the proportion of cells that expressed the marker before encountering the death stimulus. Therefore, the ability to detect protein or nucleic acid based phenotypic markers is impaired as cell death proceeds, rendering this approach insensitive and prone to incorrect phenotyping of the dying cell.

Accordingly, to approach the question of whether HIV reactivation in concert with BCL-2 antagonism reduces cell associated HIV DNA, we compared HIV DNA content in treated compared to control samples rather than simultaneously assessing markers of HIV and cell death in the same cells.

Again, if Bcl-2 inhibits HIV induced cell death by binding the Casp8p41 activator domain, disruption of this interaction should augment both Casp8p41-mediated killing and HIV-induced cell death. Consistent with this possibility, the Bcl-2 antagonist ABT-19914 increased killing by EGFP-Casp8p41 (FIGS. 7A and 8), but not control vector. Likewise, ABT-199 decreased survival of CD4 T cells following acute HIVIIIb infection (FIGS. 7B and 9), but had no effect on survival or mitogen-induced proliferation of mock-infected CD4 T cells (FIGS. 7B-7C). In addition, ABT-199 reduced supernatant HIV p24 levels (FIG. 7D), potentially reflecting death of HIV producing cells, a direct effect of ABT-199 on HIV replication, or both. Indeed, HIV LTR-Luciferase reporter constructs demonstrated that ABT-199 inhibits both basal and prostratin-induced HIV transcription in primary CD4 T cells (FIG. 7E). While the mechanism by which ABT-199 inhibits HIV LTR transcription is unknown, Bcl-2 overexpression has been associated with NFκB activation in some studies (Mortenson et al., *J. Cell. Biochem.*, 102:1171-1179 (2007)), but not others (Grimm et al., *J. Cell Biol.*, 134:13-23 (1996)). ABT-199 also decreased cell associated HIV-1 DNA compared to vehicle control treated cells (FIG. 7F). These results, coupled with the lack of toxicity of ABT-199 in uninfected cells (FIG. 7B), demonstrate that ABT-199 preferentially kills HIV-infected cells, resulting in lower HIV replication and fewer HIV infected cells. Similar effects on survival of infected cells, p24 production, and cell-associated HIV-1 DNA were seen with navitoclax (FIGS. 7G-7I), an inhibitor of Bcl-2, Bcl-xL, and Bcl-w (Tse et al., Cancer Res., 68:3421-3428 (2008)), although navitoclax caused more toxicity in uninfected cells (FIG. 7G).

Because ABT-199 reduces HIV replication and decreases the number of cells containing HIV DNA during acute infection in vitro, the effects of this agent during HIV latency were examined. When cryopreserved CD4 T cells from suppressed HIV-infected patients were purified, treated with diluent or ABT-199, and reactivated with αCD3/αCD28 in the presence of tenofovir and raltegravir to prevent spreading infection, ABT-199 reduced cell associated HIV DNA in a dose dependent manner (FIG. 10A). In addition, 8 of 11 (73%) freshly isolated primary CD4 T cell samples with cell associated HIV DNA measurable in the control sample exhibited a decrease after ABT-199 (FIG. 10B). ABT-199 also increased the proportion of Casp8p41 positive $T_{CM}$ cells containing active caspase 3 (FIG. 10C), indicating that Bcl-2 inhibition enhances Casp8p41-mediated killing of HIV-infected $T_{CM}$ cells that reactivate HIV.

Active caspase 3 (a marker of apoptotic cell death) was assessed in p24+(HIV infected) and p24− cells that were primed with venetoclax and reactivated with αCD3/αCD28. Median cell death, as measured by active caspase 3 staining in the p24− cells, was 2.5% in the control treated αCD3/αCD28 sample and was not changed significantly by venetoclax (10.3%, P=0.189, FIG. 10D). In contrast, venetoclax increased the proportion of HIV p24+ CD4+ cells that are active caspase 3+ compared to control treated cells (from 23% active caspase 3+ in control sample to 47% active caspase 3+ in the venetoclax sample, P=0.026, FIG. 10D). Of note, the frequency of p24 positive cells in reactivated CD4 T cells was similar to other previous reports (Deng et al., Nature, 517:381-385 (2015); and Pegu et al., Nat. Commun., 6:8447 (2015)). HIV RNA in the cell culture supernatant was not altered by venetoclax treatment compared to control (FIG. 10E), indicating that venetoclax does not impair the ability of cells to reactivate HIV.

The results provided herein demonstrate that Casp8p41 interacts with antiapoptotic Bcl-2 family members. Conversely, Bcl-2 inhibition released Casp8p41 and pro-apoptotic Bcl-2 family members, causing more HIV infected cells to die and thereby resulting in reduced HIV replication and fewer cells that contain HIV DNA. Importantly, the HIV reservoir was reported to be stable over time (Josefsson et al., Proc. Natl. Acad. Sci. USA, 110:E4987-4996 (2013)) and unaffected by antiretroviral therapy intensification (Puertas et al., AIDS, 28:325-334 (2014) even in conjunction with therapeutic vaccination (Achenbach et al., The Lancet HIV, 2:e82-e91 (2015)). In contrast, the results provided herein demonstrate that a single treatment with ABT-199 can, through release of Casp8p41, diminish HIV DNA, providing the first evidence that it is possible to pharmacologically diminish HIV reservoir size.

In summary, these results demonstrate that venetoclax-mediated inhibition of BCL-2 in all cells has minimal effect on cell viability in uninfected cells (FIGS. 11A-11D) yet promotes the preferential killing of p24+459 (HIV replicating) cells. Moreover, these results demonstrate the identification of a clinically relevant treatment that converts HIV reactivation from latency without killing of the reactivating cell (FIG. 13A) into an event that kills the reactivating cell by priming all cells towards apoptosis sensitive phenotype and then allows HIV infected cells, which replicate virus and generate Casp8p41, to undergo apoptosis when BCL-2 is inhibited (FIG. 13B).

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for increasing the susceptibility of HIV infected cells within a human to Casp8p41-mediated cell killing, wherein said method comprises administering a Bcl-2 inhibitor to said human, wherein said Bcl-2 inhibitor is ABT-199, ABT-263, or Sabutoclax, thereby increasing the susceptibility of HIV infected cells within said human to Casp8p41-mediated cell killing.

2. The method of claim 1, wherein said Bcl-2 inhibitor is ABT-199.

3. The method of claim 1, wherein said Bcl-2 inhibitor is ABT263.

4. The method of claim 1, wherein said Bcl-2 inhibitor is Sabutoclax.

5. The method of claim 1, wherein said method comprises identifying said human as having an HIV infection.

6. The method of claim 1, wherein said method comprises administering an antiretroviral therapy to said human.

7. The method of claim 6, wherein said antiretroviral therapy comprises an HIV integrase inhibitor.

8. The method of claim 7, wherein said HIV integrase inhibitor is raltegravir, dolutegravir, or elvitegravir.

9. The method of claim 6, wherein said antiretroviral therapy comprises an HIV protease inhibitor.

10. The method of claim 9, wherein said HIV protease inhibitor is lopinavir or atazanavir.

11. The method of claim 6, wherein said antiretroviral therapy comprises a reverse transcriptase inhibitor.

12. The method of claim 11, wherein said reverse transcriptase inhibitor is emtricitabine, rilpivirine, and tenofovir.

13. The method of claim 1, wherein said method comprises administering emtricitabine, rilpivirine, and tenofovir to said human.

14. The method of claim 1, wherein said method comprises administering efavirenz, emtricitabine, and tenofovir DF to said human.

15. The method of claim 1, wherein said method comprises administering cobicistat, elvitegravir, emtricitabine, and tenofovir to said human.

16. The method of claim 1, wherein said method comprises administering abacavir, dolutegravir, and lamivudine to said human.

* * * * *